US011098072B2

(12) United States Patent
Dowd et al.

(10) Patent No.: US 11,098,072 B2
(45) Date of Patent: Aug. 24, 2021

(54) ALKENYL AND BETA-SUBSTITUTED PHOSPHONATES AS ANTIMICROBIAL AGENTS

(71) Applicants: The George Washington University, Washington, DC (US); Washington University in St. Louis, St. Louis, MO (US); George Mason University, Fairfax, VA (US); Saint Louis University, St. Louis, MO (US)

(72) Inventors: Cynthia Dowd, Washington, DC (US); Xu Wang, Washington, DC (US); Robert Carl Brothers, Washington, DC (US); Audrey Ragan Odom John, St. Louis, MO (US); Rachel Edwards, St. Louis, MO (US); Marvin Meyers, St. Louis, MO (US); Stacy Arnett, St. Louis, MO (US); Robin Couch, Fairfax, VA (US); Kenneth Heidel, Washington, DC (US)

(73) Assignees: The George Washington University, A Congressionally Chartered Not-for-Profit Corporation, Washington, DC (US); Washington University, St. Louis, MO (US); George Mason University, Fairfax, VA (US); St. Louis University, St. Louis, MO (US)

( * ) Notice: Subject to any disclaimer, the term of this patent is extended or adjusted under 35 U.S.C. 154(b) by 0 days.

(21) Appl. No.: 16/627,004

(22) PCT Filed: Jun. 27, 2018

(86) PCT No.: PCT/US2018/039777
§ 371 (c)(1),
(2) Date: Dec. 27, 2019

(87) PCT Pub. No.: WO2019/005982
PCT Pub. Date: Jan. 3, 2019

(65) Prior Publication Data
US 2020/0140469 A1   May 7, 2020

Related U.S. Application Data

(60) Provisional application No. 62/525,616, filed on Jun. 27, 2017.

(51) Int. Cl.
  C07F 9/38      (2006.01)
  A61P 33/06    (2006.01)
  A61P 31/06    (2006.01)
  C07F 9/40      (2006.01)

(52) U.S. Cl.
  CPC ............ *C07F 9/3826* (2013.01); *A61P 31/06* (2018.01); *A61P 33/06* (2018.01); *C07F 9/4015* (2013.01)

(58) Field of Classification Search
  CPC .................................................... C07F 9/3826
  See application file for complete search history.

(56) References Cited

FOREIGN PATENT DOCUMENTS

| AT | 364455 B | 10/1981 |
|----|----------|---------|
| WO | WO-2017127805 A1 | 7/2017 |
| WO | WO-2019005982 A1 | 1/2019 |

OTHER PUBLICATIONS

Iguchi, et al. Document No. 92:162084, retrieved from STN; (1980).*
Blakemore, P.R. Document No. 145:471124, retrieved from STN; (2005).*
Fokin, et al. Document No. 147:541613, retrieved from STN; (2007).*
Jackson, et al. Document No. 160:219027, retrieved from STN; (2014).*
Kuroda, et al. Document No. 92:162086, retrieved from STN; (1980).*
Oehler, et al. Document No. 125:168145, retrieved from STN; (1996).*
Okuhara, et al. Document No. 92:162085, retrieved from STN; (1980).*
Jackson, et al. Bioorganic & Medicinal Chemistry Letters 24 (2014) 649-653.*
Bjorkelid, C., et al., "Structural Studies on Mycobacterium Tuberculosis DXR in Complex With the Antibiotic FR-900098," Acta Crystallographica. Section D, Biological Crystallography 68(Pt 2):134-143, Wiley-Blackwell, United States (Feb. 2012).
Edwards, R.L., et al., "MEPicides: Potent Antimalarial Prodrugs Targeting Isoprenoid Biosynthesis," Scientific Reports 7(1):8400, Nature Publishing Group, England (Aug. 2017).
Guggisberg, A.M., et al., "A Sugar Phosphatase Regulates the Methylerythritol Phosphate (MEP) Pathway in Malaria Parasites," Nature Communications 5:4467, Nature Publishing Group, England (Jul. 2014).
International Search report and Written opinion for Application PCT/US2018/039777, dated Oct. 29, 2018, 9 pages, Commissioner of Patents, Alexandria, VA.
Jackson, E.R., et al., "The Effect of Chain Length and Unsaturation on Mtb Dxr Inhibition and Antitubercular Killing Activity of FR900098 Analogs," Bioorganic & Medicinal Chemistry Letters 24(2):649-653, Elsevier Science Ltd, England (Jan. 2014).

(Continued)

*Primary Examiner* — Shawquia Jackson
(74) *Attorney, Agent, or Firm* — Sterne, Kessler, Goldstein and Fox P.L.L.C.

(57) ABSTRACT

The present disclosure relates to novel compounds, pharmaceutical compositions, and methods for treating or preventing microbial infection caused by parasites or bacteria, such as Plasmodium falciparum or related Plasmodium parasite species and *Mycobacterium tuberculosis* or related *Mycobacterium* bacteria species. The compounds are α,β-unsaturated analogs of fosmidomycin and can inhibit deoxyxylulose phosphate reductoisomerase (Dxr) in many microbes, such as P. falciparum.

22 Claims, 10 Drawing Sheets

(56) References Cited

OTHER PUBLICATIONS

Jose, G.S., et al., "Structure-Activity Relationships of the MEPicides: N-Acyl and O-Linked Analogs of FR900098 as Inhibitors of Dxr From *Mycobacterium Tuberculosis* and *Yersinia Pestis*," ACS Infectious Diseases 2(12):923-935, ACS Publications, United States (Dec. 2016).

Pubchem, Substance Record for SID 128496555, Available Date: Dec. 4, 2011 [retrieved on Aug. 7, 2018]. Retrieved from the Internet: (URL:https://pubchem.ncbi.nlm.nih.gov/substance/128496555), entire document.

Giessmann, D., et al., "Towards New Antimalarial Drugs: Synthesis of Non-Hydrolyzable Phosphate Mimics as Feed for a Predictive QSAR Study on 1-Deoxy-D-xylulose-5-phosphate Reductoisomerase Inhibitors," Chemistry & Biodiversity 5(4):643-656, Wiley Online Library, United States (Apr. 2008).

\* cited by examiner

ALKENYL AND BETA-SUBSTITUTED PHOSPHONATES AS ANTIMICROBIAL AGENTS

CROSS-REFERENCE OF RELATED APPLICATION

This application claims priority to U.S. Provisional Application No. 62/525,616, filed Jun. 27, 2017; the entire contents of which are hereby incorporated by reference.

GOVERNMENT LICENSE RIGHTS

This invention was made with government support under Grant No. AI 123433 awarded by the National Institutes of Health. The U.S. government has certain rights in the invention.

BACKGROUND

1. Technical Field

The field of the present disclosures relates to compounds, pharmaceutical compositions, and methods for treating or preventing microbial infection caused by parasites or bacteria, such as Plasmodium falciparum or related Plasmodium parasite species and *Mycobacterium tuberculosis* or related *Mycobacterium* bacteria species.

2. Discussion of Related Art

Despite intense efforts in drug development and aggressive vector control programs, malaria remains a formidable challenge to public health. According to recent estimates, malaria causes 212 million clinical cases and more than 429,000 deaths each year, predominately in young children living in sub-Saharan Africa. While 5 species of Apicomplexan parasites of the genus Plasmodium cause human malaria, Plasmodium falciparum is the most deadly. Due to pervasive drug resistance, P. falciparum treatment has become increasingly dependent on a single class of compounds, the artemisinins. However, there is substantial evidence to suggest that the effectiveness of artemisinin combination therapies (ACTs) is waning, and as such, global malaria control efforts are threatened. The rapid increase in multidrug-resistant parasites combined with a chronic under-investment in drug discovery has severely limited existing therapies. As only a few new antimalarial agents are in the clinical pipeline, identification of novel drug targets is essential.

The methylerythritol phosphate (MEP) pathway of isoprenoid biosynthesis is an unexploited drug target present in most eubacteria and apicomplexan protozoa. In P. falciparum, the MEP pathway enzymes are apicoplast-localized, and data suggest that isoprenoid precursor biosynthesis is the only essential function of the plastid organelle in blood-stage parasites. The pathway begins with the condensation of pyruvate and glyceraldehyde-3-phosphate and then proceeds through a series of enzymatic reactions to produce isopentenyl pyrophosphate (IPP) and dimethylallyl diphosphate (DMAPP), which are used to synthesize downstream products. The enzymes of the MEP pathway are essential, as isoprenoids are required for numerous cellular processes including aerobic respiration, membrane stability, and protein prenylation. Importantly, humans employ an alternate route for isoprenoid generation, using instead the mevalonate pathway whose components lack similarity to MEP pathway enzymes. Due to the essentiality of the MEP pathway in P. falciparum (FIG. 1) and the absence of mammalian homologs, compounds that would specifically inhibit enzymes in the pathway are paramount.

The first committed enzyme of the MEP pathway is catalyzed by 1-deoxy-D-xylulose-5-phosphate reductoisomerase (Dxr/IspC; EC 1.1.1.267), and considerable efforts have been made to effectively target the enzyme. Dxr catalyzes the reductive isomerization of 1-deoxy-D-xylulose 5-phosphate (DOXP) to 2-C-methyl-D-erythritol 3-phosphate (MEP), using a divalent cation ($Mg^{2+}$, $Mn^{2+}$, or $Co^{2+}$) and NADPH as a cofactor. Chemical inhibition of Dxr in blood-stage P. falciparum depletes cellular MEP metabolites, and ultimately kills the parasites. Moreover, genetic disruption of the Dxr locus in P. falciparum (PF3D7_1467300) is only feasible if cultures are artificially supplemented with downstream isoprenoids. Further, Dxr is druggable, contains a high flux-control coefficient, and is one of only seven antimalarial targets that have been clinically validated.

*Mycobacterium tuberculosis* (Mtb) is the causative agent of tuberculosis. Two mechanisms are known for the biosynthetic production of isoprenoid units: the mevalonate pathway found in mammals and plants, and the nonmevalonate pathway found in most bacteria. There are no human homologues for the enzymes of the nonmevalonate pathway and each enzymatic reaction is vital to the survival of bacteria. These enzymes are thus prospective targets for therapeutic intervention of *M. tuberculosis*. Dxr is essential for the growth of Mtb. Current anti-TB drugs do not target the nonmevalonate pathway, so Dxr inhibition would be a new mechanism of action.

Fosmidomycin (Scheme 1, 1a), isolated from *Streptomyces lavendulae*, is a potent inhibitor of P. falciparum DXR ($IC_{50}$=0.034 µM). FR900098 (Scheme 1, 1b), the N-acetyl analog of fosmidomycin isolated from *Streptomyces* rubellomurinus, is roughly equipotent to fosmidomycin (P. falciparum DXR $IC_{50}$=0.024 µM). While these two natural products have submicromolar inhibition of P. falciparum growth ($IC_{50}$=0.09-0.35 µM), their use as a single drug therapy is limited by low bioavailability, short serum half-life, and malaria recrudescence.

Scheme 1

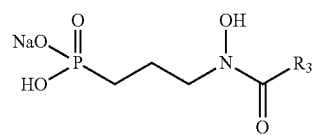

$R_3$ = H; fosmidomycin, 1a
$R_3$ = $CH_3$; FR90098, 1b

Therefore, there is an ongoing need for new Dxr inhibitors to combat microbial infection caused by, for example, P. falciparum malaria and *M. tuberculosis*.

SUMMARY

The present disclosure relates to a compound having the chemical structure of Formula (I):

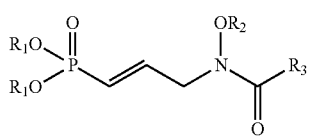

(I)

or a pharmaceutically acceptable salt or prodrug thereof, wherein each $R_1$ is independently H, $C_{1-6}$ alkyl, $C_{1-6}$ haloalkyl, $C_{3-6}$ cycloalkyl, $(CR^aR^b)_m$-aryl, $(CR^aR^b)_m$—O(C=O)—$C_{1-6}$ alkyl, $(CR^aR^b)_m$—O(C=O)—$C_{3-6}$ cycloalkyl, $(CR^aR^b)_m$—O(C=O)-aryl, $(CR^aR^b)_m$—O(C=O)O—$C_{1-6}$ alkyl, $(CR^aR^b)_m$—O(C=O)O—$C_{3-6}$ cycloalkyl, wherein the atom at the left is attached to the oxygen atom; or two $R_1$ taken together with the oxygen atoms and the phosphorus atom to form a 5- to 6-membered optionally substituted ring;

$R_2$ is H or $(CR^cR^d)_n$-aryl, wherein the atom at the left is attached to the oxygen atom;

$R_3$ is H, $C_{1-6}$ alkyl, $C_{1-6}$ haloalkyl, $C_{3-6}$ cycloalkyl, $C_{1-6}$ alkoxy, $C_{1-6}$ haloalkoxy, $C_{3-6}$ cycloalkoxy, or $(CR^eR^f)_p$-aryl;

each $R^a$, $R^b$, $R^c$, $R^d$, $R^e$, and $R^f$ is independently H, halogen, methyl, or ethyl; m and n is independently 1, 2, 3, or 4;

p is 0, 1, 2, 3, or 4;

each aryl is optionally substituted with up to five $R_4$ selected from the group consisting of halogen, hydroxyl, cyano, amino, ($C_{1-6}$ alkyl)amino, di($C_{1-6}$ alkyl)amino, $C_{1-6}$ alkyl, $C_{1-6}$ haloalkyl, $C_{3-6}$ cycloalkyl, $C_{1-6}$ alkoxy, $C_{1-6}$ haloalkoxy, and $C_{3-6}$ cycloalkoxy; provided that the compound is not

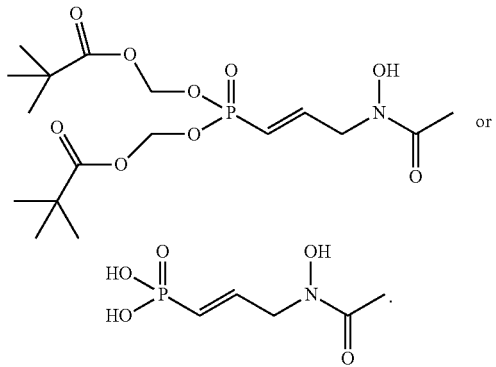

The present disclosure also provides a pharmaceutical composition comprising the compounds disclosed herein and a pharmaceutically acceptable excipient.

The present disclosure also provides a method for treating or preventing a microbial infection in a subject in need thereof comprising administering to the subject an effective amount of the compounds disclosed herein.

In some embodiments, the microbial infection is malaria. In some embodiments, the microbial infection is tuberculosis.

BRIEF DESCRIPTION OF THE DRAWINGS

Further objectives and advantages will become apparent from a consideration of the description, drawings, and examples.

FIG. 2 depicts that addition of IPP, the product of the MEP pathway, rescues growth of parasites (open shapes) treated with 12a and 18a.

FIG. 9 depicts that addition of IPP, the product of the MEP pathway, rescues growth of parasites (open shapes) treated with 32a and 33a.

FIG. 10 depicts that P. falciparum had1 mutant strains resistant to fosmidomycin (1a) are also resistant to 32a and 33a.

DETAILED DESCRIPTION

Figure 1:
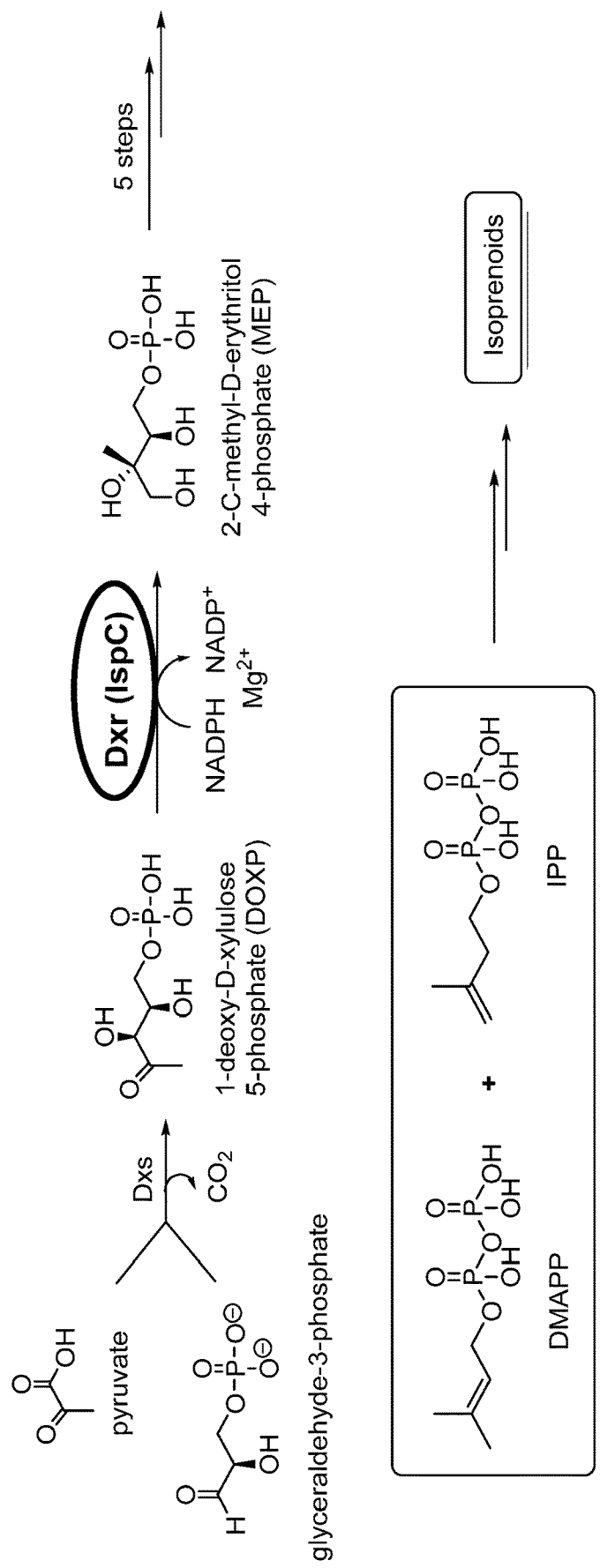
FIG. 1 depicts the methyl erythritol phosphate (MEP) pathway of isoprenoid biosynthesis.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

Definitions

As used throughout the term "subject" refers to a mammal. In some cases, the mammal is human. In some cases, the mammal is an animal.

The term "in need thereof" refers to a subject infected with a microbial pathogen or at risk of becoming infected by the microbial pathogen. In some cases, the microbial pathogen is a eukaryotic pathogen, and more specifically a eukaryotic pathogen belonging to the genus Plasmodium. In some cases the pathogen is a prokaryotic pathogen, and more specifically belonging to the genus Mycobacterium.

As used throughout, the phrase an "effective amount" of a compound of this disclosure is measured by the therapeutic effectiveness of the compound, wherein at least one adverse effect of a disorder is ameliorated or alleviated. More specifically, administering a compound or composition results in complete or at least partial inhibition of a metabolic pathway or other biological processes in a pathogen. In addition, an effective amount is sufficient to result in at least some degree of alleviation or prevention of an infection caused by a pathogen, or prevention of an infection by the pathogen.

The terms "treating or preventing" are intended to include preventing, eradicating, or inhibiting the resulting increase of undesired physiological activity associated with a disorder or infection, for example, in the context of the therapeutic or prophylactic methods of the invention. In another embodiment, the term treating or preventing includes antagonistic effects, e.g., diminishment of the activity or production of mediators of a disorder.

As used herein and unless otherwise indicated, the term "formulation" refers to a composition comprising a compound of the present disclosure that is described in a particular dosage form (e.g., tablet) or with a particular dosage amount.

When administered to a subject (e.g., to an animal for veterinary use or to a human for clinical use), the compounds of the invention can be optionally administered in isolated form.

The phrase "pharmaceutically acceptable salt(s)," as used herein includes but is not limited to salts of acidic or basic groups that may be present in compounds of the present disclosure. Compounds in the present disclosure that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions including, but not limited to, sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds in the present disclosure that include an amino moiety may form pharmaceutically acceptable salts with various amino acids, in addition to the acids mentioned above. Compounds in the present disclosure that are acidic in nature are capable of forming base salts with various pharmacologically acceptable cations. Examples of such salts include alkali metal or alkaline earth metal salts and ammonium salts, for example, calcium, magnesium, sodium, potassium, lithium, zinc, potassium, and iron salts.

As used herein and unless otherwise indicated, the term "pharmaceutically acceptable prodrug" means a derivative of a compound that can hydrolyze, oxidize, or otherwise react under biological conditions (in vitro or in vivo) to provide the compound. Examples of prodrugs include, but are not limited to, compounds that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include compounds that comprise oligonucleotides, peptides, lipids, aliphatic and aromatic groups, or NO, NO2, ONO, and ONO2 moieties. Prodrugs can typically be prepared using well known methods, such as those described in Burger's Medicinal Chemistry and Drug Discovery, pp. 172, 178, 949, 982 (Manfred E. Wolff ed., 5th ed. 1995), and Design of Prodrugs (H. Bundgaard ed., Elsevier, New York 1985).

The phrase "pharmaceutically acceptable excipient" may be any substance, not itself a therapeutic agent, used as a carrier, diluent, adjuvant, binder, and/or vehicle for delivery of a therapeutic agent to a patient, or added to a pharmaceutical composition to improve its handling or storage properties or to permit or facilitate formation of a compound or pharmaceutical composition into a unit dosage form for administration. Pharmaceutically acceptable excipients are known in the pharmaceutical arts and are disclosed, for example, in Remington: The Science and Practice of Pharmacy, 21st Ed. (Lippincott Williams & Wilkins, Baltimore, Md., 2005). As will be known to those in the art, pharmaceutically acceptable excipients can provide a variety of functions and can be described as wetting agents, buffering agents, suspending agents, lubricating agents, emulsifiers, disintegrants, absorbents, preservatives, surfactants, colorants, flavorants, and sweeteners.

In the present disclosure, the term "halo" or "halogen" as used by itself or as part of another group refers to —Cl, —F, —Br, or —I. In one embodiment, the halo is —Cl or —F. In one embodiment, the halo is —Cl.

In the present disclosure, the term "nitro" as used by itself or as part of another group refers to —NO$_2$.

In the present disclosure, the term "cyano" as used by itself or as part of another group refers to —CN.

In the present disclosure, the term "hydroxy" as used by itself or as part of another group refers to —OH.

In the present disclosure, the term "alkyl" as used by itself or as part of another group refers to unsubstituted straight- or branched-chain aliphatic hydrocarbons containing from one to twelve carbon atoms, i.e., $C_{1-12}$ alkyl, or the number of carbon atoms designated, e.g., a $C_1$ alkyl such as methyl, a $C_2$ alkyl such as ethyl, a $C_3$ alkyl such as propyl or isopropyl, a $C_{1-3}$ alkyl such as methyl, ethyl, propyl, or isopropyl, and so on. In one embodiment, the alkyl is a $C_{1-10}$ alkyl. In another embodiment, the alkyl is a $C_{1-6}$ alkyl. In another embodiment, the alkyl is a $C_{1-4}$ alkyl. In another embodiment, the alkyl is a straight chain $C_{1-10}$ alkyl. In another embodiment, the alkyl is a branched chain $C_{3-10}$ alkyl. In another embodiment, the alkyl is a straight chain $C_{1-6}$ alkyl. In another embodiment, the alkyl is a branched chain $C_{3-6}$ alkyl. In another embodiment, the alkyl is a straight chain $C_{1-4}$ alkyl. In another embodiment, the alkyl is a branched chain $C_{3-4}$ alkyl. In another embodiment, the alkyl is a straight or branched chain $C_{3-4}$ alkyl. Non-limiting exemplary $C_{1-10}$ alkyl groups include methyl, ethyl, propyl, isopropyl, butyl, sec-butyl, tert-butyl, iso-butyl, 3-pentyl, hexyl, heptyl, octyl, nonyl, and decyl. Non-limiting exemplary $C_{1-4}$ alkyl groups include methyl, ethyl, propyl, isopropyl, butyl, sec-butyl, tert-butyl, and iso-butyl.

In the present disclosure, the term "cycloalkyl" as used by itself or as part of another group refers to saturated and partially unsaturated (containing one or two double bonds) cyclic aliphatic hydrocarbons containing one to three rings having from three to twelve carbon atoms, i.e., $C_{3-12}$ cycloalkyl. or the number of carbons designated. In one embodiment, the cycloalkyl group has two rings. In one embodiment, the cycloalkyl group has one ring. In another embodiment, the cycloalkyl group is chosen from a $C_{3-8}$ cycloalkyl group. In another embodiment, the cycloalkyl group is chosen from a $C_{3-6}$ cycloalkyl group. Non-limiting exemplary cycloalkyl groups include cyclopropyl, cyclobutyl, cyclopentyl, cyclohexyl, cycloheptyl, cyclooctyl, norbornyl, decalin, adamantyl, cyclohexenyl, and cyclopentenyl, cyclohexenyl.

In the present disclosure, the term "alkenyl" as used by itself or as part of another group refers to an alkyl group as defined above containing one, two or three carbon-to-carbon double bonds. In one embodiment, the alkenyl group is chosen from a $C_{2-6}$ alkenyl group. In another embodiment, the alkenyl group is chosen from a $C_{2-4}$ alkenyl group. Non-limiting exemplary alkenyl groups include ethenyl, propenyl, isopropenyl, butenyl, sec-butenyl, pentenyl, and hexenyl.

In the present disclosure, the term "alkynyl" as used by itself or as part of another group refers to an alkyl group as defined above containing one to three carbon-to-carbon triple bonds. In one embodiment, the alkynyl has one carbon-to-carbon triple bond. In one embodiment, the alkynyl group is chosen from a $C_{2-6}$ alkynyl group. In another embodiment, the alkynyl group is chosen from a $C_{2-4}$ alkynyl group. Non-limiting exemplary alkynyl groups include ethynyl, propynyl, butynyl, 2-butynyl, pentynyl, and hexynyl groups.

In the present disclosure, the term "haloalkyl" as used by itself or as part of another group refers to an alkyl group substituted by one or more fluorine, chlorine, bromine and/or iodine atoms. In one embodiment, the alkyl group is substituted by one, two, or three fluorine and/or chlorine atoms. In another embodiment, the haloalkyl group is a $C_{1-6}$ haloalkyl group In another embodiment, the haloalkyl group is a $C_{1-4}$ haloalkyl group. Non-limiting exemplary haloalkyl groups include fluoromethyl, 2-fluoroethyl, difluoromethyl, trifluoromethyl, pentafluoroethyl, 1,1-difluoroethyl, 2,2-difluoroethyl, 2,2,2-trifluoroethyl, 3,3,3-trifluoropropyl, 4,4,4-trifluorobutyl, and trichloromethyl groups.

In the present disclosure, the term "alkoxy" as used by itself or as part of another group refers to an optionally substituted alkyl, optionally substituted cycloalkyl, optionally substituted alkenyl or optionally substituted alkynyl attached to a terminal oxygen atom. In one embodiment, the alkoxy group is chosen from a $C_{1-4}$ alkoxy group. In another embodiment, the alkoxy group is chosen from a $C_{1-6}$ alkoxy group. In another embodiment, the alkoxy group is chosen from a $C_{1-4}$ alkyl attached to a terminal oxygen atom, e.g., methoxy, ethoxy, and tert-butoxy.

In the present disclosure, the term "haloalkoxy" as used by itself or as part of another group refers to a $C_{1-4}$ haloalkyl attached to a terminal oxygen atom. Non-limiting exemplary haloalkoxy groups include fluoromethoxy, difluoromethoxy, trifluoromethoxy, and 2,2,2-trifluoroethoxy.

In the present disclosure, the term "aryl" as used by itself or as part of another group refers to a monocyclic, bicyclic, or tricyclic aromatic ring system having from six to fourteen carbon atoms, i.e., $C_6-C_{14}$ aryl. Non-limiting exemplary aryl groups include phenyl (abbreviated as "Ph"), 1-naphthyl, 2-naphthyl, phenanthryl, anthracyl, indenyl, azulenyl, biphenyl, biphenylenyl, and fluorenyl groups. In one embodiment, the aryl group is chosen from phenyl, 1-naphthyl, or 2-naphthyl. In one embodiment, the aryl is a bicyclic or tricyclic $C_{10}-C_{14}$ aromatic ring system.

In the present disclosure, the term "optionally substituted aryl" as used herein by itself or as part of another group means that the aryl as defined above is either unsubstituted or substituted with one to five substituents independently selected from the group consisting of halogen, hydroxy, nitro, cyano, —$SCH_3$, —$SCF_3$, —$NR^{10}R^{11}$, —$C(=O)NR^{10}R^{11}$, —$C(=O)R^{13}$, $C_{1-6}$ alkyl, $C_{2-6}$ alkenyl, $C_{2-6}$ alkynyl, $C_{1-6}$ alkoxy, $C_{1-6}$ haloalkyl, haloalkoxy, optionally substituted $C_{3-12}$ cycloalkyl, optionally substituted $C_6-C_{14}$ aryl, optionally substituted 5- to 14-membered heteroaryl, and optionally substituted 3- to 14-membered heterocyclic ring, wherein $R^{10}$ and $R^{11}$ are independently selected from the group consisting of hydrogen and $C_{1-6}$ alkyl; or $R^{10}$ and $R^{11}$ taken together with the nitrogen atom to which they are attached form a 3- to 12-membered heterocyclic ring; and $R^{13}$ is $C_{1-4}$ alkyl.

In one embodiment, the optionally substituted aryl is an optionally substituted phenyl. In one embodiment, the optionally substituted phenyl has four substituents. In another embodiment, the optionally substituted phenyl has three substituents. In another embodiment, the optionally substituted phenyl has two substituents. In another embodiment, the optionally substituted phenyl has one substituent. Non-limiting exemplary substituted aryl groups include 2-methylphenyl, 2-methoxyphenyl, 2-fluorophenyl, 2-chlorophenyl, 2-bromophenyl, 3-methylphenyl, 3-methoxyphenyl, 3-fluorophenyl, 3-chlorophenyl, 4-methylphenyl, 4-ethylphenyl, 4-methoxyphenyl, 4-fluorophenyl, 4-chlorophenyl, 2,6-di-fluorophenyl, 2,6-di-chlorophenyl, 2-methyl,3-methoxyphenyl, 2-ethyl,3-methoxyphenyl, 3,4-di-methoxyphenyl, 3,5-di-fluorophenyl, 3,4-di-chlorophenyl, 3,5-di-methylphenyl, 3,5-dimethoxy, 4-methylphenyl, 2-fluoro-3-chlorophenyl, and 3-chloro-4-fluorophenyl. The term optionally substituted aryl is meant to include groups having fused optionally substituted cycloalkyl and fused optionally substituted heterocyclic rings. Non-limiting examples include:

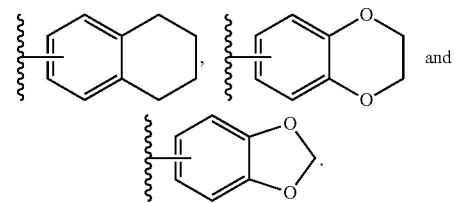

The structure-activity relationships (SAR) of fosmidomycin and FR900098 as inhibitors of several DXR homologs, as well as various microbial pathogens were evaluated. San Jose et al., ACS Infectious Diseases 2016, 2, 923-935. Fosmidomcyin binds to DXR competitively with substrate DOXP and noncompetitively with cofactor NADPH. SAR studies on fosmidomycin analogs reveal that the retro-hydroxamate or hydroxamate moiety should be retained to mimic the crucial interaction of fosmidomycin with the divalent metal cation. Similarly, the phosphonate moiety should be retained as it forms numerous hydrogen bonds with neighboring amino acid residues. A three carbon linker between the two moieties is also found to be crucial for DXR inhibition. The unsaturated FR900098 analog (Scheme 2, 2) gained a two-fold increase in potency against Mtb DXR ($IC_{50}$=1.07 µM) compared with parent compound FR900098. A prodrug strategy was applied to this structure, and the corresponding pivaloyloxymethyl (POM) phosphonate was synthesized (Scheme 2, 3). Compound 3 displays an Mtb MIC$_{99}$ value of 9.4 μg/mL, thus gaining the needed lipophilicity to penetrate the Mtb cell wall. This compound likely regenerates 2 inside the bacteria, and this acid inhibits DXR. Prodrug 3 also shows potent inhibition against P. falciparum growth with an IC$_{50}$ value of 18.3 nM, only slightly less potent than artemisinin (P. falciparum IC$_{50}$=10.4 nM), a current first-line antimalarial drug. Prodrug 3 also displays potent in vivo antimalarial activity.

Scheme 2

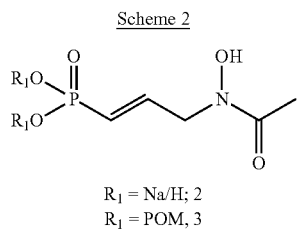

R$_1$ = Na/H; 2
R$_1$ = POM, 3

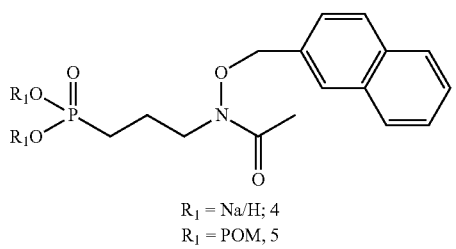

R$_1$ = Na/H; 4
R$_1$ = POM, 5

Analogs with extensioned aromatic groups on the N-alkoxy group of FR900098 were developed as improved DXR inhibitors (Scheme 2, 4, 5). Bjorkelid et al., *Acta Crystallographica Section D* 2012, 68, 134-143. These compounds are designed to act as bisubstrate inhibitors that could bind to both the DOXP and NADPH binding sites. The binding mode of compound 4 was then determined using classical Lineweaver-Burke double reciprocal plots. These experiments showed that compound 4 is competitive with DOXP and NADPH, confirming bisubstrate binding behavior. The POM prodrug of 4 was also synthesized (Scheme 2, 5), showing effective Mtb growth inhibition (MIC$_{99}$=18.75 μg/mL). The bisubstrate strategy increases the overall lipophilicity of the analogs, which is likely beneficial for penetration into several pathogens. Dxr inhibitors are described in U.S. Pat. No. 9,593,136 and WO 2017/127805 A1, both of which are incorporated herein by reference in their entirety.

The present disclosure provides a series of α,β-unsaturated N-acyl (e.g., Scheme 3, A) and N-alkoxy (e.g., Scheme 3, B) fosmidomycin analogs as antimicrobial agents that work via DXR inhibition.

Scheme 3

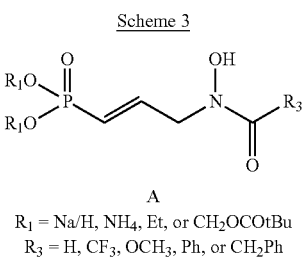

A
R$_1$ = Na/H, NH$_4$, Et, or CH$_2$OCOtBu
R$_3$ = H, CF$_3$, OCH$_3$, Ph, or CH$_2$Ph

-continued

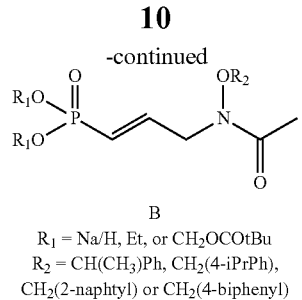

B
R$_1$ = Na/H, Et, or CH$_2$OCOtBu
R$_2$ = CH(CH$_3$)Ph, CH$_2$(4-iPrPh),
CH$_2$(2-naphtyl) or CH$_2$(4-biphenyl)

The present disclosure relates to a compound having the chemical structure of Formula (I):

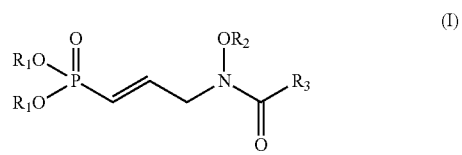

(I)

or a pharmaceutically acceptable salt or prodrug thereof, wherein each R$_1$ is independently H, C$_{1-6}$ alkyl, C$_{1-6}$ haloalkyl, C$_{3-6}$ cycloalkyl, (CR$^a$R$^b$)$_m$-aryl, (CR$^a$R$^b$)$_m$—O(C=O)—C$_{1-6}$ alkyl, (CR$^a$R$^b$)$_m$—O(C=O)—C$_{3-6}$ cycloalkyl, (CR$^a$R$^b$)$_m$—O(C=O)-aryl, (CR$^a$R$^b$)$_m$—O(C=O)O—C$_{1-6}$ alkyl, (CR$^a$R$^b$)$_m$—O(C=O)O—C$_{3-6}$ cycloalkyl, wherein the atom at the left is attached to the oxygen atom; or two R$_1$ taken together with the oxygen atoms and the phosphorus atom to form a 5- to 6-membered optionally substituted ring;

R$_2$ is H or (CR$^c$R$^d$)$_n$-aryl, wherein the atom at the left is attached to the oxygen atom;

R$_3$ is H, C$_{1-6}$ alkyl, C$_{1-6}$ haloalkyl, C$_{3-6}$ cycloalkyl, C$_{1-6}$ alkoxy, C$_{1-6}$ haloalkoxy, C$_{3-6}$ cycloalkoxy, or (CR$^e$R$^f$)$_p$-aryl;

each R$^a$, R$^b$, R$^c$, R$^d$, R$^e$, and R$^f$ is independently H, halogen, methyl, or ethyl;

m and n is independently 1, 2, 3, or 4;

p is 0, 1, 2, 3, or 4;

each aryl is optionally substituted with up to five R$_4$ selected from the group consisting of halogen, hydroxyl, cyano, amino, (C$_{1-6}$ alkyl)amino, di(C$_{1-6}$ alkyl)amino, C$_{1-6}$ alkyl, C$_{1-6}$ haloalkyl, C$_{3-6}$ cycloalkyl, C$_{1-6}$ alkoxy, C$_{1-6}$ haloalkoxy, and C$_{3-6}$ cycloalkoxy;

provided that the compound is not

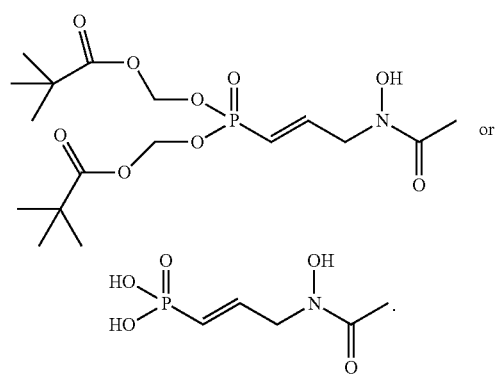

In some embodiments, when each $R_1$ is H, the phosphonic acid moiety can form a salt with a base. In some embodiments, the compound of Formula I has the structure of Formula (II):

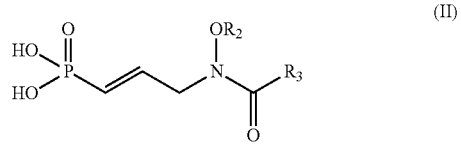

(II)

or a pharmaceutically acceptable salt or prodrug thereof, wherein $R_2$ and $R_3$ are as defined herein, and provided that when $R_2$ is H, $R_3$ is not $CH_3$. In some embodiments, $R_3$ is H. In some embodiments, $R_3$ is phenyl or benzyl.

In some embodiments, the compound is a mono-salt. In some embodiments, the compound is a di-salt.

In some embodiments, the salt is a $Na^+$, $K^+$, or quaternary ammonium salt. In some embodiments, the salt is a $Na^+$ or $NH_4^+$ salt.

In some embodiments, the compound is di-$Na^+$ salt. In some embodiments, the compound is di-$NH_4^+$ salt. In some embodiments, the compound is mono-$Na^+$ salt (H/Na). In some embodiments, the compound is mono-$NH_4^+$ salt (H/$NH_4$).

In some embodiments, each $R_1$ is independently $C_{1-6}$ alkyl, $C_{1-6}$ haloalkyl, $C_{3-6}$ cycloalkyl, $(CR^aR^b)_m$-aryl, $(CR^aR^b)_m$—O(C=O)—$C_{1-6}$ alkyl, $(CR^aR^b)_m$—O(C=O)—$C_{3-6}$ cycloalkyl, $(CR^aR^b)_m$—O(C=O)-aryl, $(CR^aR^b)_m$—O(C=O)O—$C_{1-6}$ alkyl, $(CR^aR^b)_m$—O(C=O)O—$C_{3-6}$ cycloalkyl, wherein the atom at the left is attached to the oxygen atom. In some embodiments, each $R_1$ is the same. In some embodiments, each $R_1$ is different.

In some embodiments, each $R_1$ is $C_{1-6}$ alkyl. In some embodiments, each $R_1$ is $C_{1-3}$ alkyl. In some embodiments, each $R_1$ is methyl or ethyl.

In some embodiments, each $R_1$ is $(CR^aR^b)_m$-aryl. In some embodiments, each $R_1$ is $CH_2$-phenyl (benzyl or Bn).

In some embodiments, each $R_1$ is $(CR^aR^b)_m$—O(C=O)—$C_{1-6}$ alkyl. In some embodiments, each $R_1$ is $CH_2$—O(C=O)—$C_{1-6}$ alkyl. In some embodiments, each $R_1$ is $CH(CH_3)$—O(C=O)—$C_{1-6}$ alkyl. In some embodiments, each $R_1$ is $CH_2$—O(C=O)—$C(CH_3)_3$ (POM).

In some embodiments, the compound of Formula I has the structure of Formula (III):

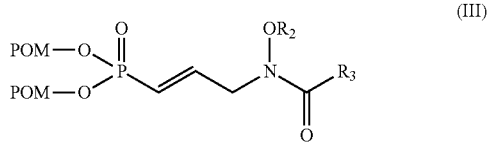

(III)

or a pharmaceutically acceptable salt or prodrug thereof, wherein $R_2$ and $R_3$ are as defined herein and provided when $R_2$ is H, $R_3$ is not $CH_3$. In some embodiments, $R_3$ is H. In some embodiments, $R_3$ is phenyl or benzyl.

In some embodiments, two $R_1$ taken together with the oxygen atoms and the phosphorus atom to form a 5- to 6-membered optionally substituted ring. Examples of the 5- or 6-membered ring include:

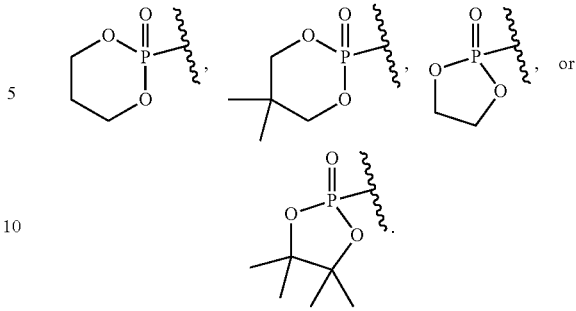

In some embodiments, $R_2$ is H or $(CR^cR^d)_n$-aryl, wherein the atom at the left is attached to the oxygen atom.

In some embodiments, $R_2$ is H.

In some embodiments, $R_2$ is $(CR^cR^d)_n$-aryl, wherein aryl is an optionally substituted phenyl, biphenyl, or naphthyl. In some embodiments, $R_2$ is $(CH_2)_n$-aryl. In some embodiments, $R_2$ is $CH_2$-aryl. In some embodiments, $R_2$ is $CH(CH_3)$-aryl.

In some embodiments, n is 1, 2, or 3. In some embodiments, n is 1 or 2. In some embodiments, n is 1.

In some embodiments, the aryl group in $R_2$ is phenyl optionally substituted with up to five $R_4$.

In some embodiments, $R_4$ is selected from the group consisting of halogen, hydroxyl, cyano, amino, ($C_{1-6}$ alkyl) amino, di($C_{1-6}$ alkyl)amino, $C_{1-6}$ alkyl, $C_{1-6}$ haloalkyl, $C_{3-6}$ cycloalkyl, $C_{1-6}$ alkoxy, $C_{1-6}$ haloalkoxy, and $C_{3-6}$ cycloalkoxy. In some embodiments, $R_4$ is halogen, cyano, $CF_3$, methyl, ethyl, n-propyl, isopropyl, methoxy, ethoxy, n-propoxyl, or isopropoxyl.

In some embodiments, the aryl group in $R_2$ is phenyl without a substituent. In some embodiments, the aryl group in $R_2$ is phenyl substituted with one $R_4$ at para-position.

In some embodiments, the aryl group in $R_2$ is naphthyl optionally substituted with up to five $R_4$. In some embodiments, the aryl group in $R_2$ is 1-naphthyl. In some embodiments, the aryl group in $R_2$ is 2-naphthyl.

In some embodiments, $R_3$ is H, $C_{1-3}$ alkyl, $C_{1-3}$ haloalkyl, $C_{1-3}$ alkoxy, or $C_{1-3}$ haloalkoxy. In some embodiments, $R_3$ is H.

In some embodiments, $R_3$ is $C_{1-3}$ alkyl. In some embodiments, $R_3$ is $CH_3$.

In some embodiments, $R_3$ is $C_{1-3}$ haloalkyl. In some embodiments, $R_3$ is $OCH_3$.

In some embodiments, $R_3$ is $C_{1-3}$ haloalkyl. In some embodiments, $R_3$ is $CF_3$.

In some embodiments, $R_3$ is H, $CH_3$, $CF_3$, or $OCH_3$.

In some embodiments, $R_3$ is $(CH_2)_p$-aryl, wherein p is 0, 1, 2, or 3. In some embodiments, $R_3$ is phenyl. In some embodiments, $R_3$ is benzyl.

In some embodiments, the compound of Formula I is

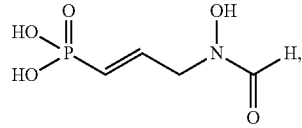

or a pharmaceutically acceptable salt or prodrug thereof. In some embodiments, the compound is a $Na^+$ or $NH_4^+$ salt of this compound. In some embodiments, the compound is a Na⁺ salt. In some embodiments, the compound is an NH₄⁺ salt. In some embodiments, the compound is a prodrug of this compound.

In some embodiments, the compound of Formula I is

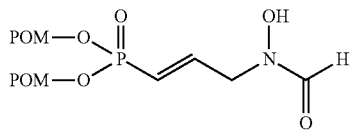

or a prodrug thereof.

In some embodiments, the compound of the present disclosure is not

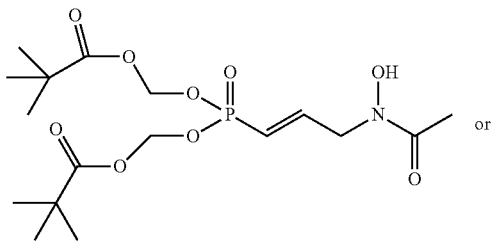

In some embodiments, the compound of the present disclosure is not

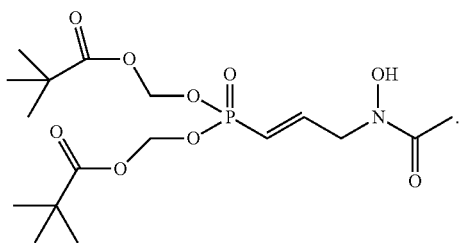 [SMILES: CC(=O)N(O)C/C=C/P(=O)(OCOC(=O)C(C)(C)C)OCOC(=O)C(C)(C)C]

In some embodiments, the compound of the present disclosure is not

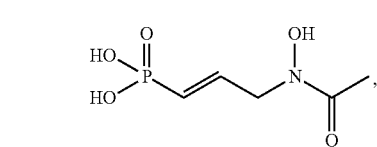

or a mono-Na⁺ salt (Na/H) thereof.

In some embodiments, the compound of the present disclosure is

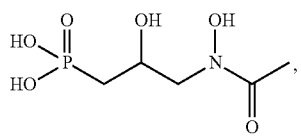

or a stereoisomer thereof, or a pharmaceutically acceptable salt thereof.

In some embodiments, the compound of the present disclosure is

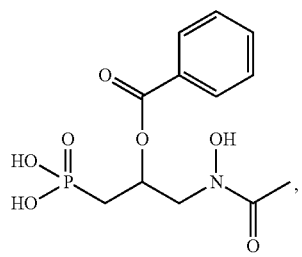 [SMILES: CC(=O)N(O)CC(CP(=O)(O)O)OC(=O)c1ccccc1]

or a stereoisomer thereof, or a pharmaceutically acceptable salt thereof.

Examples of the compounds of the present disclosure include, but not limited to the compounds listed in Table 1, and the pharmaceutically acceptable salts and prodrugs thereof.

TABLE 1

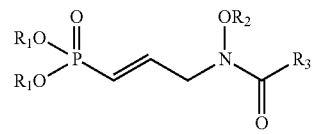

| Compound | $R_1$ | $R_2$ | $R_3$ |
|---|---|---|---|
| 11a | Et | H | H |
| 11b | Et | H | $CF_3$ |
| 11c | Et | H | $OCH_3$ |
| 12a | Na/H | H | H |
| 12b | Na/H | H | $CF_3$ |
| 12c | $NH_4$ | H | $OCH_3$ |
| 15d | Et | $CH(CH_3)Ph$ | $CH_3$ |
| 15e | Et | $CH_2(4\text{-iprPh})$ | $CH_3$ |
| 15f | Et | $CH_2(2\text{-naphthyl})$ | $CH_3$ |
| 15g | Et | $CH_2(4\text{-biphenyl})$ | $CH_3$ |
| 16d | Na/H | $CH(CH_3)Ph$ | $CH_3$ |
| 16e | Na/H | $CH_2(4\text{-iprPh})$ | $CH_3$ |
| 16f | Na/H | $CH_2(2\text{-naphthyl})$ | $CH_3$ |
| 16g | Na/H | $CH_2(4\text{-biphenyl})$ | $CH_3$ |
| 18a | POM | H | H |
| 18b | POM | H | $CF_3$ |
| 18c | POM | H | $OCH_3$ |
| 19e | POM | $CH_2(4\text{-iprPh})$ | $CH_3$ |
| 19f | POM | $CH_2(2\text{-naphthyl})$ | $CH_3$ |
| 19g | POM | $CH_2(4\text{-biphenyl})$ | $CH_3$ |
| 30 | Na/H | H | Ph |
| 31a | Et | H | Ph |
| 31b | Et | H | $CH_2Ph$ |
| 31c | Et | H | $(CH_2)_2Ph$ |
| 31d | Et | H | $(CH_2)_3Ph$ |
| 32a | Na/H | H | Ph |
| 32b | Na/H | H | $CH_2Ph$ |
| 32c | Na/H | H | $(CH_2)_2Ph$ |
| 32d | Na/H | H | $(CH_2)_3Ph$ |
| 33a | POM | H | Ph |
| 33b | POM | H | $CH_2Ph$ |

TABLE 1-continued

| Compound | R₁ | R₂ | R₃ |
|---|---|---|---|
| 33c | POM | H | (CH₂)₂Ph |
| 33d | POM | H | (CH₂)₃Ph |

The present disclosure also provides a pharmaceutical composition comprising the compound disclosed herein and a pharmaceutically acceptable excipient.

The present disclosure further provides a method for treating or preventing a microbial infection in a subject in need thereof comprising administering to the subject an effective amount of the compound disclosed herein.

In some embodiments, the microbial infection is malaria. In some embodiments, the microbial infection is tuberculosis.

EXAMPLES

Example 1. Synthesis

N-acyl analogs 12a-c were prepared in 7 steps from commercially available starting materials shown in Scheme 4. First, allyl phosphonate 6 was synthesized from triethylphosphite and allyl bromide via a Michaelis-Arbuzov reaction. Subsequent addition of bromine to compound 6 resulted in production of dibromide 7. O-Benzylhydroxylamine hydrochloride was neutralized in situ and protected using di-tert-butyldicarbonate to yield Boc-protected 8, which was then reacted with compound 7 and two equivalents of NaH to prepare compound 9. The first equivalent of NaH deprotonated 8 and generated a nucleophile to attack the primary bromide of compound 7. The second equivalent of NaH was used to eliminate the β-bromide to furnish α,β-unsaturated phosphonate 9. Under acidic conditions, compound 9 was hydrolyzed and generated the deprotected amine in situ that acted as a building block to be acylated with an acyl chloride or anhydride to synthesize N-acyl intermediates 10b-c. For compound 10a, the electrophilic reagent N-formylimidazole was prepared using formic acid and 1,1'-carbonyldiimidazole. Removal of the benzyl group using BCl₃ yielded retro-hydroxamic acids 11a-c. Treatment of these acids with TMSBr, followed by either NaOH or NH₃ gave monosodium salts 12a-b or diammonium salt 12c, respectively. In the case of 11c, synthesis of the sodium salt resulted in an unstable compound, and thus the ammonium salt was made.

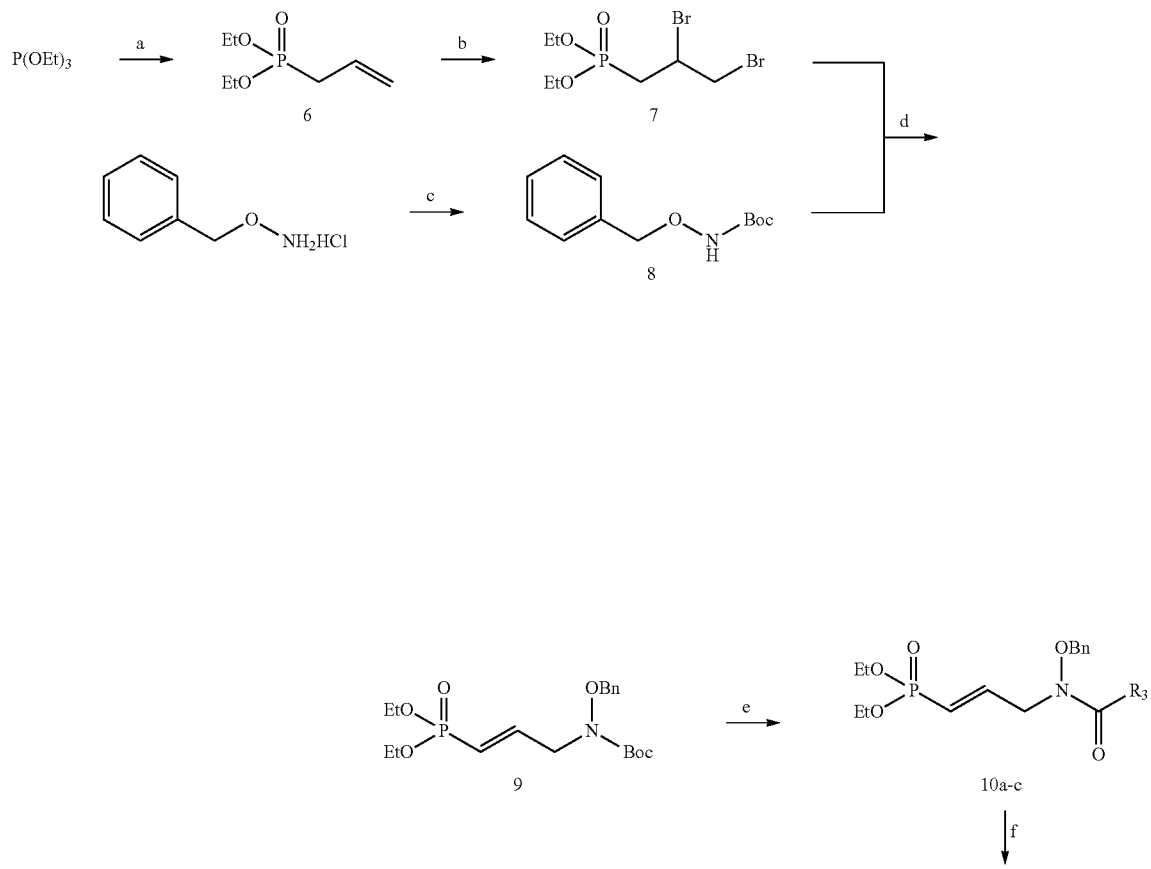

Scheme 4. Synthesis of N-acyl analogs 11a-c, 12a-c.

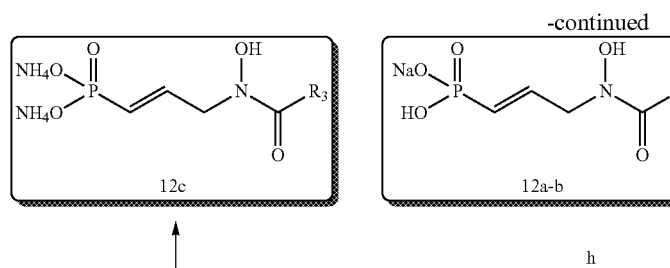
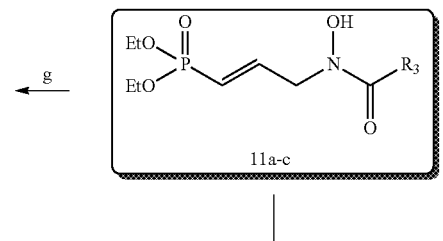

a: $R_3 = H$
b: $R_3 = CF_3$
c: $R_3 = OCH_3$

Reagents and conditions: a) Allyl bromide, 60° C., 2 days; b) $Br_2$, $CH_2Cl_2$, 0° C. to rt, 2 h; c) $Boc_2O$, TEA, $H_2O$, THF, rt, 2.5 h; d) NaH, NaI, THF, 0° C. to rt, 20 h; e) i. AcCl, MeOH, rt, 30 min; ii. $Na_2CO_3$, RCOCl or $(RCO)_2O$, 0° C. to rt, 30 min to 24 h (10a: $Na_2CO_3$, HCOOH, 1,1'-Carbonyldiimidazole, 0° C., 30 min); f) $BCl_3$, $CH_2Cl_2$, -70° C., 30 min to 3 h; g) i. TMSBr, $CH_2Cl_2$, 0° C. to rt, 24 h; ii. NaOH, $H_2O$, rt, 1 h; h) i. TMSBr, $CH_2Cl_2$, 0° C. to rt, 24 h; ii. $NH_4OH$, $H_2O$, rt, 1 h.

Scheme 5 shows the 4-step synthesis used to prepare the N-alkoxy analogs, starting from intermediate 9. Acetyl chloride was used to synthesize compound 13 following the method described above. Subsequent debenzylation of 13 by $BCl_3$ generated 14, the diethyl ester of FR900098. This compound acted as a core intermediate from which to synthesize the series of the N-alkoxy analogs. The synthesis of 15d-g was initially attempted using Williamson ether synthesis with either NaH or sodium tert-butoxide in polar solvents such as THF and DMF. Unfortunately, these reactions failed because of the instability of 14 in the presence of such harsh bases. Weaker bases, such as $Na_2CO_3$ or $Et_3N$, were then applied to the reaction, and yet an overwhelming amount of side products were generated concomitantly, possibly due to the high polarity of the solvents. The reaction conditions were optimized using $Na_2CO_3$ with $CH_2Cl_2$ as a relatively non-polar solvent. The reaction was carried out in a sealed tube and heated at 60° C. for 48 hours to yield 15d-g, which were then converted to monosodium salts 16d-g in a manner similar to the synthesis of 12a-c.

Scheme 5. Synthesis of N-hydroxyl analogs 15d-g, 16d-g.

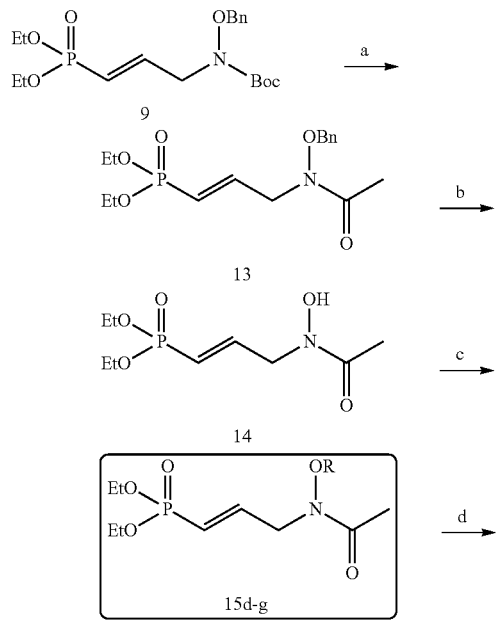
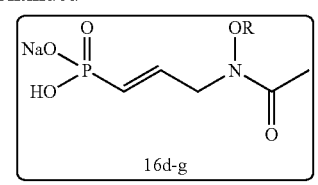

d: $R = CH(CH_3)Ph$
e: $R = CH_2(4\text{-iprPh})$
f: $R = CH_2(2\text{-naphthyl})$
g: $R = CH_2(4\text{-biphenyl})$ Reagents and conditions: a) i. AcCl, MeOH, rt, 30 min; ii. $Na_2CO_3$, $CH_3COCl$, 0° C. to rt, 24 h; b) $BCl_3$, $CH_2Cl_2$, -70° C., 30 min to 3 h; c) $R'CH_2Br$ or $R'CH(CH_3)Br$, $Na_2CO_3$, NaI, $CH_2Cl_2$, 60° C., 2 days; d) i. TMSBr, $CH_2Cl_2$, 0° C. to rt, 24 h; ii. NaOH, $H_2O$, rt, 1 h.

The prodrugs of selected analogs were made (Scheme 6). To obtain the diPOM esters for N-acyl analogs (17a-c), compounds 10a-c were treated with TMSBr and reprotected with POM chloride and $Et_3N$. Due to the low yield of 17b, only 17a and 17c were carried to the next reaction. Removal of the benzyl group using $BCl_3$ gave the diPOM prodrugs 18a, c. Similarly, the diPOM esters of N-alkoxy analogs 19e-g were prepared from 16e-g via treatment with POM chloride and $Et_3N$.

Scheme 6. Synthesis of POM prodrugs 18a, c and 19e-g.

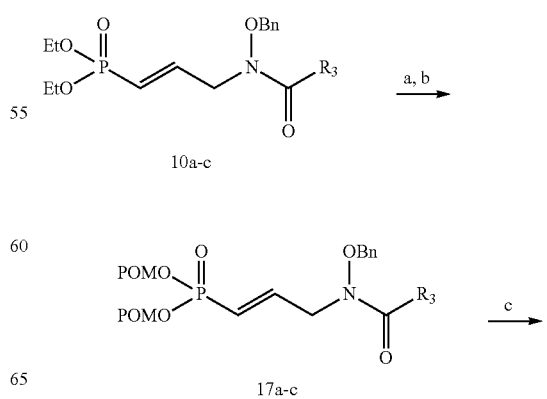

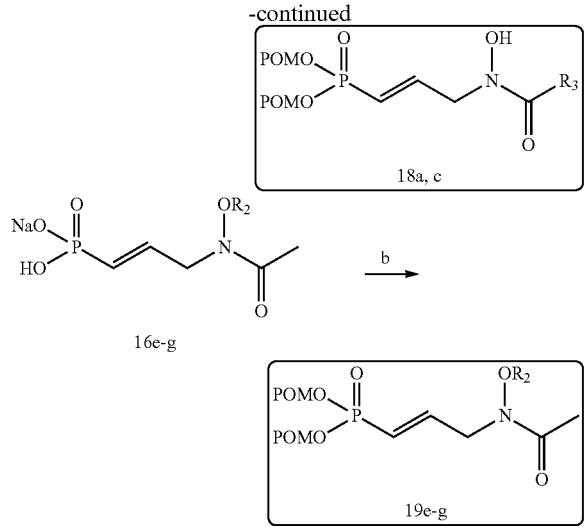

a: $R_3$ = H
b: $R_3$ = $CF_3$
c: $R_3$ = $OCH_3$ e: $R_2$ = $CH_2$(4-iprPh)
f: $R_2$ = $CH_2$(2-naphthyl)
g: $R_2$ = $CH_2$(4-biphenyl)

Reagents and conditions: a) i. TMSBr, $CH_2Cl_2$, 0° C. to rt, 24 h; ii. NaOH, $H_2O$, rt, 1 h. b) Chloromethylpivalate, TEA, NaI, DMF, 60° C., 24 h; c) $BCl_3$, $CH_2Cl_2$, -70° C., 30 min to 3 h.

Because of the low yields of N-acyl analog 18b (overall yield 2.1%) and 17b (overall yield 0.42%), an optimized synthesis for N-acyl prodrugs was developed (Scheme 7). This route to synthesize diPOM esters was brought forward since compound 6 could react for a longer time due to its reasonable stability. This allowed to achieve a higher yield (compound 20, yield 52%) and reduced the overall synthetic attrition by conducting this arduous reaction only once, compared with the previous route that the diPOM esterification of every N-acyl analog has to be performed individually. Bromine addition of the resulting product 20 yielded dibromide 21. Because of the instability of the POM group under acidic conditions, the use of Boc-protected O-benzyl-hydroxylamine was insufficient (due to its required deprotection conditions). Thus, free amine 23 was prepared to react with mono-bromide 22, the eliminated product from 21 and NaH, to yield 24. This conversion enabled a variety of diPOM N-acyl analogs. Compound 24 was converted to acylated compounds 17a and 17b, with the latter compound obtained in a 17-fold increase in yield (overall yield 7.0%) versus the previous synthetic route (overall yield 0.42%). The final N-acyl prodrugs 18a (overall yield 3.9%) and 18b were subsequently obtained via a debenzylation reaction as in Scheme 7.

Scheme 7. Optimized synthesis of N-acyl analog prodrugs 18a-b.

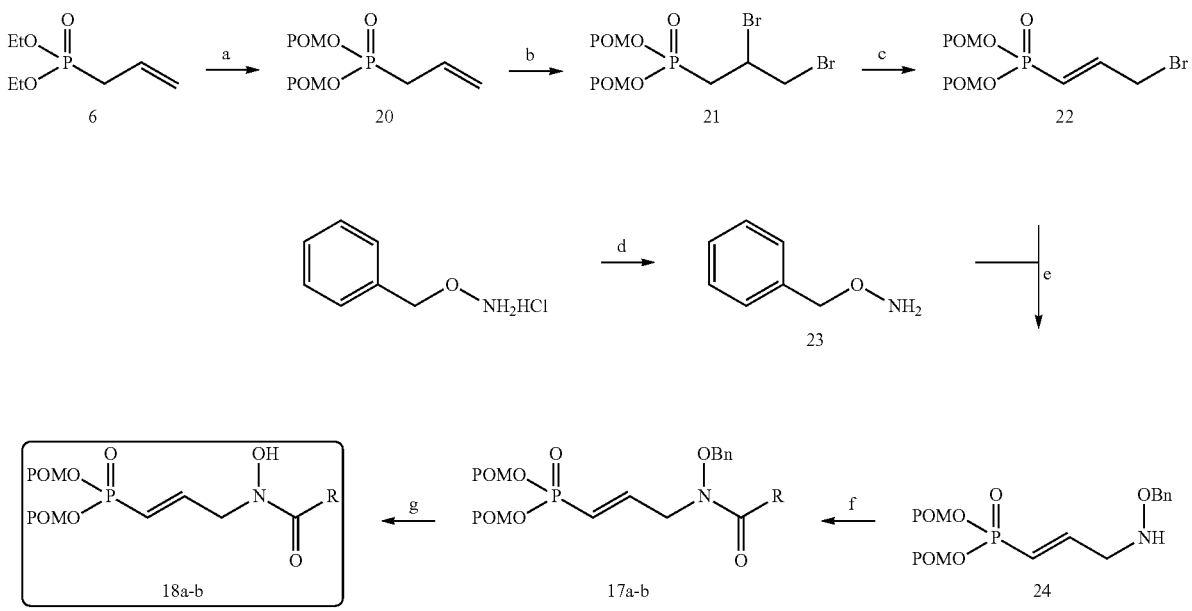

a: R = H
b: R = $CF_3$

Reagents and conditions: a) i. TMSBr, $CH_2Cl_2$, 0° C. to rt, 24 h; ii. $CH_3OH$, rt, 1 h; iii. Chloromethylpivalate, TEA, NaI, DMF, 60° C., 24 h; b) $Br_2$, $CH_2Cl_2$, 0° C. to rt, 2 h; c) NaH, THF, rt, 24 h; d) NaOH, $Et_2O$, $H_2O$, rt, 30 min; e) TEA, THF, reflux, 3 h; f) TEA, $(CF_3CO)_2O$, 0° C., 30 min or TEA, HCOOH, 1,1'-Carbonyldiimidazole, 0° C., 30 min; g) $BCl_3$, $CH_2Cl_2$, -70° C., 30 min to 3 h.

Similarly, N-acyl analogs 31a-d, 32a-d, and 33a-b,d were prepared according to Scheme 8.

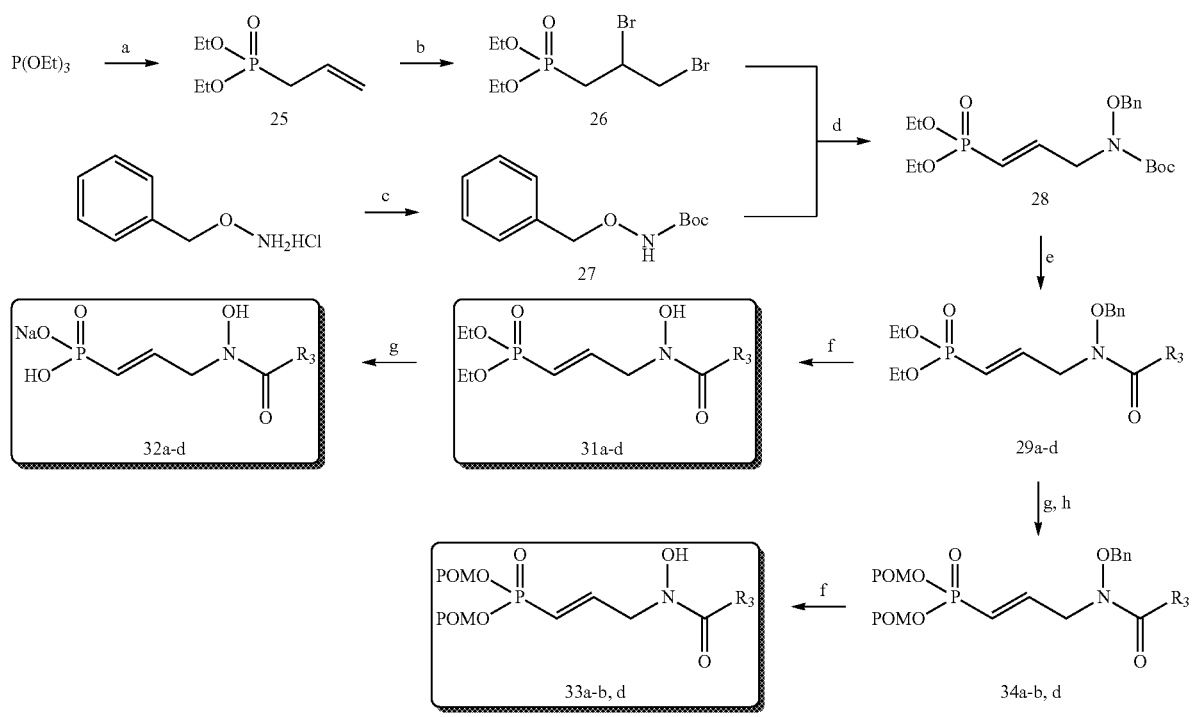

Scheme 8. Synthesis of N-acyl analogs 31a-d, 32a-d, 33a-b, d.

a: $R_3$ = Ph
b: $R_3$ = $CH_2$Ph
c: $R_3$ = $(CH_2)_2$Ph
d: $R_3$ = $(CH_2)_3$Ph

Reagents and conditions: a) Allyl bromide, 60° C., 2 days; b) $Br_2$, $CH_2Cl_2$, 0° C. to rt, 2 h; c) $Boc_2O$, TEA, $H_2O$, THF, rt, 2.5 h; d) NaH, NaI, THF, 0° C. to rt, 20 h; e) i. AcCl, MeOH, rt, 30 min; ii. $Na_2CO_3$, RCOCl, 0° C. to rt, 30 min to 24 h; f) $BCl_3$, $CH_2Cl_2$, -70° C., 30 min to 3 h; g) i. TMSBr, $CH_2Cl_2$, 0° C. to rt, 24 h; ii. NaOH, $H_2O$, rt, 1 h; h) Chloromethylpivalate, TEA, NaI, DMF, 60° C., 24 h.

Example 2. Biological Evaluation

Evaluation of 12a-c, 16d-g as DXR inhibitors.

The phosphonic acid salts were evaluated as inhibitors of DXR from P. falciparum, and the results are shown in Table 2. Initially, the percent remaining enzyme activity was measured by treating the enzyme with each compound at a single concentration of 100 μM. This data shows the intrinsic activity of the compounds. Half-maximal inhibitory concentrations ($IC_{50}$ values) were determined for compounds showing greater than 75% inhibition of DXR.

TABLE 2

Inhibition of P. falciparum DXR by phosphonic acid salts

| Compound | $R_1$ | $R_2$ | $R_3$ | Pf DXR $IC_{50}$ [μM] (% Residue) |
|---|---|---|---|---|
| 2 | Na/H | H | $CH_3$ | 0.018[a] |
| 12a | Na/H | H | H | 0.092 |
| 12b | Na/H | H | $CF_3$ | (36.96) |
| 12c | $NH_4$ | H | $OCH_3$ | 14.45 |
| 16d | Na/H | $CH(CH_3)$Ph | $CH_3$ | 2.54 |
| 16e | Na/H | $CH_2$(4-iprPh) | $CH_3$ | 2.11 |

TABLE 2-continued

Inhibition of P. falciparum DXR by phosphonic acid salts

| Compound | $R_1$ | $R_2$ | $R_3$ | Pf DXR $IC_{50}$ [μM] (% Residue) |
|---|---|---|---|---|
| 16f | Na/H | $CH_2$(2-naphthyl) | $CH_3$ | (25) |
| 16g | Na/H | $CH_2$(4-biphenyl) | $CH_3$ | 4.53 |

Pf = P. falciparum;
$IC_{50}$ = inhibitory concentration at 50%;
[a]See Gießmann et al., Chemistry & Biodiversity 2008, 5, 643-656.

Of the new compounds, the most potent P. falciparum DXR inhibitor is 12a with an $IC_{50}$ value of 92 nM, only slightly less active than the parent unsaturated compound 2. Within the N-alkoxy series of bisubstrate inhibitors 16d-g, compound 16e (4-iprPh) displays the most potent inhibition of the enzyme with an $IC_{50}$ value of 2.11 μM. Interestingly, the N-alkoxy substituent of 16e was also found among the more active substituents in the saturated series. Compounds 16d and 16g with phenethyl and biphenyl substituents, respectively, were also active against the enzyme, displaying low μM inhibition.

Compounds 12b-c explore the influence of electronics in DXR inhibition, comparing an electron-withdrawing group ($CF_3$, 12b) and electron-donating group ($OCH_3$, 12c) with parent formyl analog 12a and acetyl analog 2. Compounds 12b and 12c display only weak and moderate inhibition of P. falciparum DXR, respectively. This result shows that electronic effects on the N-acyl group do not sway DXR inhibition as neither the $CF_3$ group (12b) or $OCH_3$ group (12c) improved the activity, compared with the $CH_3$ group of 2 which is a potent inhibitor of DXR.

Diethyl phosphonate analogs (11a-c and 15d-g) were also evaluated as inhibitors of DXR from P. falciparum, and the results are shown in Table 3.

TABLE 3

Inhibition of diethyl phosphonate analogs against P. falciparum

| Compound Isoniazid | P.f. $IC_{50}$ [µg/mL] |
|---|---|
| 1 | 0.175 |
| 11a | >100 |
| 11b | >100 |
| 11c | >100 |
| 15d | 23.5 |
| 15e | 21.1 |
| 15f | 29.6 |
| 15g | 13.7 |

In Vitro Effects on Pathogen Growth by 12a-c, 16d-g, 18a-c, 19e-g.

POM prodrugs of selected analogs were synthesized in an effort to improve their cellular activity (and possibly bio-availability). All target compounds were tested for the growth inhibition against P. falciparum following reported procedures (Table 4). This data indicates the inhibitory concentration of compound required to decrease growth of P. falciparum by 50% (Pf $IC_{50}$).

TABLE 4

Growth inhibition of the analogs against P. falciparum

| Compound | $R_1$ | $R_2$ | $R_3$ | Pf $IC_{50}$ [µM] |
|---|---|---|---|---|
| 1a | | | | 0.854 |
| 12a | Na/H | H | H | 0.019 |
| 12b | Na/H | H | $CF_3$ | 113.2 |
| 12c | $NH_4$ | H | $OCH_3$ | 28.6 |
| 16d | Na/H | $CH(CH_3)Ph$ | $CH_3$ | 1.2 |
| 16e | Na/H | $CH_2(4\text{-}iprPh)$ | $CH_3$ | 1.1 |
| 16f | Na/H | $CH_2(2\text{-naphthyl})$ | $CH_3$ | 26.0 |
| 16g | Na/H | $CH_2(4\text{-biphenyl})$ | $CH_3$ | 2.3 |
| 18a | POM | H | H | 0.013 |
| 18b | POM | H | $CF_3$ | 14.2 |
| 18c | POM | H | $OCH_3$ | 23.7 |
| 19e | POM | $CH_2(4\text{-}iprPh)$ | $CH_3$ | 55.1 |
| 19f | POM | $CH_2(2\text{-naphthyl})$ | $CH_3$ | 49.9 |
| 19g | POM | $CH_2(4\text{-biphenyl})$ | $CH_3$ | 43.2 |

Pf = P. falciparum;
$IC_{50}$ = inhibitory concentration at 50%

In Table 4, the polar phosphonic acid salts show significant activity against P. falciparum parasites. Compound 12a is the most active compound of the phosphonate salts, with an activity surpassing that of parent compound (and clinically evaluated candidate) fosmidomycin (1a). The data also shows that the inhibition of P. falciparum growth corresponds well to the activities of these compounds against the enzyme target P. falciparum DXR. Of the salts, compounds 12a and 16e were the most active DXR inhibitors. These salts are also the most active inhibitors of P. falciparum growth.

The cellular activity of the POM prodrugs is also shown in Table 4. As was the case with the phosphonic acid salts, several of the POM prodrugs are highly active against P. falciparum. Of the N-acyl series, compound 12a was the most potent P. falciparum DXR inhibitor. Its prodrug, compound 18a, is the most potent prodrug inhibitor of P. falciparum ($IC_{50}$=13 nM) from the POM series. In the N-alkoxy series of compounds, compound 16e was the most potent DXR inhibitor and also shows the highest potency ($IC_{50}$=1.1 µM) against P. falciparum parasites.

As is evident from the data in Table 4, several compounds show extremely potent antimalarial activity. Fosmidomycin is a modestly potent inhibitor of P. falciparum growth (1a, $IC_{50}$=854 nM). Modification of fosmidomycin with the change of added α,β-unsaturation yields compound 12a as an even more potent P. falciparum inhibitor with an $IC_{50}$ value of 19 nM. Its prodrug 18a also potently inhibits P. falciparum with an $IC_{50}$ value of 13 nM. This value is comparable to the inhibitory activity of current first-line antimalarial drug artemisinin (P. falciparum $IC_{50}$=10.4 nM). The c Log P, Cytotoxicity, and Selective Indices of 12a and 18a.

The computed c Log P, inhibition of HepG2, and selectivity indices (ratio of the antimicrobial activity to the human cell toxicity) for compounds 12a and 18a are shown in Table 5. Compound 12a has a low c Log P value of −5.7. The prodrug strategy significantly increased the lipophilicity of the compound, yielding 18a with a c Log P of 0.89 (an increase of over six orders of magnitude). Neither the phosphonic acid salt 12a nor the prodrug 18a show toxicity against HepG2 cell lines, with $IC_{50}$ values >50 µM. Thus, these compounds have excellent selectivity indices of 2632 and 3846 for 12a and 18a, respectively, against P. falciparum.

Compound 18a is Rapidly Converted to 12a In Vitro and In Vivo.

Compound 18a was designed to be a prodrug for 12a. To determine the rate of hydrolysis by plasma and hepatic esterases, compounds 12a and 18a were incubated in mouse liver microsomes (MLM) and in mouse plasma (Table 5). Compound 12a is stable in plasma ($t_{1/2}$>120 min) and in mouse liver microsomes ($t_{1/2}$>60 min). In contrast, POM prodrug 18a is very rapidly converted to compound 12a in plasma and microsomes ($t_{1/2}$<5 min for both).

TABLE 5

Computed cLogP, Cytotoxicity, and Selectivity Index

| Compound | R | cLogP | HepG2 $IC_{50}$ [µM] | $SI^{Pf}$ | Metabolic stability MLM ($t_{1/2}$) | Plasma stability |
|---|---|---|---|---|---|---|
| 12a | Na/H | −5.7 | >50 | 2632 | >60 min | >120 min |
| 18a | POM | 0.89 | >50 | 3846 | <5 min | <5 min | cLogP calculated by DataWarrior (version 4.6.1. http://www.openmolecules.org/index-.html) ;
$SI^{Pf}$ = Selectivity Index for P. falciparum (HepG2 $IC_{50}$/P.falciparum $IC_{50}$); MLM = mouse liver microsomes Compounds 12a and 18a Inhibit Isoprenoid Synthesis in P. falciparum.

Figure 2:
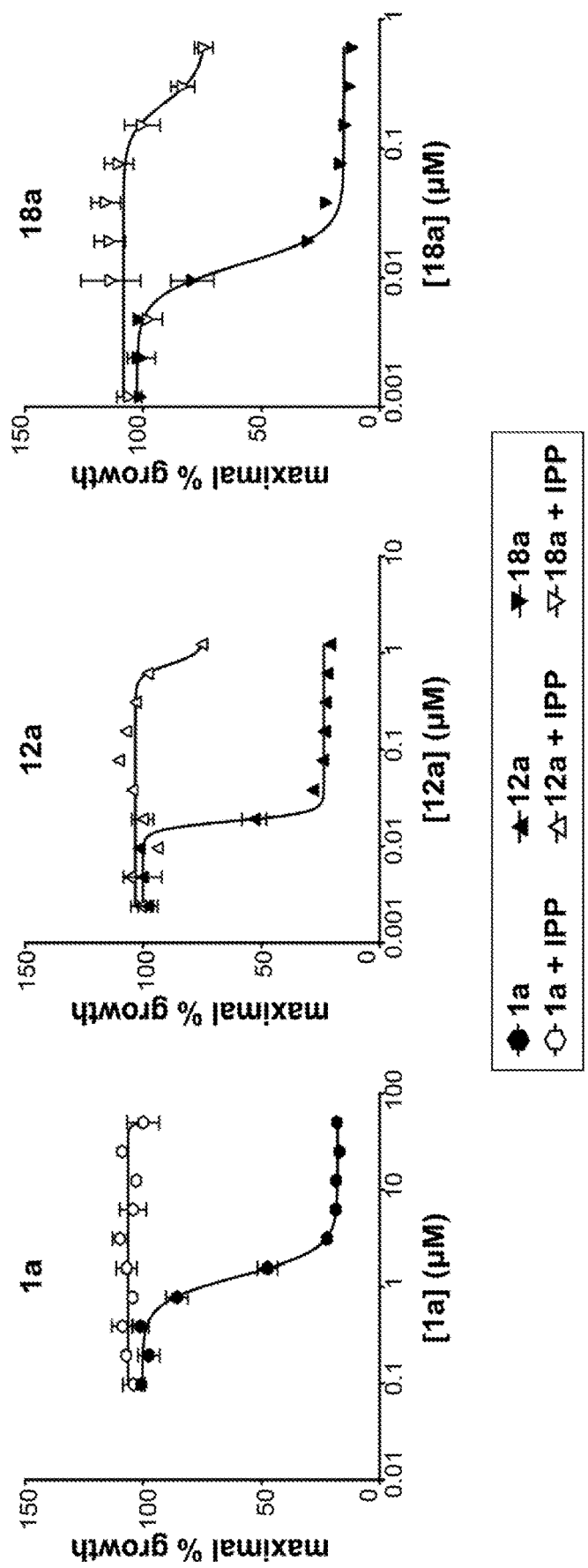
Figure 3:
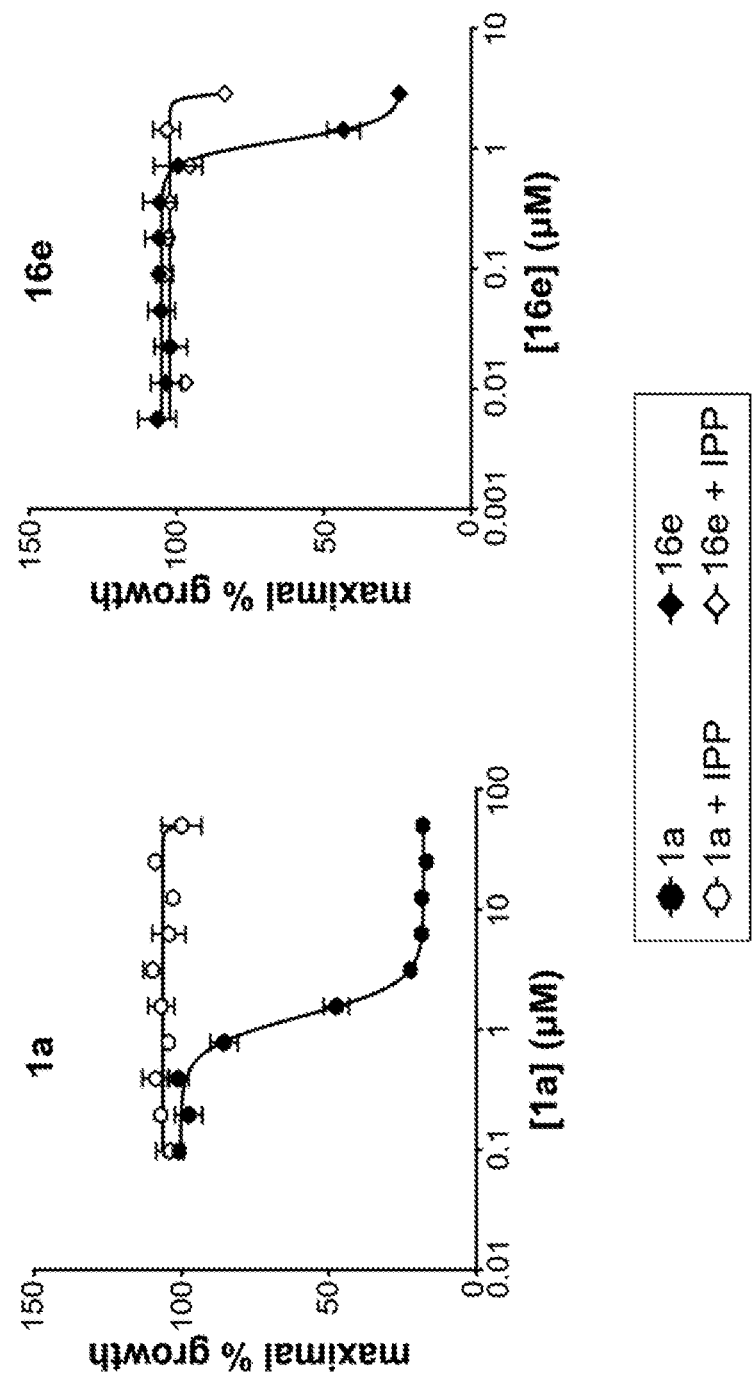
FIG. 3 depicts that P. falciparum growth inhibited by the N-alkoxy analog 16e is restored by IPP supplementation.
Figure 9:
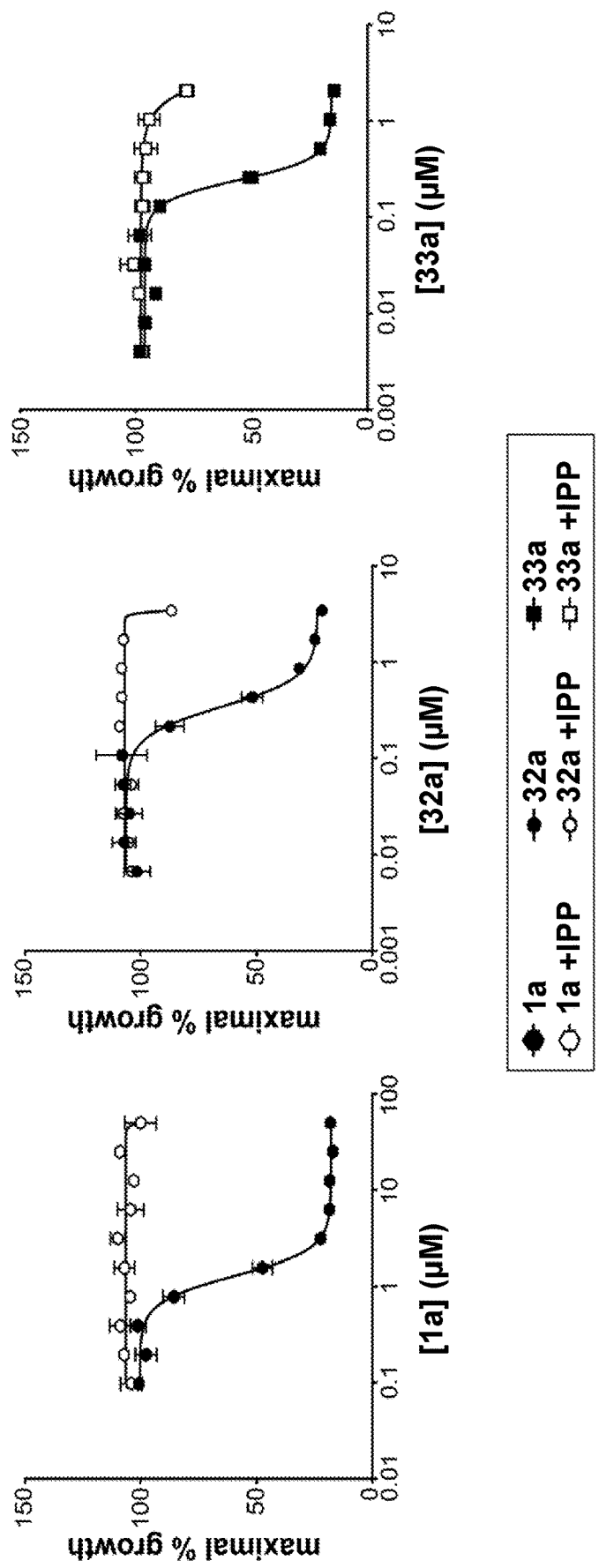

Compounds 12a and 18a were examined in further assays to determine their intracellular mechanism of action. First, one would ask if parasites treated with these inhibitors could be rescued by MEP pathway product IPP supplementation. If the inhibitors target the MEP pathway, parasite growth should be restored if exogenous IPP were added to the growth media. Edwards et al., Scientific Reports 2017, 7, 8400. As is shown in FIG. 2, addition of exogenous IPP effectively rescues growth of P. falciparum treated with 12a or 18a. This pattern is similar to the restoration effect observed in fosmidomycin (1a)-treated parasites supplied with IPP. In the assays, P. falciparum strain 3D7 was treated with inhibitors at a range of concentrations and growth was quantified by PicoGreen (Life Technologies) after 72 h. IPP, the product of the MEP pathway, rescues growth of drug-treated parasites (open shapes) indicating the compounds are specific inhibitors of the MEP pathway in P. falciparum. In addition, P. falciparum growth inhibited by the N-alkoxy analog 16e is also restored by IPP supplementation (FIG. 3). Similar results were also observed for N-acyl analog 32a and 33a (FIG. 9). The data strongly suggest that these α,β-unsaturated fosmidomycin analogs are acting on target to inhibit parasitic growth by blocking the MEP pathway, the targeted intracellular pathway.

Figure 4:
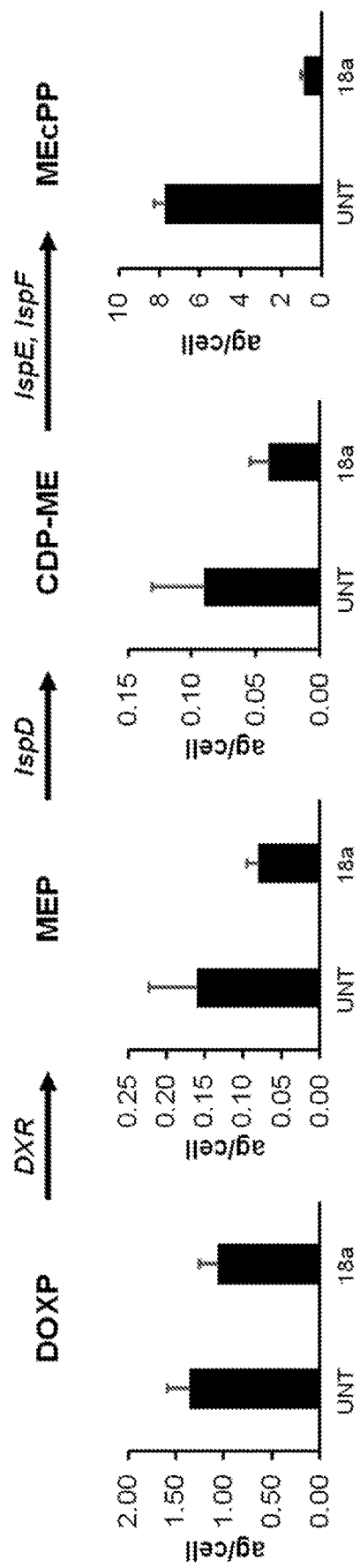
FIG. 4 depicts that treating P. falciparum with 18a results in diminished concentrations of MEP pathway metabolites. Intracellular concentrations of MEP pathway metabolites were measured, comparing untreated (UNT) parasites and those treated with 18a at 5× the $IC_{50}$ value of 13 nM.

Similarly, the DXR inhibitor 18a should deplete MEP pathway intermediates beyond DXR from the treated P. falciparum. Thus, a mass spectrometry-based method was used to quantify the MEP metabolites from untreated P. falciparum versus parasites treated with this compound (FIG. 4). These metabolites include the DXR substrate (1-deoxy-D-xylulose 5-phosphate, DOXP), the DXR product (2-C-methylerythritol 4-phosphate, MEP), and the downstream metabolites (4-diphosphocytidyl-2-C-methylerythritol (CDP-ME) and 2-C-methyl-D-erythritol 2,4-cyclopyrophosphate (MEcPP)). Such metabolite levels were measured by LC-MS/MS after the 3D7 parasites were treated with 18a after 10 h. The DOXP levels did not show significant difference between the untreated and treated parasites, while the metabolites downstream of DXR displayed reduced levels in treated parasites. This metabolic profiling data suggests that 18a inhibits DXR, the first committed enzyme in the MEP pathway from P. falciparum.

Figure 5:
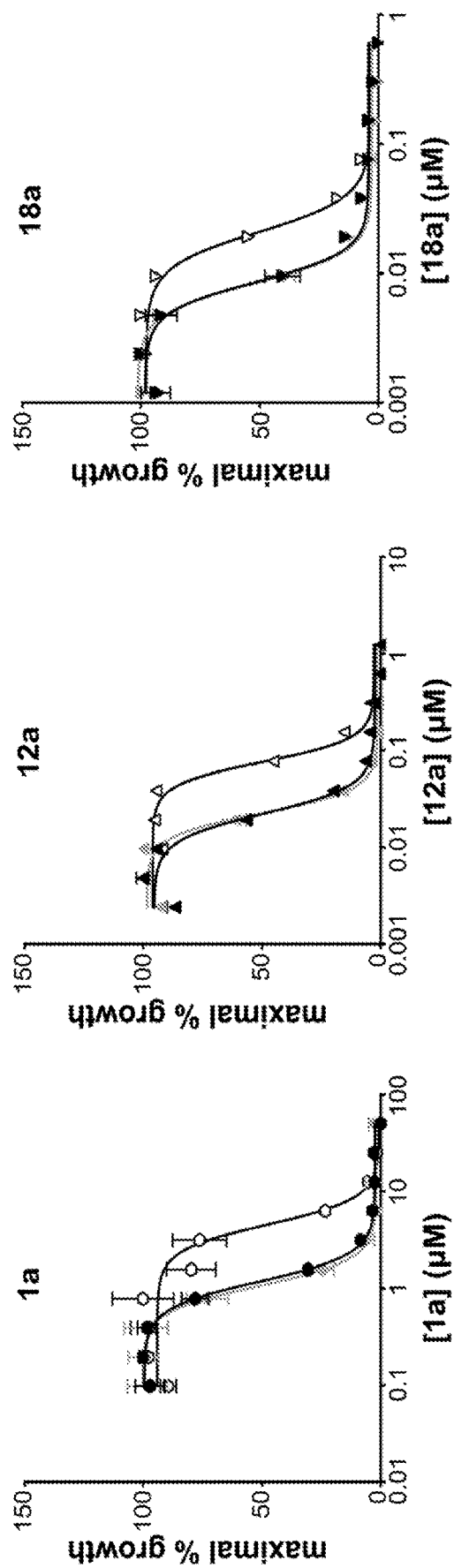
FIG. 5 depicts that P. falciparum had1 mutant strains resistant to fosmidomycin (1a) are also resistant to 12a and 18a. Dose-dependent growth inhibition was determined for P. falciparum strains treated with inhibitors. The had1 mutation results in higher levels of the DXR substrate DOXP are resistant to DXR inhibition as indicated by a shift in the $IC_{50}$ curve (had1; open shapes, black line) when compared to WT P. falciparum (3D7; closed shapes, grey line). Sensitivity was restored if a WT copy of had1 was supplied in the mutant strain (had1+HAD1-GFP; closed shapes, black line).
Figure 6:
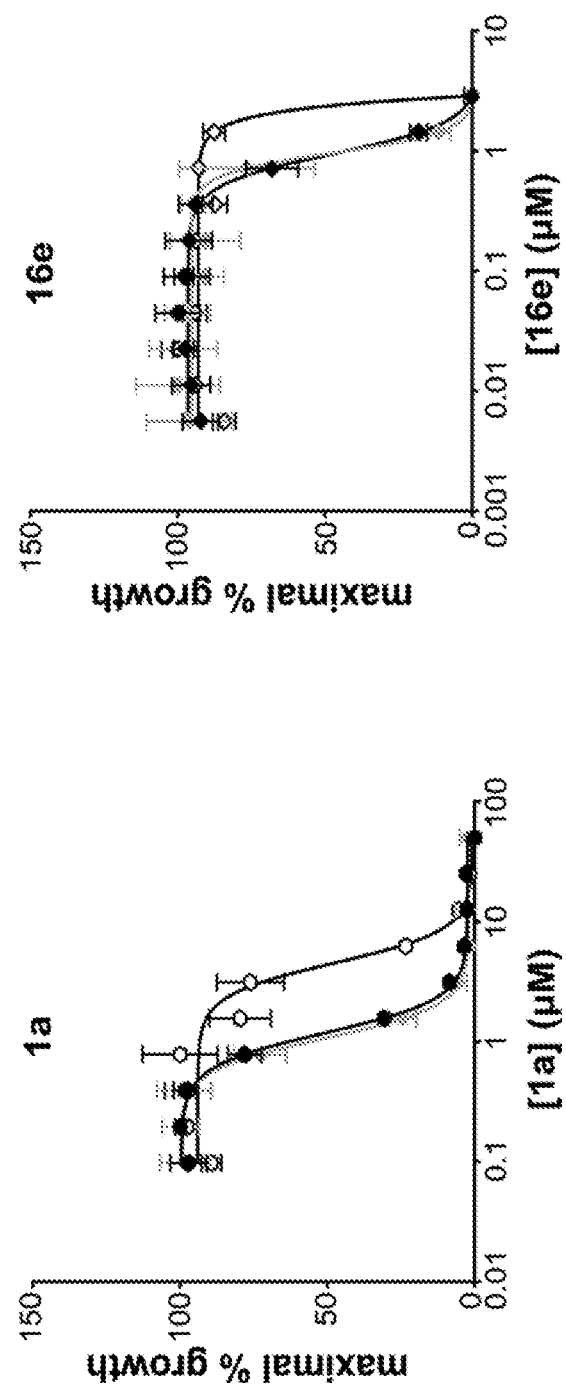
FIG. 6 depicts that P. falciparum strains with high levels of DOXP confer resistance to DXR inhibitor 16e. Dose-dependent growth inhibition was determined for P. falciparum strains treated with inhibitors. Strains with higher levels of the DXR substrate DOXP are more resistant to DXR inhibitors as indicated by a shift in the $IC_{50}$ curve (had1; open shapes, black line) when compared to WT P. falciparum (3D7; closed shapes, grey line). Sensitivity was restored if a WT copy of HAD1 was supplied in the mutant strain (had1+HAD1-GFP; closed shapes, black line).
Figure 10:
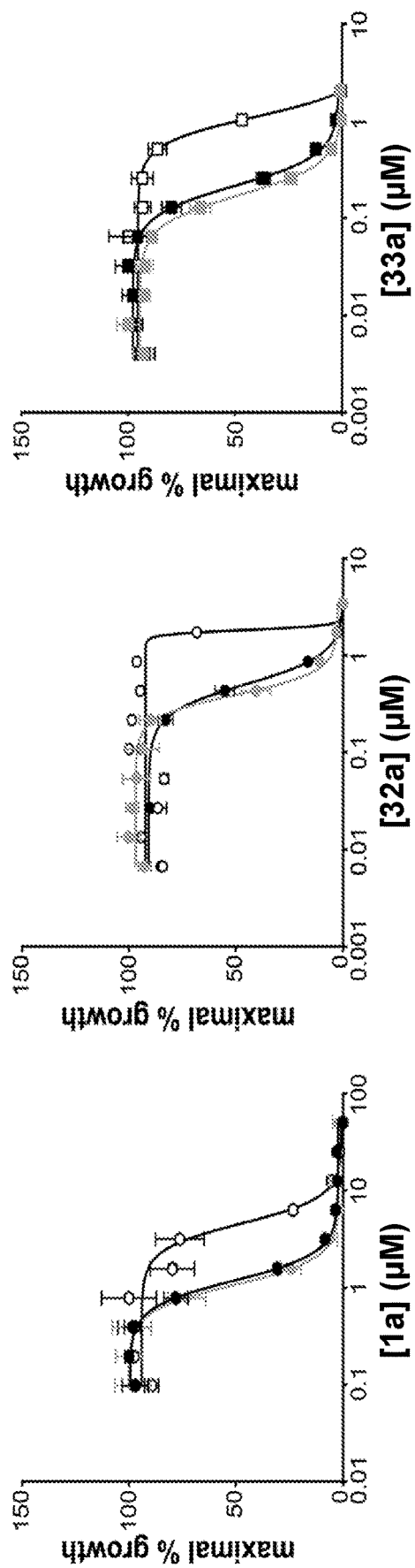

To further elucidate the mode of action of these analogs, compounds 12a and 18a were evaluated for efficacy against a unique mutated P. falciparum strain, using reported procedures. Guggisberg et al. Nature Communications 2014, 5, 4467. Due to a mutation in the metabolic regulator HAD1 (PF3D7_1033400), this P. falciparum strain produces high levels of DOXP, the substrate for DXR. Increased DOXP levels make it more difficult to inhibit DXR. For example, using this mutant, the (competitive) inhibition of DXR by fosmidomcyin (1a) is impeded, resulting in fosmidomycin (1)-resistant parasites (had1 parasites). As shown in FIG. 5, had1 parasites (had1; open shapes, black line) were 3.4-fold and 2.5-fold more resistant to 12a and 18a, respectively, when compared with wild-type P. falciaprum (3D7; closed shapes, grey line). Notably, the sensitivity of 12a and 18a were restored if the mutant strain was supplied with a wild-type copy of HAD1 (had1+HAD1-GFP; closed shapes, black line). Similar results were observed with N-alkoxy analog 16e and N-acyl analog 32a and 33a, where had1 parasites were more resistant to these compounds than wild-type parasites (FIG. 6 and FIG. 10). These data corroborate earlier findings that these α,β-unsaturated fosmidomycin analogs inhibit P. falciparum growth via inhibition of the DXR enzyme in the MEP pathway.

In Vivo Evaluation of 18e in a Mouse Model of Malaria Infection.

Figure 7B:
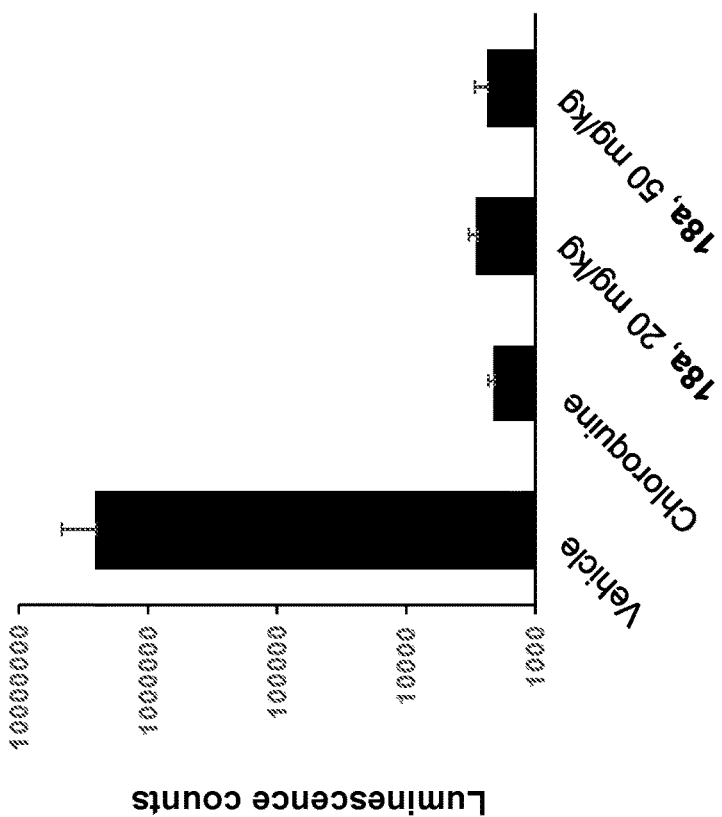
FIGS. 7A and 7B depict that compound 18a is effective in an in vivo mouse model of efficacy. Mice were imaged using an IVIS imager at 7 days post-infection (FIG. 7A) and parasitemia was quantified (FIG. 7B).
Figure 7A:
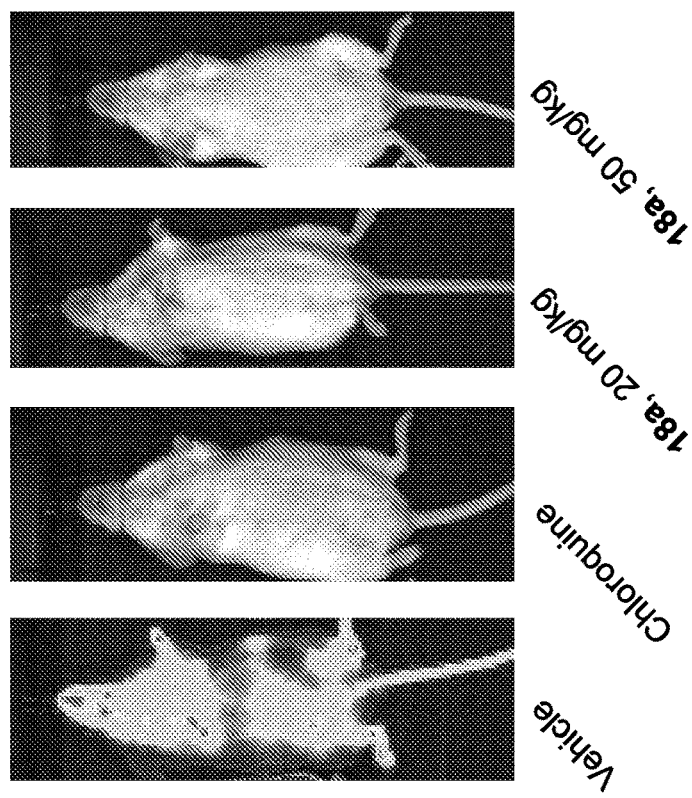

Compound 18a was further evaluated for in vivo efficacy in a P. berghei-infected mouse model of malaria using reported procedures. 1. Edwards et al., Scientific Reports 2017, 7, 8400. Groups of mice were infected with luciferase-based blood-stage P. berghei ANKA by intraperitoneal (ip) injection. After being infected for two days, the mice were treated daily for five days with vehicle, 20 mg/kg chloroquine, 20 mg/kg 18a, or 50 mg/kg 18a via i.p. injection. Seven days after infection, intensity of the luciferin signal was measured, correlating to the parasitemia burden. As shown in FIGS. 7A and 7B, parasitemia was greatly reduced in mice treated with the control drug chloroquine (20 mg/kg), lowering the luciferin signal intensity to $2.13 \times 10^3$. Interestingly, mice treated with 18a at the same dose showed a similar result as chloroquine, with a 3-log drop in luciferin signal intensity ($2.87 \times 10^3$) when compared to the vehicle ($2.62 \times 10^6$). When a higher dose of 18a was administered, the average luciferin signal intensity of the P. berghei-infected mice is $2.34 \times 10^3$, not significantly different from the result with the lower dose. Additionally, 18a was well tolerated in mice at these dosages, as no adverse effects were observed, corroborating our results with the HepG2 cells.

Figure 8:
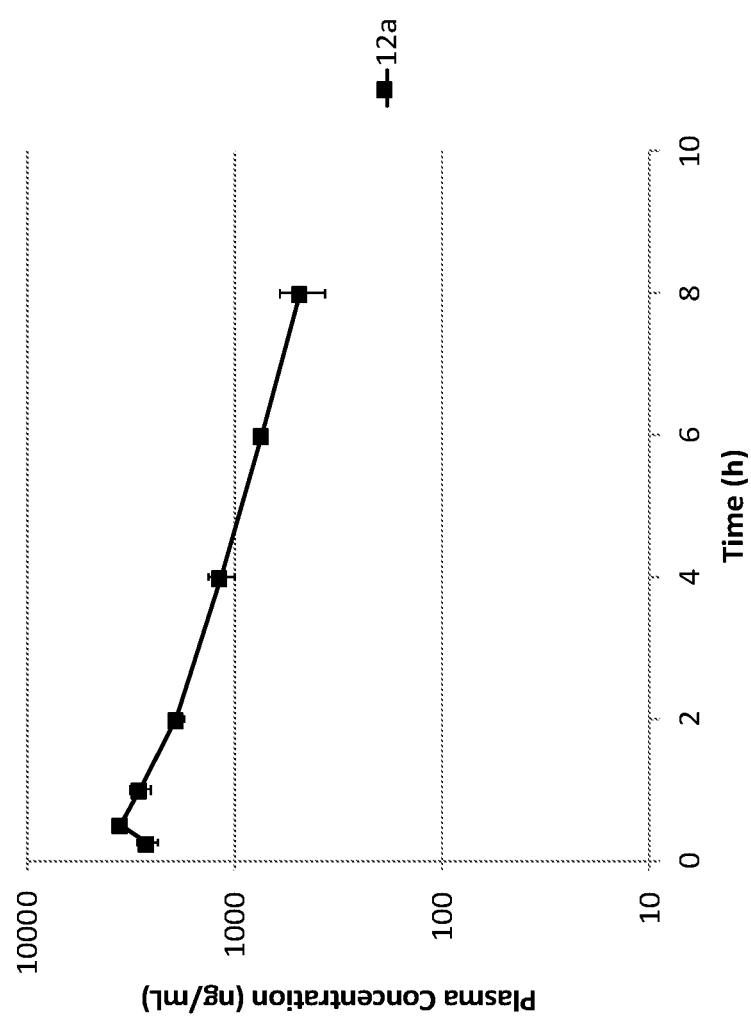
FIG. 8 depicts that compound 18a is rapidly converted to 12a in vivo when dosed at 20 mg/kg i.p. in Swiss Webster mice.

Based on the in vitro stability studies, it was expected that 18a would be rapidly converted to 12a in the in vivo study. We designed a compound exposure study to determine plasma concentration of 12a under similar conditions to the efficacy study. Compound 18a was dosed at 20 mg/kg i.p. in Swiss Webster mice (n=3) and plasma samples were removed at select time points over the course of 8 h (FIG. 8). Over the course of 8 h, 12a was observed at high concentrations, with a concentration of 485 ng/mL (2.8 μM) at 8 h which is approximately 200-fold above the Pf $IC_{50}$ of 18a in vitro.

Dxr Inhibition and Antimicrobial Activities of N-Acyl Analogs.

Phosphonic acid salts and prodrugs were evaluated as inhibitors of DXR from Mtb and P. falciparum and the results are shown in Table 6. Initially, the percent remaining enzyme activity was studied using a treatment of each compound at a single concentration of 100 μM. This data shows the intrinsic activities of the compounds and trends of the N-acyl series. To obtain more accurate activities for potent DXR inhibitors, half-maximal inhibitory concentrations ($IC_{50}$ values) were further determined for compounds with greater than 75% DXR inhibition. In general, the compounds display greater inhibition of DXR from P. falciparum compared with activity against the Mtb homolog. The most potent compounds are 32a and 32b. Interestingly, the activities of these compounds are equal to or slightly better than the activity of parent unsaturated compound 2 against P. falciparum DXR. For 32a-d, the optimal carbon linker length for P. falciparum DXR inhibition is zero carbon atoms as 32a is the most potent ($IC_{50}$ value of 0.11 μM). Compound 32b (with a methylene linker) is very potent, with an $IC_{50}$ value of 0.17 μM. None of these compounds inhibit Mtb DXR to a significant extent.

TABLE 6

Dxr inhibition and antimicrobial activities of N-acyl analogs $$\text{R}_1\text{O}-\underset{\text{R}_1\text{O}}{\overset{\overset{\text{O}}{\|}}{\text{P}}}-\text{CH}=\text{CH}-\text{CH}_2-\underset{\underset{\text{O}}{\|}}{\overset{\text{OH}}{\text{N}}}-\text{R}_3$$

| Cmpd | $R_1$ | $R_3$ | Pf Dxr $IC_{50}$ [µM] (% Residue) | Mtb Dxr $IC_{50}$ [µM] (% Residue) | P.f. $IC_{50}$ [µg/mL] | Mtb $MIC_{99}$ [µg/mL] 7H9 | Gast/ Fe | HepG2 $IC_{50}$ [µM] |
|---|---|---|---|---|---|---|---|---|
| 2   | Na/H | $CH_3$       |        | $1.07^a$ | 203 $nM^b$ | >$200^a$ | $150^a$ |     |
| 31a | Et   | Ph           |        |          | >100       | >100     | >100    |     |
| 31b | Et   | $CH_2Ph$     |        |          | 110.1      | >100     | n.d.    |     |
| 31c | Et   | $(CH_2)_2Ph$ |        |          | >100       | >100     | >100    |     |
| 31d | Et   | $(CH_2)_3Ph$ |        |          | 11.1       | >100     | >100    |     |
| 32a | Na/H | Ph           | 0.1062 | (36.87)  | 0.103      | >50      | 25      | >50 |
| 32b | Na/H | $CH_2Ph$     | 0.17   | (33.6)   | 0.137      | >100     | n.d.    |     |
| 32c | Na/H | $(CH_2)_2Ph$ | 1.34   | (62.3)   | 3.3        | >100     | >100    |     |
| 32d | Na/H | $(CH_2)_3Ph$ | 0.8976 | (29.2)   | 1.6        | >100     | >100    |     |
| 33a | POM  | Ph           |        |          | 0.097      | 50       | n.d.    | >50 |
| 33b | POM  | $CH_2Ph$     |        |          | 0.152      | 100      | 74      |     |
| 33d | POM  | $(CH_2)_3Ph$ |        |          | 2.4        | >100     | 37      |     |

Mtb = *M. tuberculosis*;
Pf = *P. falciparum*;
$IC_{50}$ = inhibitory concentration at 50%;
$MIC_{99}$ = inhibitory concentration at 99%;
n.d. = not determined.
[a] Jackson et al., *Bioorganic & Medicinal Chemistry Letters* 2014, 24 (2), 649-653.
[b] Edwards et al., *Scientific Reports* 2017, 7, 8400.

Selected analogs were tested for the growth inhibition against P. falciparum and Mtb in both rich media (7H9) and minimal media (GAST-Fe) following reported procedures.

The eukaryotic parasite P. falciparum has a cell membrane that is much more penetrable compared with the Mtb cell walls. Thus, this membrane character, as well as remodeled host cell membranes by malaria parasites, lead one to expect increased cellular uptake into P. falciparum compared with Mtb. In Table 6, the polar phosphonic acid salts show greater activity against P. falciparum parasites compared with Mtb cells. Compounds 32a and 32b are the most active of the set, with activities surpassing that of parent compound (and clinically evaluated candidate) fosmidomycin. The data also shows that the inhibition of P. falciparum growth corresponds well to the activities of these compounds against the enzyme target P. falciparum DXR.

As was the case with the phosphonic acid salts, several of the POM prodrugs are highly active against P. falciparum. Given the increased lipophilicity of the prodrug, selective compounds display antimycobacterial activity. In addition, the prodrugs generally show similar cellular effects as their parent structures. Of the N-acyl series, compound 32a was the most potent P. falciparum DXR inhibitor. Its prodrug 33a is also the most potent inhibitor of P. falciparum ($IC_{50}$=0.097 µg/mL) from this series. The compounds in Table 6 showed only modest inhibition of Mtb growth.

Neither the phosphonic acid salt 32a nor the prodrug 33a show any toxicity against HepG2 cell lines, with $IC_{50}$ values >50 µM. These compounds show promise as safe drug candidates for malaria.

Example 3. Synthesis of α,β-unsaturated fosmidomycin analogs General $^1$H and $^{13}$C NMR spectra were recorded in $CDCl_3$, $CD_3OD$ or $D_2O$ on Agilent spectrometer at 400 and 101 MHz, respectively, with TMS, H2O or solvent signal as internal standard. Chemical shifts are given in parts per million (ppm). Spin multiplicities are given with the following abbreviations: s (singlet), br s (broad singlet), d (doublet), dd (doublet of doublets), ddd (doublet of doublets of doublets), t (triplet), dt (doublet of triplets), ddt (doublet of doublet of triplets), q (quadruplet), qt (quintuplet), m (multiplet). Mass spectra were measured in the ESI mode on an HPLC-MS (Agilent 1100) or in the EI mode on an GC-MS (Shimadzu GCMS-QP2010S). Thin layer chromatography (TLC) was performed on Baker-flex Silica Gel IB2-F silica plates and flash column chromatography was carried out using SiliCycle SiliaFlash P60 silica gel (40-63 µm). All reagents were purchase from commercial suppliers and used without further purification. Anhydrous solvents were purified by MBRAUN MB-SPS solvent purification system before use. All air sensitive reactions were carried out under nitrogen atmosphere. The purity of synthesized compounds (>95%) was determined by $^1H/^{13}C$ NMR in combination with HPLC-MS (Agilent 1100). Column: Thermo Fisher Scientific Hypersil GOLD aQ C-18 3 µm particle (250 mm×4.6 mm). Mobile phase (containing 0.1% formic acid as the additive): linear gradient of acetonitrile (50%-100%) in water at a flow rate of 0.8 mL/min over 12.5 min, followed by 100% acetonitrile that was maintained for another 12.5 min. The UV detection wavelength was 210 nm and 254 nm. High-resolution mass spectroscopy spectra (HRMS) were recorded in positive or negative ESI mode on a Waters Q-TOF Ultima mass spectrometer (UIUC Mass Spectrometry Laboratory) or in positive FAB mode on a VG Analytical VG70SE magnetic sector mass spectrometer (JHU Mass Spectrometry Facility).

Diethyl (prop-2-en-1-yl)phosphonate (6)

Triethyl phosphite (10 mL, 58 mmol, 1 eq) and allyl bromide (6.5 mL, 75 mmol, 1.3 eq) were added to an oven-dried round bottom flask covered with foil. The reaction mixture was stirred at 60° C. for 2 days, purified by fractional distillation under reduced pressure using a Kugelrohr to afford the title compound as a colorless oil (8.8 g, 85%). $^1$H NMR (400 MHz, CDCl$_3$) δ 5.95-5.69 (m, 1H), 5.31-5.13 (m, 2H), 4.25-3.99 (m, 4H), 2.62 (ddt, J=21.9, 7.4, 1.3 Hz, 2H), 1.32 (t, J=7.1 Hz, 6H). $^{13}$C NMR (101 MHz, CDCl$_3$) δ 127.7 (d, J=11.3 Hz), 120.0 (d, J=14.4 Hz), 62.1 (d, J=6.5 Hz), 32.0 (d, J=139.4 Hz), 16.6 (d, J=6.0 Hz). GC-MS (EI): 178 m/z [M].

Diethyl (2,3-dibromopropyl)phosphonate (7)

To a solution of 6 (2.9 g, 16 mmol, 1 eq) in dry CH$_2$Cl$_2$ (30 mL) under N$_2$ was added Bromine (1 mL, 19.6 mmol, 1.2 eq) at 0° C. dropwise. The reaction mixture was stirred at room temperature for 2 h, quenched with saturated Na$_2$SO$_3$ (aq, 30 mL) and extracted with CH$_2$Cl$_2$ (3×30 mL). The combined organic layers were dried with anhydrous Na$_2$SO$_4$, filtered, and concentrated under reduced pressure to afford the title compound as a light yellow oil (4.9 g, 88%) without further purification. $^1$H NMR (400 MHz, CDCl$_3$) δ 4.49-4.37 (m, 1H), 4.23-4.07 (m, 4H), 3.93 (ddd, J=10.8, 4.4, 2.1 Hz, 1H), 3.78 (dd, J=10.8, 7.3 Hz, 1H), 2.78 (ddd, J=18.8, 15.8, 6.1 Hz, 1H), 2.39 (ddd, J=18.4, 15.8, 7.3 Hz, 1H), 1.37-1.32 (m, 6H). $^{13}$C NMR (101 MHz, CDCl$_3$) δ 62.2 (dd, J=21.6, 6.6 Hz), 43.4 (d, J=2.8 Hz), 38.0 (d, J=11.1 Hz), 33.9 (d, J=141.3 Hz), 16.4 (dd, J=6.1, 3.5 Hz). LC-MS (ESI$^+$): 337.0, 339.0, 341.0 m/z [M+H]$^+$.

tert-Butyl N-(benzyloxy)carbamate (8)

To a stirred solution of O-benzylhydroxylamine hydrochloride (9.6 g, 60 mmol, 1 eq) and triethylamine (9.0 mL, 66 mmol, 1.1 eq) in a 1:1 mixture of THF/H$_2$O (100 mL), was added di-tert-butyl dicarbonate (30% in dioxane, 43.7 mL, 60 mmol, 1 eq). The reaction mixture was stirred at room temperature for 2.5 h, and then concentrated under reduced pressure to eliminate THF. The residue was extracted with EtOAc (3×50 mL), the combined organic layers were washed with 0.5 M citric acid (aq, 2×50 mL) and H$_2$O (50 mL). The organic layer was dried with anhydrous Na$_2$SO$_4$, filtered and concentrated under reduced pressure to give the crude solid. The crude solid was then recrystallized in hexanes to afford the title compound as a white solid (12 g, 90%). $^1$H NMR (400 MHz, CDCl$_3$) δ 7.97-7.29 (m, 5H), 5.28 (s, 2H), 1.90 (s, 9H). 13C NMR (101 MHz, CDCl$_3$) δ 156.3, 135.7, 129.1, 128.5, 81.7, 78.4, 28.2. LC-MS (ESI$^+$): 245.9 m/z [M+Na]$^+$, 460.0 m/z [2M+Na]$^+$.

tert-butyl N-(benzyloxy)-N-[(2E)-3-(diethoxyphosphoryl)prop-2-en-1-yl]carbamate (9)

To a solution of 8 (1.2 g, 5.4 mmol, 1 eq) in dry THF (15 mL) under N$_2$ at 0° C. was added dropwise a suspension of NaH (60% in oil, 430 mg, 10.8 mmol, 2 eq) in dry THF (10 mL). This mixture was stirred at 0° C. for 30 min at which point 7 (2 g, 5.9 mmol, 1.1 eq) in dry THF (3 mL) was added as well as NaI (16 mg, 0.11 mmol, 0.02 eq) at 0° C. The reaction mixture was stirred at room temperature for 20 h, quenched with saturated NaHCO$_3$ (aq, 30 mL), concentrated under reduced pressure to eliminate THF and extracted with EtOAc (3×30 mL). The combined organic layers were dried with anhydrous Na$_2$SO$_4$, filtered and concentrated under reduced pressure. Chromatographic separation on silica gel (EtOAc/CH$_2$Cl$_2$=2/1) gave the title compound as a light yellow oil (1.6 g, 77%). $^1$H NMR (400 MHz, CDCl$_3$) δ 7.39-7.31 (m, 5H), 6.69 (ddt, J=22.4, 17.2, 5.3 Hz, 1H), 5.82 (ddt, J=18.9, 17.2, 1.7 Hz, 1H), 4.83 (s, 2H), 4.12-4.02 (m, 6H), 1.49 (s, 9H), 1.31-1.27 (m, 6H). $^{13}$C NMR (101 MHz, CDCl$_3$) δ 156.3, 146.4 (d, J=5.3 Hz), 135.4, 129.3, 128.6, 128.4, 119.5 (d, J=187.6 Hz), 82.0, 61.8 (d, J=5.6 Hz), 52.5 (d, J=24.6 Hz), 28.2, 16.3 (d, J=6.5 Hz). LC-MS (ESI$^+$): 799.2 m/z [2M+H]$^+$.

General Procedure A for Synthesis of Amide 10a-c and 13

To a solution of MeOH (10.1 eq) in dry CH$_2$Cl$_2$ (1 M) under N$_2$ was added acetyl chloride (10 eq) dropwise at room temperature and the mixture was stirred for 10 min. The reaction mixture was then added a solution of 9 (1 eq) in dry CH$_2$Cl$_2$ (1 M) and stirred at room temperature for 30 min. After the completion of deprotection, dry Na$_2$CO$_3$ (12 eq) was added at 0° C. and the mixture was stirred at the same temperature for 10 min. The reaction mixture at 0° C. was added dropwise RCOCl, (CF$_3$CO)$_2$O or N-formylimidazole* (2 eq). The mixture was then warmed up to room temperature and stirred for 30 min to 24 h, quenched with saturated NaHCO$_3$ (aq) and extracted with CH$_2$Cl$_2$ (3×). The combined organic layers were dried with anhydrous Na$_2$SO$_4$, filtered and concentrated under reduced pressure. The crude concentrate was then purified by column chromatography on silica gel using EtOAc and CH$_2$Cl$_2$ (with a ratio from 1/10 to 2/1) to give the pure title compound.

*N-Formylimidazole

To a suspension of 1,1'-carbonyldiimidazole (2.1 eq) in dry CH$_2$Cl$_2$ (2 M) under N$_2$ was added formic acid (2 eq) slowly at room temperature. The mixture was then stirred for 30 min to give a solution of N-formylimidazole in CH$_2$Cl$_2$ in situ, which was used immediately.

Diethyl [(1E)-3-[N-(benzyloxy)formamido]prop-1-en-1-yl]phosphonate (10a)

Light yellow oil (594 mg, 73%). $^1$H NMR (400 MHz, cdcl$_3$) δ 8.24 (s, 1H), 7.41-7.29 (m, 5H), 6.72-6.57 (m, 1H), 5.82 (ddd, J=12.4, 10.0, 6.3 Hz, 1H), 4.84 (s, 2H), 4.30-4.20 (m, 2H), 4.13-3.98 (m, 4H), 1.32-1.27 (m, 6H). $^{13}$C NMR (101 MHz, cdcl$_3$) δ 163.3, 144.40 (d, J=5.7 Hz), 134.1, 129.4, 129.2, 128.8, 120.8 (d, J=188.7 Hz), 78.3, 61.9 (d, J=5.6 Hz), 47.2 (d, J=26.7 Hz), 16.3 (d, J=6.3 Hz). LC-MS (ESI$^+$): 328.2 m/z [M+H]$^+$, 655.2 m/z [2M+H]$^+$.

Diethyl [(1E)-3-[N-(benzyloxy)-2,2,2-trifluoroacetamido]prop-1-en-1-yl]phosphonate (10b)

Light yellow solids (720 mg, 73%) $^1$H NMR (400 MHz, cdcl$_3$) δ 7.53-7.30 (m, 5H), 6.66 (ddt, J=21.6, 17.2, 5.2 Hz, 1H), 5.91-5.80 (m, 1H), 4.94 (s, 2H), 4.43-4.36 (m, 2H), 4.12-4.01 (m, 4H), 1.32-1.28 (m, 6H). $^{13}$C NMR (101 MHz, cdcl$_3$) δ 142.7 (d, J=5.9 Hz), 129.4, 129.2, 128.8, 121.6 (d, J=187.5 Hz), 115.9 (q, J=286.9 Hz), 78.4, 62.0 (d, J=5.7 Hz), 49.5 (d, J=24.9 Hz), 16.3 (d, J=6.2 Hz). LC-MS (ESI$^+$): 396.2 m/z [M+H]$^+$, 791.2 m/z [2M+H]$^+$.

Methyl N-(benzyloxy)-N-[(2E)-3-(diethoxyphosphoryl)prop-2-en-1-yl]carbamate (10c)

Light yellow oil (444 mg, 50%). $^1$H NMR (400 MHz, cdcl$_3$) δ 7.37-7.29 (m, 5H), 6.73-6.59 (m, 1H), 5.86-5.74 (m, 1H), 4.84 (s, 2H), 4.13-4.09 (m, 2H), 4.07-3.98 (m, 4H), 3.77 (s, 3H), 1.30-1.24 (m, 6H). $^{13}$C NMR (101 MHz, cdcl$_3$) δ 157.7, 145.8 (d, J=5.3 Hz), 135.1, 129.2, 128.7, 128.4, 120.0 (d, J=187.5 Hz), 77.5, 61.8 (d, J=5.6 Hz), 53.4, 52.5 (d, J=24.7 Hz), 16.3 (d, J=6.3 Hz). LC-MS (ESI$^+$): 358.2 m/z [M+H]+, 715.2 m/z [2M+H]+.

Diethyl [(1E)-3-[N-(benzyloxy)acetamido]prop-1-en-1-yl]phosphonate (13)

Light yellow oil (722 mg, 85%). $^1$H NMR (400 MHz, cdcl$_3$) δ 7.43-7.31 (m, 5H), 6.77-6.63 (m, 1H), 5.81 (ddt, J=20.6, 17.2, 1.7 Hz, 1H), 4.83 (s, 2H), 4.38-4.31 (m, 2H), 4.12-4.01 (m, 4H), 2.14 (s, 3H), 1.30 (ddd, J=5.9, 5.0, 0.4 Hz, 6H). $^{13}$C NMR (101 MHz, cdcl$_3$) δ 145.7 (d, J=5.5 Hz), 134.2, 129.2, 129.1, 128.7, 119.9 (d, J=187.8 Hz), 77.0, 61.9 (d, J=5.6 Hz), 48.7 (d, J=25.3 Hz), 20.4, 16.3 (d, J=6.3 Hz). LC-MS (ESI$^+$): 342.2 m/z [M+H]+, 683.2 m/z [2M+H]+.

General Procedure B for Synthesis of 11a-c, 14 and 18a-c

To a solution of 10, 13 or 17 (1 eq) in dry CH$_2$Cl$_2$ (0.1 M) under N$_2$ was added boron trichloride (1M in CH$_2$Cl$_2$, 4 eq) at −78° C. dropwise. The reaction mixture was stirred at −78° C. for 30 min to 3 h, quenched with saturated NaHCO$_3$ (aq) and extracted with EtOAc (5×). The combined organic layers were dried with anhydrous Na$_2$SO$_4$, filtered and concentrated under reduced pressure. The crude residue was then purified by column chromatography on silica gel using EtOAc and MeOH (EtOAc and CH$_2$Cl$_2$ for 18a-c) to give the pure title compound.

Diethyl [(1E)-3-(N-hydroxyformamido)prop-1-en-1-yl]phosphonate (11a)

Light yellow oil (106 mg, 55%). $^1$H NMR (400 MHz, cdcl$_3$) δ 10.06 (s, 1H), 8.32 (s, 1H), 6.75-6.55 (m, 1H), 5.99-5.74 (m, 1H), 4.32-4.25 (m, 2H), 4.09-3.92 (m, 4H), 1.25 (t, J=7.1 Hz, 6H). $^{13}$C NMR (101 MHz, cdcl$_3$) δ 172.5, 162.78, 146.3 (d, J=5.5 Hz), 118.7 (d, J=189.1 Hz), 62.3 (d, J=5.7 Hz), 48.9 (d, J=25.3 Hz,), 16.17 (d, J=6.4 Hz). LC-MS (ESI$^+$): 238.0 m/z [M+H]+, 475.2 m/z [2M+H]+.

Diethyl [(1E)-3-(2,2,2-trifluoro-N-hydroxyacetamido)prop-1-en-1-yl]phosphonate (11b)

Light yellow oil (44 mg, 19%). $^1$H NMR (400 MHz, cdcl$_3$) δ 10.78 (s, 1H), 6.89 (ddt, J=22.8, 17.2, 5.7 Hz, 1H), 5.94 (ddt, J=18.8, 17.2, 1.5 Hz, 1H), 4.50-4.46 (m, 2H), 4.08-3.99 (m, 4H), 1.35-1.28 (m, 6H). $^{13}$C NMR (101 MHz, cdcl$_3$) δ 156.8 (q, J=36.3 Hz), 145.8 (d, J=6.0 Hz), 119.6 (d, J=191.2 Hz), 116.3 (q, J=286.9 Hz), 62.5 (d, J=5.9 Hz), 51.8 (d, J=26.5 Hz), 16.1 (d, J=6.5 Hz). LC-MS (ESI$^+$): 306.0 m/z [M+H]$^+$, 611.0 m/z [2M+H]$^+$.

Methyl N-[(2E)-3-(diethoxyphosphoryl)prop-2-en-1-yl]-N-hydroxycarbamate (11c)

Colorless oil (135 mg, 85%). $^1$H NMR (400 MHz, cdcl$_3$) δ 9.27 (s, 1H), 6.78 (ddt, J=22.2, 17.2, 4.9 Hz, 1H), 5.94 (ddt, J=19.8, 17.2, 1.7 Hz, 1H), 4.35-4.28 (m, 2H), 4.11-4.03 (m, 4H), 3.76 (s, 3H), 1.32 (m, 6H). $^{13}$C NMR (101 MHz, cdcl$_3$) δ 157.9, 147.4 (d, J=5.5 Hz), 118.0 (d, J=189.0 Hz), 62.0 (d, J=5.6 Hz), 53.2, 53.1 (d, J=23.8 Hz), 16.2 (d, J=6.4 Hz). LC-MS (ESI$^+$) 268 m/z [M+H$^+$], 535 m/z [2M+H$^+$].

Diethyl [(1E)-3-(N-hydroxyacetamido)prop-1-en-1-yl]phosphonate (14)

Colorless oil (512 mg, 77%). $^1$H NMR (400 MHz, cdcl$_3$) δ 9.91 (s, 1H), 6.72 (ddt, J=22.3, 17.2, 5.1 Hz, 1H), 5.96-5.82 (m, 1H), 4.44-4.39 (m, 2H), 4.09-4.01 (m, 4H), 2.19 (s, 3H), 1.32 (m, 6H). $^{13}$C NMR (101 MHz, cdcl$_3$) δ 172.5, 147.6 (d, J=5.3 Hz), 117.9 (d, J=189.0 Hz), 62.2 (d, J=5.7 Hz), 50.4 (d, J=25.1 Hz), 20.3, 16.2 (d, J=6.4 Hz). LC-MS (ESI$^+$): 252.2 m/z [M+H]$^+$, 503.2 m/z [2M+H]$^+$.

[({[(2,2-dimethylpropanoyl)oxy]methoxy}[(1E)-3-(N-hydroxyformamido)prop-1-en-1-yl]phosphoryl)oxy]methyl 2,2-dimethylpropanoate (18a)

Light yellow oil (103 mg, 55%). $^1$H NMR (400 MHz, cdcl$_3$) δ 9.41 (s, 1H), 8.42 and 7.94 (s, 1H), 6.87-6.69 (m, 1H), 6.07-5.88 (m, 1H), 5.71-5.59 (m, 4H), 4.37-4.32 (m, 2H), 1.21 (s, 18H). $^{13}$C NMR (101 MHz, cdcl$_3$) δ 177.1, 163.0, 157.3, 147.3 (d, J=6.1 Hz), 118.6 (d, J=191.8 Hz), 81.6 (d, J=4.9 Hz), 48.8 (d, J=26.1 Hz), 38.7, 26.8. LC-MS (ESI$^+$): 410.2 m/z [M+H]$^+$, 819.2 m/z [2M+H]$^+$. HRMS (ESI$^+$) calculated for C$_{1-6}$H$_{28}$NO$_9$P, 409.1502; found, 432.1388 [M+Na]$^+$.

[({[(2,2-dimethylpropanoyl)oxy]methoxy}[(1E)-3-(2,2,2-trifluoro-N-hydroxyacetamido)prop-1-en-1-yl]phosphoryl)oxy]methyl 2,2-dimethylpropanoate (18b)

Light yellow oil (15 mg, 34%). $^1$H NMR (400 MHz, cdcl$_3$) δ 9.59 (bs, 1H), 6.86 (ddt, J=22.9, 17.2, 5.4 Hz, 1H), 6.04-5.89 (m, 1H), 5.69-5.54 (m, 4H), 4.50-4.45 (m, 2H), 1.21 (s, 18H). $^{13}$C NMR (101 MHz, cdcl$_3$) δ 177.1, 146.2 (d, J=5.8 Hz), 119.0 (d, J=192.8 Hz), 116.1 (q, J=286.9 Hz), 81.6 (d, J=5.1 Hz), 51.4 (d, J=26.7 Hz), 38.7, 26.7. LC-MS (ESI$^+$): 478.2 m/z [M+H]$^+$, 955.2 m/z [2M+H]$^+$. HRMS (ESI$^+$) calculated for C$_{1-6}$H$_{28}$NO$_9$P, 409.1502; found, 432.1388 [M+Na]$^+$.

[({[(2,2-dimethylpropanoyl)oxy]methoxy}[(1E)-3-[hydroxy(methoxycarbonyl)amino]prop-1-en-1-yl]phosphoryl)oxy]methyl 2,2-dimethylpropanoate (18c)

Light yellow oil (27 mg, 34%). $^1$H NMR (400 MHz, cdcl$_3$) δ 7.98 (s, 1H), 6.88-6.71 (m, 1H), 6.03-5.88 (m, 1H), 5.68-5.58 (m, 4H), 4.32-4.27 (m, 2H), 3.75 (s, 3H), 1.20 (s, 18H). $^{13}$C NMR (101 MHz, cdcl$_3$) δ 176.9, 157.8, 148.1 (d, J=6.0 Hz), 117.8 (d, J=192.2 Hz), 81.5 (d, J=5.1 Hz), 53.5, 52.8 (d, J=25.6 Hz), 38.7, 26.8. LC-MS (ESI$^+$): 440.2 m/z [M+H]$^+$, 879.2 m/z [2M+H]$^+$. HRMS (FAB$^+$) calculated for C$_{17}$H$_{30}$NO$_{10}$P, 439.1607; found, 440.1671 [M+H]$^+$.

General Procedure C for Synthesis of 12a-b and 16d-g

To a solution of 11a-b or 15d-g (1 eq) in dry CH$_2$Cl$_2$ (0.1 M) under N$_2$ was added TMSBr (10 eq) dropwise at 0° C. The reaction mixture was warmed to room temperature, stirred overnight, and then concentrated under reduced pressure. The mixture was dissolved in CH$_2$Cl$_2$, evaporated under reduced pressure and dried under vacuum. The crude residue was then stirred in 0.5 M NaOH (1 eq) in H$_2$O at room temperature for 1 h, washed with Et$_2$O three times and lyophilized to give the title compounds.

Sodium hydrogen [(1E)-3-(N-hydroxyformamido)prop-1-en-1-yl]phosphonate (12a)

Light yellow solids (29 mg, quantitative yield). $^1$H NMR (400 MHz, cd$_3$od) δ 8.32 and 7.99 (s, 1H), 6.52-6.30 (m, 1H), 6.11-5.93 (m, 1H), 4.32-4.17 (m, 2H). $^{13}$C NMR (101 MHz, cd$_3$od) δ 162.6, 137.5 (d, J=5.0 Hz), 127.3 (d, J=178.0 Hz), 48.7 (d, J=23.6 Hz). LC-MS (ESI$^-$): 361.0 m/z [2M−2Na+H]$^-$, 542.2 m/z [3M−3Na+2H]$^-$. HRMS (ESI$^-$) calculated for C$_4$H$_7$NNaO$_5$P, 202.9960; found, 180.0065 [M−Na]$^-$.

Sodium hydrogen [(1E)-3-(2,2,2-trifluoro-N-hydroxyacetamido)prop-1-en-1-yl]phosphonate (12b)

Light yellow solids (22 mg, quantitative yield). Rotamers with a ratio of 3:1. $^1$H NMR (400 MHz, cd$_3$od) δ 6.71-6.52 (m, 4H), 6.31 (t, J=17.4 Hz, 3H), 6.01 (t, J=17.4 Hz, 1H), 4.48-4.36 (m, 2H), 4.08-3.97 (m, 6H). $^{13}$C NMR (101 MHz, cd$_3$od) δ 156.5 (q, J=35.9 Hz), 140.0, 134.6, 129.2 (d, J=183.2 Hz), 116.4 (q, J=286.2 Hz), 52.3 (d, J=25.2 Hz). LC-MS (ESI$^-$): 248.0 m/z [M−Na]$^-$, 497.0 m/z [2M−2Na+H]$^+$. HRMS (ESI$^-$) calculated for C$_5$H$_6$F$_3$NNaO$_5$P, 270.9833; found, 247.9937 [M−Na]$^-$.

Sodium hydrogen [(1E)-3-[N-(1-phenylethoxy)acetamido]prop-1-en-1-yl]phosphonate (16d)

White solids (28 mg, 77%). $^1$H NMR (400 MHz, d$_2$o) δ 7.55-7.42 (m, 5H), 6.32 (ddt, J=22.2, 17.3, 5.0 Hz, 1H), 5.91-5.76 (m, 1H), 5.13 (q, J=6.6 Hz, 1H), 4.41-4.30 (m, 1H), 4.10-3.98 (m, 1H), 2.04 (s, 3H), 1.61 (d, J=6.5 Hz, 3H). $^{13}$C NMR (101 MHz, d$_2$o) δ 140.0, 139.4, 129.3, 128.9, 127.9, 123.9 (d, J=179.3 Hz), 83.3, 49.5, 19.8, 19.0. LC-MS (ESI$^+$): 599.2 m/z [2M−2Na+3H]$^+$. HRMS (FAB$^+$) calculated for C$_{13}$H$_{17}$NNaO$_5$P, 321.0742; found, 322.0824 [M+H]$^+$.

Sodium hydrogen [(1E)-3-(N-{[4-(propan-2-yl)phenyl]methoxy}acetamido)prop-1-en-1-yl]phosphonate (16e)

White solids (22 mg, 51%). $^1$H NMR (400 MHz, dmso) δ 7.38-7.13 (m, 4H), 6.21-6.03 (m, 1H), 5.87-5.68 (m, 1H), 4.82 (s, 2H), 4.32-4.19 (m, 2H), 2.93-2.80 (m, 1H), 2.01 (s, 3H), 1.18 (d, J=6.8 Hz, 6H). $^{13}$C NMR (101 MHz, dmso) δ 149.4, 136.9, 130.2, 128.6, 127.7 (d, J=189.8 Hz), 126.4, 75.9, 47.7, 33.7, 24.3. LC-MS (ESI$^+$): 328.2 m/z [M−Na+2H]$^+$, 350.2 m/z [M+H]$^+$. HRMS (FAB$^+$) calculated for C$_{15}$H$_{21}$NNaO$_5$P, 349.1055; found, 350.1130 [M+H]$^+$.

Sodium hydrogen [(1E)-3-{N-[(naphthalen-2-yl)methoxy]acetamido}prop-1-en-1-yl]phosphonate (16f)

White solids (20 mg, 95%). $^1$H NMR (400 MHz, d$_2$o) δ 7.94-7.74 (m, 4H), 7.61-7.39 (m, 3H), 6.28-6.07 (m, 1H), 5.90-5.71 (m, 1H), 4.97 (s, 2H), 4.36-4.16 (m, 2H), 1.97 (s, 3H). $^{13}$C NMR (101 MHz, d$_2$o) δ 174.5, 135.9, 133.0, 132.6, 131.1, 129.2, 128.3, 127.9, 127.5, 127.3 (d, J=162.2 Hz), 127.0, 126.8, 126.4, 76.5, 48.3 (d, J=22.0 Hz), 19.2. LC-MS (ESI$^+$): 336.0 m/z [M−Na+2H]$^+$, 671.2 m/z [2M−2Na+3H]$^+$. HRMS (FAB$^+$) calculated for C$_{1-6}$H$_{17}$NNaO$_5$P, 357.0742; found, 358.0820 [M+H]$^+$.

Sodium hydrogen [(1E)-3-{N-[(4-phenylphenyl)methoxy]acetamido}prop-1-en-1-yl]phosphonate (16g)

White solids (24 mg, 66%). $^1$H NMR (400 MHz, cd$_3$od) δ 7.67-7.58 (m, 4H), 7.54-7.30 (m, 5H), 6.64-6.45 (m, 1H), 6.08-5.89 (m, 1H), 4.95 (s, 2H), 4.46-4.38 (m, 2H), 2.12 (s, 3H). $^{13}$C NMR (101 MHz, cd$_3$od) δ 173.2, 141.7, 140.8, 140.3, 133.5, 129.9, 128.5, 127.2, 126.8, 126.6, 123.8 (d, J=182.8 Hz), 76.0, 47.7, 19.1. LC-MS (ESI$^-$): 721.0 m/z [2M−2Na+H]$^-$. HRMS (FAB$^+$) calculated for C$_{18}$H$_{19}$NNaO$_5$P, 383.0899; found, 384.0974 [M+H]$^+$.

Diammonium [(1E)-3-[hydroxy(methoxycarbonyl)amino]prop-1-en-1-yl]phosphonate (12c)

To a solution of 1c (1 eq) in dry CH$_2$Cl$_2$ (0.1 M) under N$_2$ was added TMSBr (10 eq) dropwise at 0° C. The reaction mixture was warmed to room temperature, stirred overnight, and then concentrated under reduced pressure. The mixture was dissolved in CH$_2$Cl$_2$, evaporated under reduced pressure and dried in vacuo. The crude residue was then stirred in 5% NH$_4$OH in H$_2$O at room temperature for 1 h, washed with Et$_2$O (3×) and lyophilized to give the title compounds. Light yellow solids (30 mg, quantitative yield). $^1$H NMR (400 MHz, d$_2$o) δ 6.40-6.06 (m, 1H), 6.01-5.67 (m, 1H), 4.20-4.00 (m, 2H), 3.62 (s, 3H). $^{13}$C NMR (101 MHz, d$_2$o) δ 158.6, 138.0 (d, J=4.7 Hz), 126.0 (d, J=175.2 Hz), 53.6, 52.9 (d, J=22.9 Hz). LC-MS (ESI$^-$): 209.8 m/z [M−2NH$_4$+H]$^-$, 421.0 m/z [2M−4NH$_4$+3H]$^-$. HRMS (ESI$^-$) calculated for C$_5$H$_{16}$N$_3$O$_6$P, 245.0777; found, 210.0169 [M−2NH$_4$+H]$^-$.

General Procedure D for Synthesis of 15d-g

To a solution of 14 (1 eq) in dry CH$_2$Cl$_2$ (0.1 M) in a pressure tube under N$_2$ was added dry Na$_2$CO$_3$ (2 eq), RCH$_2$Br or RCH(CH$_3$)Br (1.2 eq) and NaI (0.1 eq). The reaction mixture was then sealed and stirred at 60° C. for 48 h, filtered and concentrated under reduced pressure. The crude residue was then purified by column chromatography on silica gel using EtOAc and CH$_2$Cl$_2$ to give the pure title compound.

Diethyl [(1E)-3-[N-(1-phenylethoxy)acetamido]prop-1-en-1-yl]phosphonate (15d)

Light yellow oil (63 mg, 25%). $^1$H NMR (400 MHz, cdcl$_3$) δ 7.37-7.25 (m, 5H), 6.50 (ddt, J=22.1, 17.2, 5.2 Hz, 1H), 5.68-5.52 (m, 1H), 4.84-4.72 (m, 1H), 4.29 (m, 1H), 4.08-3.94 (m, 4H), 3.74-3.63 (m, 1H), 2.02 (s, 3H), 1.52 (d, J=6.6 Hz, 3H), 1.29-1.23 (m, 6H). $^{13}$C NMR (101 MHz, cdcl$_3$) δ 173.4, 145.8 (d, J=5.4 Hz), 140.1, 128.9, 128.6, 127.2, 119.4 (d, J=187.8 Hz), 83.3, 61.8 (d, J=5.6 Hz), 49.5 (d, J=25.0 Hz), 20.6, 20.5, 16.3 (d, J=6.3 Hz). LC-MS (ESI$^+$): 356.2 m/z [M+H]$^+$, 711.2 m/z [2M+H]$^+$.

Diethyl [(1E)-3-(N-{[4-(propan-2-yl)phenyl]methoxy}acetamido)prop-1-en-1-yl]phosphonate (15e)

Light yellow oil (56 mg, 26%). $^1$H NMR (400 MHz, cdcl$_3$) δ 7.26-7.16 (m, 4H), 6.66 (ddt, J=22.2, 17.2, 5.3 Hz, 1H), 5.77 (ddt, J=18.8, 17.2, 1.5 Hz, 1H), 4.75 (s, 2H), 4.34-4.25 (m, 2H), 4.08-3.95 (m, 4H), 2.93-2.81 (m, 1H), 2.08 (s, 3H), 1.26 (t, J=7.1 Hz, 6H), 1.21 (d, J=6.9 Hz, 6H). $^{13}$C NMR (101 MHz, cdcl$_3$) δ 150.0, 145.7 (d, J=5.4 Hz), 131.5, 129.3, 126.7, 119.9 (d, J=187.8 Hz), 76.8, 61.8 (d, J=5.6 Hz), 48.5, 33.9, 23.8, 20.3, 16.3 (d, J=6.4 Hz). LC-MS (ESI+): 384.2 m/z [M+H]+.

Diethyl [(1E)-3-{N-[(naphthalen-2-yl)methoxy]acetamido}prop-1-en-1-yl]phosphonate (15f)

Light yellow oil (76 mg, 42%). $^1$H NMR (400 MHz, cdcl$_3$) δ 7.91-7.78 (m, 4H), 7.56-7.41 (m, 3H), 6.72 (ddt, J=22.4, 17.2, 5.2 Hz, 1H), 5.83 (ddt, J=17.2, 12.2, 1.7 Hz, 1H), 5.00 (s, 2H), 4.39-4.34 (m, 2H), 4.11-4.02 (m, 4H), 2.17 (s, 3H), 1.32-1.27 (m, 6H). $^{13}$C NMR (101 MHz, cdcl$_3$) δ 172.8, 145.7 (d, J=5.5 Hz), 133.4, 133.1, 131.6, 128.6, 128.6, 128.0, 127.7, 126.7, 126.5, 126.3, 120.0 (d, J=187.8 Hz), 77.2, 61.9 (d, J=5.5 Hz), 48.8 (d, J=23.2 Hz), 20.5, 16.3 (d, J=6.3 Hz). LC-MS (ESI+): 392.2 m/z [M+H+], 783.2 m/z [2M+H+].

Diethyl [(1E)-3-{N-[(4-phenylphenyl)methoxy]acetamido}prop-1-en-1-yl]phosphonate (15g)

Light yellow oil (158 mg, 38%). $^1$H NMR (400 MHz, cdcl$_3$) δ 7.62-7.55 (m, 4H), 7.47-7.32 (m, 5H), 6.70 (ddt, J=22.4, 17.2, 5.3 Hz, 1H), 5.87-5.76 (m, 1H), 4.86 (s, 2H), 4.39-4.32 (m, 2H), 4.10-4.00 (m, 4H), 2.15 (s, 3H), 1.32-1.26 (m, 6H). $^{13}$C NMR (101 MHz, cdcl$_3$) δ 145.7 (d, J=5.4 Hz), 142.0, 140.3, 133.1, 129.6, 128.8, 127.6, 127.4, 127.1, 120.0 (d, J=187.9 Hz), 76.8, 61.9 (d, J=5.5 Hz), 48.8, 20.4, 16.3 (d, J=6.3 Hz). LC-MS (ESI+): 418.2 m/z [M+H]+, 835.2 m/z [2M+H]+.

General Procedure E for Synthesis of 17a-c

To a solution of 10a-c (1 eq) in dry CH$_2$Cl$_2$ (0.1 M) under N$_2$ was added TMSBr (10 eq) dropwise at 0° C. The reaction mixture was warmed to room temperature, stirred overnight, and then concentrated under reduced pressure. The mixture was dissolved in CH$_2$Cl$_2$, evaporated under reduced pressure and dried under vacuum. The crude residue was then stirred in 0.5 M NaOH (2 eq) in H$_2$O at room temperature for 1 h, washed with Et$_2$O (3×) and lyophilized to give disodium salts as white solids. The crude solid was then dissolved in dry DMF (0.1 M), and TEA (6 eq), chloromethylpivalate (6 eq) and NaI (0.1 eq) were added. The reaction mixture was stirred at 60° C. for 24 h, quenched with H$_2$O, and extracted with Et$_2$O (3×). The combined organic layers were dried with anhydrous Na$_2$SO$_4$, filtered and concentrated under reduced pressure. The crude product was then purified by column chromatography on silica gel using hexanes and EtOAc or CH$_2$Cl$_2$ and EtOAc to give the pure title compound.

({[(1E)-3-[N-(benzyloxy)formamido]prop-1-en-1-yl]({[(2,2-dimethylpropanoyl)oxy]methoxy})phosphoryl}oxy)methyl 2,2-dimethylpropanoate (17a)

Light yellow oil (38 mg, 9%). $^1$H NMR (400 MHz, cdcl$_3$) δ 8.23 (s, 1H), 7.43-7.30 (m, 5H), 6.72 (ddt, J=22.4, 17.2, 5.1 Hz, 1H), 5.96-5.82 (m, 1H), 5.66 (dd, J=13.1, 0.8 Hz, 4H), 4.84 (s, 2H), 4.30-4.20 (m, 2H), 1.21 (s, 18H). $^{13}$C NMR (101 MHz, cdcl$_3$) δ 176.7, 163.2, 146.0 (d, J=6.0 Hz), 129.9, 129.5, 129.3, 128.8, 119.4 (d, J=193.0 Hz), 81.5 (d, J=5.4 Hz), 78.0, 47.0 (d, J=25.8 Hz), 38.7, 26.8. LC-MS (ESI+): 500.2 m/z [M+H]+, 999.2 m/z [2M+H]+.

({[(1E)-3-[N-(benzyloxy)-2,2,2-trifluoroacetamido]prop-1-en-1-yl]({[(2,2-dimethylpropanoyl)oxy]methoxy})phosphoryl}oxy)methyl 2,2-dimethylpropanoate (17b)

Light yellow oil (6 mg, 1%). $^1$H NMR (400 MHz, cdcl$_3$) δ 7.41-7.28 (m, 5H), 6.71 (ddt, J=22.4, 17.2, 5.1 Hz, 1H), 5.95-5.80 (m, 1H), 5.64 (d, J=13.0 Hz, 4H), 4.92 (s, 2H), 4.44-4.31 (m, 2H), 1.18 (s, 18H). $^{13}$C NMR (101 MHz, cdcl$_3$) δ 176.7, 144.4 (d, J=6.2 Hz), 129.4, 129.2, 128.8, 120.0 (d, J=192.2 Hz), 115.9 (q, J=286.7 Hz), 81.5 (d, J=5.3 Hz), 78.5, 49.5 (d, J=26.8 Hz), 38.7, 26.7. LC-MS (ESI+): 568.2 m/z [M+H]+.

({[(1E)-3-[(benzyloxy)(methoxycarbonyl)amino]prop-1-en-1-yl]({[(2,2-dimethylpropanoyl)oxy]methoxy})phosphoryl}oxy)methyl 2,2-dimethylpropanoate (17c)

Light yellow oil (95 mg, 30%). $^1$H NMR (400 MHz, cdcl$_3$) δ 7.43-7.28 (m, 5H), 6.79-6.64 (m, 1H), 5.89-5.77 (m, 1H), 5.67-5.58 (m, 4H), 4.83 (s, 2H), 4.10-4.06 (m, 2H), 3.76 (s, 3H), 1.17 (s, 18H). $^{13}$C NMR (101 MHz, cdcl$_3$) δ 176.7, 157.6, 147.4 (d, J=5.6 Hz), 135.0, 129.4, 128.7, 128.5, 118.5 (d, J=192.6 Hz), 81.5 (d, J=5.5 Hz), 77.6, 53.4, 52.4 (d, J=26.1 Hz), 38.7, 26.8. LC-MS (ESI+): 530.2 m/z [M+H]+.

General Procedure F for Synthesis of 19e-g

To a solution of 16e-g (1 eq) in dry DMF (0.1 M) was added TEA (6 eq), chloromethylpivalate (6 eq) and NaI (0.1 eq). The reaction mixture was stirred at 60° C. for 24 h, quenched with H$_2$O, and extracted with Et$_2$O (3×). The combined organic layers were dried with anhydrous Na$_2$SO$_4$, filtered and concentrated under reduced pressure. The crude product was then purified by column chromatography on silica gel using hexanes and EtOAc or CH$_2$Cl$_2$ and EtOAc to give the pure title compound.

[({[(2,2-dimethylpropanoyl)oxy]methoxy}[(1E)-3-(N-{[4-(propan-2-yl)phenyl]methoxy}acetamido)prop-1-en-1-yl]phosphoryl)oxy]methyl 2,2-dimethylpropanoate (19e)

Light yellow oil (10.6 mg, 8%). $^1$H NMR (400 MHz, cdcl$_3$) δ 7.40-7.16 (m, 4H), 6.83-6.67 (m, 1H), 5.89-5.77 (m, 1H), 5.68-5.59 (m, 4H), 4.76 (s, 2H), 4.36-4.29 (m, 2H), 2.97-2.83 (m, 1H), 2.10 (s, 3H), 1.23 (d, J=6.9 Hz, 6H), 1.18 (s, 18H). $^{13}$C NMR (101 MHz, cdcl$_3$) δ 176.8, 150.1, 147.3 (d, J=5.7 Hz), 131.3, 129.4, 126.8, 118.5 (d, J=192.7 Hz), 81.4 (d, J=5.4 Hz), 76.9, 48.3 (d, J=26.3 Hz), 38.7, 33.9, 26.8, 23.9, 20.3. LC-MS (ESI+): 556.2 m/z [M+H]+. HRMS (FAB+) calculated for C$_{27}$H$_{42}$NO$_9$P, 555.2597; found, 556.2663 [M+H]+.

[({[(2,2-dimethylpropanoyl)oxy]methoxy}[(1E)-3-{N-[(naphthalen-2-yl)methoxy]acetamido}prop-1-en-1-yl]phosphoryl)oxy]methyl 2,2-dimethylpropanoate (19f)

Light yellow oil (16 mg, 12%). $^1$H NMR (400 MHz, cdcl$_3$) δ 7.90-7.76 (m, 4H), 7.54-7.40 (m, 3H), 6.76 (ddt, J=22.5, 17.3, 5.1 Hz, 1H), 5.91-5.79 (m, 1H), 5.67-5.59 (m, 4H), 4.97 (s, 2H), 4.34-4.29 (m, 2H), 2.14 (s, 3H), 1.17 (s, 18H). $^{13}$C NMR (101 MHz, cdcl$_3$) δ 176.7, 147.3 (d, J=5.7 Hz), 133.4, 133.1, 131.6, 128.7, 128.6, 128.0, 127.7, 126.7, 126.5, 126.3, 118.7 (d, J=192.6 Hz), 81.5 (d, J=5.4 Hz), 77.4, 48.8 (d, J=25.0 Hz), 38.7, 26.8, 20.4. LC-MS (ESI$^+$): 564.2 m/z [M+H]$^+$. HRMS (FAB$^+$) calculated for $C_{28}H_{38}NO_9P$, 563.2284; found, 564.2363 [M+H]$^+$.

[({[(2,2-dimethylpropanoyl)oxy]methoxy}[(1E)-3-{N-[(4-phenylphenyl)methoxy]acetamido}prop-1-en-1-yl]phosphoryl)oxy]methyl 2,2-dimethylpropanoate (19g)

Light yellow oil (30 mg, 15%). $^1$H NMR (400 MHz, cdcl$_3$) δ 7.65-7.55 (m, 4H), 7.48-7.32 (m, 5H), 6.78 (ddt, J=22.3, 17.2, 5.1 Hz, 1H), 5.87 (ddt, J=17.2, 12.7, 1.6 Hz, 1H), 5.68-5.61 (m, 4H), 4.85 (s, 2H), 4.38-4.32 (m, 2H), 2.15 (s, 3H), 1.19 (s, 18H). $^{13}$C NMR (101 MHz, cdcl$_3$) δ 176.7, 147.3 (d, J=5.7 Hz), 142.1, 140.3, 133.0, 129.7, 128.8, 127.6, 127.5, 127.1, 118.7 (d, J=192.7 Hz), 81.5 (d, J=5.4 Hz), 77.3, 48.6, 38.7, 26.8, 20.4. LC-MS (ESI$^+$): 590.2 m/z [M+H]$^+$. HRMS (FAB$^+$) calculated for $C_{30}H_{40}NO_9P$, 589.2441; found, 590.2506 [M+H]$^+$.

[({[(2,2-dimethylpropanoyl)oxy]methoxy}(prop-2-en-1-yl)phosphoryl)oxy]methyl 2,2-dimethylpropanoate (20)

To a solution of 6 (5 g, 28 mmol, 1 eq) in dry $CH_2Cl_2$ (30 mL) under $N_2$ at 0° C. was added TMSBr (14.8 mL, 112 mmol, 4 eq) dropwise. The reaction mixture was warmed to room temperature and stirred overnight, and concentrated under reduced pressure. The mixture was dissolved in $CH_2Cl_2$, evaporated under reduced pressure and dried under vacuum. The crude material was then stirred in $CH_3OH$ (93 mL) at room temperature for 1 h, and concentrated under reduced pressure. The crude product was then dissolved in dry DMF (93 mL), to which was added TEA (6 eq), chloromethylpivalate (6 eq) and NaI (0.1 eq). The reaction mixture was stirred at 60° C. for 72 h, quenched with $H_2O$ (100 mL), and extracted with $Et_2O$ (3×100 mL). The combined organic layers were dried with anhydrous $Na_2SO_4$, filtered and concentrated under reduced pressure. The crude product was then purified by column chromatography on silica gel (hexanes/EtOAc=3/1 to 1/1) to give the pure title compound as a colorless oil (5.1 g, 52%) with identical NMR spectroscopic data to that reported previously. $^1$H NMR (400 MHz, cdcl$_3$) δ 5.78-5.62 (m, 5H), 5.28-5.20 (m, 2H), 2.70 (dd, J=22.6, 7.3 Hz, 2H), 1.23 (s, 18H). LC-MS (ESI$^+$): 351.2 m/z [M+H]$^+$, 701.2 m/z [2M+H]$^+$.

{[(2,3-dibromopropyl)({[(2,2-dimethylpropanoyl)oxy]methoxy})phosphoryl]oxy}) {[(2,3-dibromopropyl)({[(2,2-dimethylpropanoyl)oxy]methoxy})phosphoryl]oxy})methyl 2,2-dimethylpropanoate (21)

To a solution of 20 (5.1 g, 14.6 mmol, 1 eq) in dry $CH_2Cl_2$ (100 mL) under $N_2$ at 0° C. was added Bromine (0.9 mL, 17.5 mmol, 1.2 eq) dropwise. The reaction mixture was stirred at room temperature for 1 h, quenched with saturated $Na_2SO_3$ (aq, 100 mL) and extracted with $CH_2Cl_2$ (3×150 mL). The combined organic layers were dried with anhydrous $Na_2SO_4$, filtered, and concentrated under reduced pressure. Chromatographic separation on silica gel (hexanes/EtOAc=3/1) gave the title compound as a colorless oil (5.8 g, 78%). $^1$H NMR (400 MHz, CDCl$_3$) δ 5.81-5.51 (m, 4H), 4.45-4.32 (m, 1H), 3.94-3.86 (m, 1H), 3.78-3.68 (m, 1H), 2.89 (ddd, J=19.6, 15.9, 5.7 Hz, 1H), 2.54-2.41 (m, 1H), 1.23 (s, 18H). $^{13}$C NMR (101 MHz, CDCl$_3$) δ 176.8 (d, J=1.2 Hz), 81.6 (dd, J=6.2, 1.2 Hz), 42.2 (d, J=3.2 Hz), 38.7, 37.4 (d, J=12.8 Hz), 34.6 (d, J=142.9 Hz), 26.8. LC-MS (ESI$^+$): 511.0 m/z [M+H]$^+$.

({[(1E)-3-bromoprop-1-en-1-yl]({[(2,2-dimethylpropanoyl)oxy]methoxy})phosphoryl}oxy)methyl 2,2-dimethylpropanoate (22)

To a suspension of NaH (121 mg, 2.8 mmol, 1.2 eq) in dry THF (10 mL) at 0° C. was added 21 (1.2 g, 2.4 mmol, 1 eq) in dry THF (5 mL) dropwise. The reaction mixture was warmed to room temperature and stirred overnight, quenched with saturated aqueous $NaHCO_3$ (30 mL), and extracted with EtOAc (3×30 mL). The combined organic layers were dried with anhydrous $Na_2SO_4$, filtered, and concentrated under reduced pressure. Chromatographic separation on silica gel (hexanes/EtOAc=5/1 to 2/1) gave the title compound as a colorless oil (704 mg, 70%). $^1$H NMR (400 MHz, CDCl$_3$) δ 6.93-6.76 (m, 1H), 6.04-5.91 (m, 1H), 5.71-5.62 (m, 4H), 4.00-3.96 (m, 2H), 1.21 (s, 18H). $^{13}$C NMR (101 MHz, CDCl$_3$) δ 176.7, 146.8 (d, J=7.0 Hz), 120.4 (d, J=191.5 Hz), 81.5 (d, J=5.4 Hz), 38.7, 26.8. LC-MS (ESI$^+$): 429.0, 431.0 m/z [M+H]$^+$.

O-Benzylhydroxylamine (23)

To a suspension of O-benzylhydroxylamine hydrochloride (5 g, 31 mmol, 1 eq) in $Et_2O$ (125 mL) was added 5% aqueous NaOH (45 mL). The reaction mixture was stirred at room temperature for 30 min. The organic layer was separated and the aqueous layer was extracted with $Et_2O$ (2×50 mL). The combined organic layers were dried with anhydrous $Na_2SO_4$, filtered, and concentrated under reduced pressure to afford the title compound as a colorless liquid (3.8 g, 97%) with identical NMR spectroscopic data to that reported previously. $^1$H NMR (400 MHz, cdcl$_3$) δ 7.40-7.27 (m, 5H), 5.39 (bs, 2H), 4.69 (s, 2H). GC-MS (EI) 123 m/z [M].

({[(1E)-3-[(benzyloxy)amino]prop-1-en-1-yl]({[(2,2-dimethylpropanoyl)oxy]methoxy}) phosphoryl}oxy)methyl 2,2-dimethylpropanoate (24)

To a solution of 22 (2.8 g, 6.5 mmol, 1 eq) in dry THF (50 mL) was added 23 (980 mg, 8 mmol, 1.2 eq) and TEA (1.73 mL, 13 mmol, 2 eq). The reaction mixture was stirred at reflux for 3 h, and then concentrated under reduced pressure. Chromatographic separation on silica gel (hexanes/EtOAc=2/1 to 1/2) gave the title compound as a colorless oil (1.0 g, 34%). $^1$H NMR (400 MHz, CDCl$_3$) δ 7.41-7.26 (m, 5H), 6.87 (ddt, 1H), 6.02-5.85 (m, 1H), 5.70-5.62 (m, 4H), 4.68 (s, 2H), 3.67-3.63 (m, 2H), 1.21 (s, 18H). $^{13}$C NMR (101 MHz, CDCl$_3$) δ 176.8, 150.1 (d, J=5.3 Hz), 137.5, 128.4, 128.4, 128.0, 117.8 (d, J=192.1 Hz), 81.5 (d, J=5.5 Hz), 76.4, 54.0 (d, J=24.2 Hz), 38.7, 26.8. LC-MS (ESI$^+$): 472.2 m/z [M+H]$^+$, 943.2 m/z [2M+H]$^+$.

Optimized synthesis for ({[(1E)-3-[N-(benzyloxy)formamido]prop-1-en-1-yl]({[(2,2-dimethylpropanoyl)oxy]methoxy})phosphoryl}oxy)methyl 2,2-dimethylpropanoate (17a)

To a suspension of 1,1'-carbonyldiimidazole (688 mg, 4.3 mmol, 2 eq) in $CH_2Cl_2$ (3 mL) was added formic acid (0.16 mL, 4.3 mmol, 2 eq) dropwise at room temperature. The mixture was stirred at room temperature for 5 min, and then transferred dropwise to a solution of 24 (1.0 g, 2.1 mmol, 1 eq) and TEA (0.85 mL, 6.4 mmol, 3 eq) in CH$_2$Cl$_2$ (15 mL) at 0° C. The reaction mixture was stirred at 0° C. for 30 min, quenched with saturated aqueous NaHCO$_3$ (30 mL) and extracted with CH$_2$Cl$_2$ (3×50 mL). The combined organic layers were dried with anhydrous Na$_2$SO$_4$, filtered, and concentrated under reduced pressure. Chromatographic separation on silica gel (hexanes/EtOAc=2/1 to 1/3) gave the title compound as a light yellow oil (862 mg, 82%). $^1$H NMR (400 MHz, CDCl$_3$) δ 8.23 (s, 1H), 7.43-7.30 (m, 5H), 6.72 (ddt, J=22.4, 17.2, 5.1 Hz, 1H), 5.96-5.82 (m, 1H), 5.66 (dd, J=13.1, 0.8 Hz, 4H), 4.84 (s, 2H), 4.30-4.20 (m, 2H), 1.21 (s, 18H). $^{13}$C NMR (101 MHz, CDCl$_3$) δ 176.7, 163.2, 146.0 (d, J=6.0 Hz), 129.9, 129.5, 129.3, 128.8, 119.4 (d, J=193.0 Hz), 81.5 (d, J=5.4 Hz), 78.3, 47.0 (d, J=25.8 Hz), 38.7, 26.8. LC-MS (ESI$^+$): 500.2 m/z [M+H]$^+$, 999.2 m/z [2M+H]$^+$.

Optimized synthesis for ({[(1E)-3-[N-(benzyloxy)-2,2,2-trifluoroacetamido]prop-1-en-1-yl]({[(2,2-dimethylpropanoyl)oxy]methoxy})phosphoryl}oxy) methyl 2,2-dimethylpropanoate (17b)

To a solution of 24 (60 mg, 0.13 mmol, 1 eq) in CH$_2$Cl$_2$ (2 mL) at 0° C. was added TEA (0.025 mL, 0.19 mmol, 1.5 eq) and trifluoroacetic anhydride (0.02 mL, 0.15 mmol, 1.2 eq) dropwise. The reaction mixture was stirred at 0° C. for 15 min, quenched with saturated aqueous NaHCO$_3$ (3 mL), and extracted with CH$_2$Cl$_2$ (3×5 mL). The combined organic layers were dried with anhydrous Na$_2$SO$_4$, filtered, and concentrated under reduced pressure. Chromatographic separation on silica gel (hexanes/EtOAc=5/1 to 1/1) gave the title compound as a white solid (53 mg, 73%). $^1$H NMR (400 MHz, CDCl$_3$) δ 7.41-7.28 (m, 5H), 6.71 (ddt, J=22.4, 17.2, 5.1 Hz, 1H), 5.95-5.80 (m, 1H), 5.64 (d, J=13.0 Hz, 4H), 4.92 (s, 2H), 4.44-4.31 (m, 2H), 1.18 (s, 18H). $^{13}$C NMR (101 MHz, CDCl$_3$) δ 176.7, 144.4 (d, J=6.2 Hz), 129.4, 129.2, 128.8, 120.0 (d, J=192.2 Hz), 115.9 (q, J=286.7 Hz), 81.5 (d, J=5.3 Hz), 78.5, 49.5 (d, J=26.8 Hz), 38.7, 26.7. LC-MS (ESI$^+$): 568.2 m/z [M+H]$^+$.

Diethyl (prop-2-en-1-yl)phosphonate (25)

Triethyl phosphite (10 mL, 58 mmol, 1 eq) and Allyl bromide (6.5 mL, 75 mmol, 1.3 eq) were added to an oven-dried round bottom flask covered with foil. The reaction mixture was stirred at 60° C. for 2 days, purified by fractional distillation under reduced pressure using a Kugelrohr to afford the title compound as a colorless oil (8.8 g, 85%). $^1$H NMR (400 MHz, cdcl$_3$) δ 5.95-5.69 (m, 1H), 5.31-5.13 (m, 2H), 4.25-3.99 (m, 4H), 2.62 (ddt, J=21.9, 7.4, 1.3 Hz, 2H), 1.32 (t, J=7.1 Hz, 6H). $^{13}$C NMR (101 MHz, cdcl$_3$) δ 127.7 (d, J=11.3 Hz), 120.0 (d, J=14.4 Hz), 62.1 (d, J=6.5 Hz), 32.0 (d, J=139.4 Hz), 16.3 (d, J=6.0 Hz). GC-MS (EI): 178 m/z [M].

Diethyl (2,3-dibromopropyl)phosphonate (26)

To a solution of 25 (2.9 g, 16 mmol, 1 eq) in dry CH$_2$Cl$_2$ (30 mL) under N$_2$ was added Bromine (1 mL, 19.6 mmol, 1.2 eq) at 0° C. dropwise. The reaction mixture was stirred at room temperature for 2 h, quenched with saturated Na$_2$SO$_3$ (aq, 30 mL) and extracted with CH$_2$Cl$_2$ (3×30 mL). The combined organic layers were dried with anhydrous Na$_2$SO$_4$, filtered, and concentrated to afford the title compound as a light yellow oil (4.9 g, 88%) without further purification. $^1$H NMR (400 MHz, cdcl$_3$) δ 4.49-4.37 (m, 1H), 4.23-4.07 (m, 4H), 3.93 (ddd, J=10.8, 4.4, 2.1 Hz, 1H), 3.78 (dd, J=10.8, 7.3 Hz, 1H), 2.78 (ddd, J=18.8, 15.8, 6.1 Hz, 1H), 2.39 (ddd, J=18.4, 15.8, 7.3 Hz, 1H), 1.37-1.32 (m, 6H). $^{13}$C NMR (101 MHz, cdcl$_3$) δ 62.2 (dd, J=21.6, 6.6 Hz), 43.4 (d, J=2.8 Hz), 38.0 (d, J=11.1 Hz), 33.9 (d, J=141.3 Hz), 16.4 (dd, J=6.1, 3.5 Hz). LC-MS (ESI$^+$): 337.0, 339.0, 341.0 m/z [M+H]$^+$.

tert-Butyl N-(benzyloxy)carbamate (27)

To a stirred solution of O-benzylhydroxylamine hydrochloride (9.6 g, 60 mmol, 1 eq) and triethylamine (9.0 mL, 66 mmol, 1.1 eq) in a 1:1 mixture of THF/H$_2$O (100 mL), di-tert-butyl dicarbonate (30% in dioxane, 43.7 mL, 60 mmol, 1 eq) was added. The reaction mixture was stirred at room temperature for 2.5 h, concentrated to eliminate THF. The residue was extracted with EtOAc (3×50 mL), washed with 0.5 M citric acid (aq, 2×50 mL) and H$_2$O (50 mL). The organic layer was dried with anhydrous Na$_2$SO$_4$, filtered and concentrated. The crude was crystallized in Hexanes to afford the title compound as a white solid (12 g, 90%). $^1$H NMR (400 MHz, CDCl$_3$) δ 7.97-7.29 (m, 5H), 5.28 (s, 2H), 1.90 (s, 9H). $^{13}$C NMR (101 MHz, cdcl$_3$) δ 156.7, 135.7, 129.1, 128.5, 81.7, 78.4, 28.2. LC-MS (ESI$^+$): 245.9 m/z [M+Na]$^+$, 460.0 m/z [2M+Na]$^+$.

tert-butyl N-(benzyloxy)-N-[(2E)-3-(diethoxyphosphoryl)prop-2-en-1-yl]carbamate (28)

To a solution of 27 (1.2 g, 5.4 mmol, 1 eq) in dry THF (15 mL) under N$_2$ was added a suspension of NaH (60% in oil, 430 mg, 10.8 mmol, 2 eq) in dry THF (10 mL) at 0° C. dropwise. This mixture was stirred at 0° C. for 30 min and was added 26 (2 g, 5.9 mmol, 1.1 eq) in dry THF (3 mL) and NaI (16 mg, 0.11 mmol, 0.02 eq) at 0° C. The reaction mixture was stirred at room temperature for 20 h, quenched with saturated NaHCO$_3$ (aq, 30 mL), concentrated to eliminate THF and extracted with EtOAc (3×30 mL). The combined organic layers were dried with anhydrous Na$_2$SO$_4$, filtered and concentrated. Chromatographic separation on silica gel (EtOAc/CH$_2$Cl$_2$=2/1) gave the title compound as a light yellow oil (1.6 g, 77%). $^1$H NMR (400 MHz, cdcl$_3$) δ 7.39-7.31 (m, 5H), 6.69 (ddt, J=22.4, 17.2, 5.3 Hz, 1H), 5.82 (ddt, J=18.9, 17.2, 1.7 Hz, 1H), 4.83 (s, 2H), 4.12-4.02 (m, 6H), 1.49 (s, 9H), 1.31-1.27 (m, 6H). $^{13}$C NMR (101 MHz, cdcl$_3$) δ 156.3, 146.4 (d, J=5.3 Hz), 135.4, 129.3, 128.6, 128.4, 119.5 (d, J=187.6 Hz), 82.0, 61.8 (d, J=5.6 Hz), 52.5 (d, J=24.6 Hz), 28.2, 16.3 (d, J=6.5 Hz). LC-MS (ESI$^+$): 799.2 m/z [2M+H]$^+$.

General Procedure a for Synthesis of Amide 29a-d

To a solution of MeOH (10.1 eq) in dry CH$_2$Cl$_2$ (1 M) under N$_2$ was added Acetyl chloride (10 eq) dropwise at room temperature and the mixture was stirred for 10 min. The reaction mixture was then added a solution of 28 (1 eq) in dry CH$_2$Cl$_2$ (1 M) and was stirred at room temperature for 30 min. After the completion of deprotection, dry Na$_2$CO$_3$ (12 eq) was added at 0° C. and the mixture was stirred at the same temperature for 10 min. The reaction mixture was then added RCOCl (2 eq) slowly, warmed up to room temperature and stirred for 30 min to 24 h, quenched with saturated NaHCO$_3$ (aq) and extracted with CH$_2$Cl$_2$ (3×). The combined organic layers were dried with anhydrous Na$_2$SO$_4$, filtered and concentrated. The crude was then purified by column chromatography on silica gel using EtOAc and CH$_2$Cl$_2$ to give the pure title compound.

Diethyl [(1E)-3-[N-(benzyloxy)-1-phenylformamido]prop-1-en-1-yl]phosphonate (29a)

Light yellow oil (831 mg, 82%). $^1$H NMR (400 MHz, cdcl$_3$) δ 7.71-7.00 (m, 10H), 6.89-6.70 (m, 1H), 6.24-5.98 (m, 1H), 4.64 (s, 2H), 4.48 (m, 2H), 4.20-3.98 (m, 4H), 1.37-1.23 (m, 6H). $^{13}$C NMR (101 MHz, cdcl$_3$) δ 170.2, 145.8, 133.8, 133.6, 130.9, 129.4, 128.9, 128.5, 128.3, 128.1, 62.1, 49.9, 16.4. LC-MS (ESI$^+$): 404.2 m/z [M+H]$^+$, 807.2 m/z [2M+H]$^+$.

Diethyl [(1E)-3-[N-(benzyloxy)-2-phenylacetamido]prop-1-en-1-yl]phosphonate (29b)

Light yellow oil (353 mg, 85%). $^1$H NMR (400 MHz, cdcl$_3$) δ 7.43-7.11 (m, 10H), 6.63 (ddt, J=22.3, 17.2, 5.2 Hz, 1H), 5.69 (ddt, J=18.8, 17.2, 1.6 Hz, 1H), 4.73 (s, 2H), 4.38-4.28 (m, 2H), 4.03-3.90 (m, 4H), 3.71 (s, 2H), 1.23 (ddd, J=5.6, 4.6, 2.0 Hz, 6H). $^{13}$C NMR (101 MHz, cdcl$_3$) δ 173.2, 145.5 (d, J=5.5 Hz), 134.4, 134.1, 129.3, 129.2, 129.1, 128.7, 128.5, 126.9, 119.9 (d, J=187.1 Hz), 77.0, 61.8 (d, J=5.6 Hz), 48.6 (d, J=23.2 Hz), 39.5, 16.3 (d, J=6.4 Hz). LC-MS (ESI$^+$): 418.2 m/z [M+H]$^+$, 835.2 m/z [2M+H]$^+$.

Diethyl [(1E)-3-[N-(benzyloxy)-3-phenylpropanamido]prop-1-en-1-yl]phosphonate (29c)

Light yellow oil (224 mg, 69%). $^1$H NMR (400 MHz, cdcl$_3$) δ 7.43-7.12 (m, 10H), 6.80-6.59 (m, 1H), 6.01-5.79 (m, 1H), 4.71 (s, 2H), 4.42-4.28 (m, 2H), 4.15-4.00 (m, 4H), 2.93 (t, J=7.6 Hz, 2H), 2.75 (t, J=7.5 Hz, 2H), 1.41-1.23 (m, 6H). $^{13}$C NMR (101 MHz, cdcl$_3$) δ 174.5, 145.9, 141.0, 134.2, 129.1, 129.0, 128.7, 128.5, 128.4, 126.2, 77.1, 62.0, 48.9, 34.1, 30.6, 16.4. LC-MS (ESI$^+$): 432.2 m/z [M+H]$^+$, 863.2 m/z [2M+H]$^+$.

Diethyl [(1E)-3-[N-(benzyloxy)-4-phenylbutanamido]prop-1-en-1-yl]phosphonate (29d)

Light yellow oil (309 mg, 69%). $^1$H NMR (CDCl$_3$, 400 MHz) δ (ppm): 7.37-7.16 (m, 10H), 6.76-6.64 (m, 1H), 5.85-5.75 (m, 1H), 4.73 (s, 2H), 4.34 (m, 2H), 4.12-4.00 (m, 4H), 2.68-2.62 (m, 2H), 2.45-2.41 (t, 1H, J=7.2, 8.0 Hz), 2.36-2.32 (t, 1H, J=7.2, 7.6 Hz), 1.99-1.91 (m, 2H), 1.30-1.27 (t, 6H, J=6.8, 7.2 Hz). $^{13}$C NMR (CDCl$_3$, 100 MHz) δ (ppm): 177.3, 146.1, 129.2, 129.1, 128.8, 128.7, 128.6, 128.6, 128.5, 128.5, 128.4, 126.3, 126.0, 119.7 (d, J=187.4 Hz), 76.8, 62.0, 48.8 (d, J=22.8 Hz), 35.1, 33.3, 31.5, 25.9, 16.3. LC-MS (ESI$^+$): 446.2 m/z [M+H]$^+$, 891.2 m/z [2M+H]$^+$.

General Procedure B for Synthesis of 31a-d, and 33a-b, d

To a solution of 29a-d, or 34a-b, d (1 eq) in dry CH$_2$Cl$_2$ (0.1 M) under N$_2$ was added boron trichloride (1M in CH$_2$Cl$_2$, 4 eq) at −78° C. dropwise. The reaction mixture was stirred at −78° C. for 30 min to 3 h, quenched with saturated NaHCO$_3$ (aq) and extracted with EtOAc (5×). The combined organic layers were dried with anhydrous Na$_2$SO$_4$, filtered and concentrated. The crude was then purified by column chromatography on silica gel using EtOAc and MeOH (EtOAc and CH$_2$Cl$_2$ for 33a-b, d) to give the pure title compound.

Diethyl [(1E)-3-(N-hydroxy-1-phenylformamido)prop-1-en-1-yl]phosphonate (31a)

Light yellow oil (229 mg, 74%). $^1$H NMR (400 MHz, cdcl$_3$) δ 9.85 (s, 1H), 7.67-7.26 (m, 5H), 6.89-6.65 (m, 1H), 6.04-5.78 (m, 1H), 4.52-4.32 (m, 2H), 3.97-3.86 (m, 4H), 1.36-1.06 (m, 6H). $^{13}$C NMR (101 MHz, cdcl$_3$) δ 169.84, 146.94, 133.29, 130.71, 128.38, 127.94, 118.61 (d, J=186.1 Hz), 62.10 (d, J=5.7 Hz), 52.34, 16.21 (d, J=6.5 Hz). LC-MS (ESI$^+$): 314.2 m/z [M+H]$^+$, 627.2 m/z [2M+H]$^+$.

Diethyl [(1E)-3-(N-hydroxy-2-phenylacetamido)prop-1-en-1-yl]phosphonate (31b)

Light yellow oil (224 mg, 81%). $^1$H NMR (400 MHz, cdcl$_3$) δ 9.91 (s, 1H), 7.41-7.23 (m, 5H), 6.80-6.64 (m, 1H), 5.92-5.77 (m, 1H), 4.43-4.38 (m, 2H), 4.11-3.99 (m, 4H), 3.88 (s, 2H), 1.38-1.29 (m, 6H). $^{13}$C NMR (101 MHz, cdcl$_3$) δ 172.9, 147.3 (d, J=4.7 Hz), 135.2, 129.6, 128.4, 126.8, 118.1 (d, J=188.9 Hz), 62.4 (d, J=5.6 Hz), 50.7 (d, J=24.9 Hz), 39.1, 16.3 (d, J=6.3 Hz). LC-MS (ESI$^+$): 328.2 m/z [M+H]$^+$, 655.2 m/z [2M+H]$^+$.

Diethyl [(1E)-3-(N-hydroxy-3-phenylpropanamido)prop-1-en-1-yl]phosphonate (31c)

Light yellow oil (103 mg, 66%). $^{11}$H NMR (400 MHz, cdcl$_3$) δ 9.70 (s, 1H), 7.31-7.12 (m, 5H), 6.67 (ddd, J=22.1, 9.9, 4.9 Hz, 1H), 5.81 (ddd, J=17.2, 10.9, 9.4 Hz, 1H), 4.43-4.32 (m, 2H), 4.04-3.91 (m, 4H), 2.97-2.89 (m, 2H), 2.87-2.79 (m, 1H), 1.29-1.21 (m, 6H). $^{13}$C NMR (101 MHz, cdcl$_3$) δ 174.1, 147.7 (d, J=4.6 Hz), 141.4, 128.4, 128.3, 126.0, 118.0 (d, J=188.7 Hz), 62.3 (d, J=5.7 Hz), 50.5 (d, J=25.2 Hz), 34.1, 30.5, 16.2 (d, J=6.4 Hz). LC-MS (ESI$^+$): 342.2 m/z [M+H]$^+$, 683.2 m/z [2M+H]$^+$.

Diethyl [(1E)-3-(N-hydroxy-4-phenylbutanamido)prop-1-en-1-yl]phosphonate (31d)

Light yellow oil (73 mg, 51%). $^1$H NMR (400 MHz, cdcl$_3$) δ 9.52 (bs, 1H), 7.09-7.28 (m, 5H), 6.64-6.82 (m, 1H), 5.80-5.89 (m, 1H), 4.39 (bs, 2H), 3.93-4.12 (m, 4H), 2.66 (t, J=7.2, 8.0 Hz, 2H), 2.51-2.58 (m, 2H), 1.93-2.00 (m, 2H), 1.28 (t, J=7.2 Hz, 6H). $^{13}$C NMR (101 MHz, cdcl$_3$) δ 174.8, 147.8, 128.3, 125.9, 118.0 (d, J=189.5 Hz), 162.2, 50.6 (d, J=25.1 Hz), 35.2, 31.8, 26.0, 16.2 (d, J=6.4 Hz). LC-MS (ESI$^+$): 356.2 m/z [M+H]$^+$, 711.2 m/z [2M+H]$^+$.

[({[(2,2-dimethylpropanoyl)oxy]methoxy}[(1E)-3-(N-hydroxy-1-phenylformamido)prop-1-en-1-yl]phosphoryl)oxy]methyl 2,2-dimethylpropanoate (33a)

Light yellow oil (27 mg, 30%). $^1$H NMR (400 MHz, cdcl$_3$) δ 8.69 (s, 1H), 7.57-7.34 (m, 5H), 6.82 (ddt, J=21.8, 17.2, 4.5 Hz, 1H), 6.04 (ddt, J=20.6, 17.2, 1.7 Hz, 1H), 5.67-5.60 (m, 4H), 4.45-4.38 (m, 2H), 1.19 (s, 18H). $^{13}$C NMR (101 MHz, cdcl$_3$) δ 176.9, 167.7, 146.8, 131.3, 128.7, 128.5, 128.0, 118.7 (d, J=192.4 Hz), 81.5 (d, J=5.2 Hz), 52.7 (d, J=24.3 Hz), 38.7, 26.8. LC-MS (ESI$^+$): 486.2 m/z [M+H]$^+$, 971.2 m/z [2M+H]$^+$. HRMS (FAB$^+$) calculated for C$_{22}$H$_{32}$NO$_9$P, 485.1815; found, 486.1877 [M+H]$^+$.

[({[(2,2-dimethylpropanoyl)oxy]methoxy}[(1E)-3-(N-hydroxy-2-phenylacetamido)prop-1-en-1-yl]phosphoryl)oxy]methyl 2,2-dimethylpropanoate (33b)

Light yellow oil (54 mg, 49%). $^1$H NMR (400 MHz, cdcl$_3$) δ 8.94 (s, 1H), 7.34-7.17 (m, 5H), 6.79-6.61 (m, 1H), 5.90-5.76 (m, 1H), 5.64-5.54 (m, 4H), 4.38-4.31 (m, 2H), 3.81 (s, 2H), 1.18 (s, 18H). $^{13}$C NMR (101 MHz, cdcl$_3$) δ 177.0, 173.0, 148.4, 134.9, 129.5, 128.4, 126.7, 117.7 (d, J=192.3 Hz), 81.5 (d, J=5.3 Hz), 50.4 (d, J=26.4 Hz), 39.3, 38.7, 26.8. LC-MS (ESI$^+$): 500.2 m/z [M+H]$^+$, 999.2 m/z [2M+H]$^+$. HRMS (FAB$^+$) calculated for C$_{23}$H$_{34}$NO$_9$P, 499.1971; found, 500.2037 [M+H]$^+$.

[({[(2,2-dimethylpropanoyl)oxy]methoxy}[(1E)-3-(N-hydroxy-4-phenylbutanamido)prop-1-en-1-yl]phosphoryl)oxy]methyl 2,2-dimethylpropanoate (33d)

Light yellow oil (9 mg, 26%). $^1$H NMR (400 MHz, cdcl$_3$) δ 7.34-7.05 (m, 5H), 6.83-6.66 (m, 1H), 5.93-5.80 (m, 1H), 5.67-5.59 (m, 4H), 4.44-4.29 (m, 2H), 2.69-2.62 (m, 2H), 2.58-2.45 (m, 2H), 2.01-1.90 (m, 2H), 1.19 (s, 18H). $^{13}$C NMR (101 MHz, cdcl$_3$) δ 177.2, 148.5, 130.8, 128.4, 128.3, 125.9, 118.0 (d, J=186.3 Hz), 81.5 (d, J=5.0 Hz), 50.3 (d, J=24.8 Hz), 38.7, 35.3, 31.7, 29.7, 26.8. LC-MS (ESI$^+$): 528.2 m/z [M+H]$^+$. HRMS (FAB$^+$) calculated for C$_{25}$H$_{38}$NO$_9$P, 527.2284; found, 528.2352 [M+H]$^+$.

General Procedure C for Synthesis of 32a-d

To a solution of 31a-d (1 eq) in dry CH$_2$Cl$_2$ (0.1 M) under N$_2$ was added TMSBr (10 eq) dropwise at 0° C. The reaction mixture was warmed to room temperature and stirred overnight, concentrated. The mixture was dissolved in CH$_2$Cl$_2$, evaporated and dried under vacuum. The crude was then stirred in 0.5 M NaOH (1 eq) in H$_2$O at room temperature for 1 h, washed with Et$_2$O three times and lyophilized to give the title compounds.

Sodium hydrogen [(1E)-3-(N-hydroxy-1-phenylformamido)prop-1-en-1-yl]phosphonate (32a)

Light yellow solids (23 mg, quantitative yield). $^1$H NMR (400 MHz, cd$_3$od) δ 7.52-7.38 (m, 5H), 6.45-6.31 (m, 1H), 6.13-6.00 (m, 1H), 4.43-4.26 (m, 2H). $^{13}$C NMR (101 MHz, cd$_3$od) δ 170.1, 135.7 (d, J=4.7 Hz), 134.2, 130.2, 129.0 (d, J=173.7 Hz), 127.8, 127.7, 52.6. LC-MS (ESI$^-$): 256 m/z [M−Na]$^-$. HRMS (ESI$^-$) calculated for C$_{10}$H$_{11}$NNaO$_5$P, 279.0273; found, 256.0377 [M−Na]$^-$.

Sodium hydrogen [(1E)-3-(N-hydroxy-2-phenylacetamido)prop-1-en-1-yl]phosphonate (32b)

Light yellow solids (42 mg, 96%). $^1$H NMR (400 MHz, d$_2$o) δ 7.46-7.25 (m, 5H), 6.52-6.37 (m, 1H), 5.98-5.80 (m, 1H), 4.44-4.31 (m, 2H), 3.92 (s, 2H). $^{13}$C NMR (101 MHz, d$_2$o) δ 174.5, 140.6, 134.9, 129.4, 128.9, 127.2, 123.2 (d, J=179.0 Hz), 51.0 (d, J=23.6 Hz), 38.8. LC-MS (ESI$^+$): 272.0 m/z [M−Na+2H]$^+$, 543.2 m/z [2M−2Na+3H]$^+$. HRMS (FAB$^+$) calculated for C$_{11}$H$_{13}$NNaO$_5$P, 293.0429; found, 294.0508 [M+H]$^+$.

Sodium hydrogen [(1E)-3-(N-hydroxy-3-phenylpropanamido)prop-1-en-1-yl]phosphonate (32c)

Light yellow solids (51 mg, 92%). $^1$H NMR (400 MHz, d$_2$o) δ 7.26-7.09 (m, 5H), 6.29-6.13 (m, 1H), 5.77-5.59 (m, 1H), 4.22-4.11 (m, 2H), 2.85-2.66 (m, 4H). $^{13}$C NMR (101 MHz, d$_2$o) δ 175.3, 140.7, 139.3 (d, J=5.3 Hz), 128.7, 128.3, 126.4, 124.0 (d, J=177.7 Hz), 50.8 (d, J=23.6 Hz), 33.1, 30.2. LC-MS (ESI$^+$): 571.2 m/z [2M−2Na+3H]$^+$. HRMS (FAB$^+$) calculated for C$_{12}$H$_{15}$NNaO$_5$P, 307.0586; found, 308.0655 [M+H]$^+$.

Sodium hydrogen [(1E)-3-(N-hydroxy-4-phenylbutanamido)prop-1-en-1-yl]phosphonate (32d)

Light yellow solids (28 mg, 77%). $^1$H NMR (400 MHz, cdcl$_3$) δ 7.12-7.25 (m, 5H), 6.30-6.41 (m, 1H), 5.75-5.85 (m, 1H), 4.22 (bs, 2H), 2.52-2.57 (m, 2H), 2.25 (t, J=7.3 Hz, 2H), 1.76-1.83 (m, 2H). $^{13}$C NMR (101 MHz, d$_2$o) δ 176.5, 142.1, 133.0 (d, J=5.5 Hz), 130.4, 128.8, 126.3, 121.9 (d, J=180.7 Hz), 50.9 (d, J=23.5 Hz), 34.6, 31.2, 26.1. LC-MS (ESI$^+$): 300.0 m/z [M−Na+2H]$^+$, 599.2 m/z [2M−2Na+3H]$^+$, 898.2 m/z [3M−3Na+4H]$^+$. HRMS (FAB$^+$) calculated for C$_{13}$H$_{17}$NNaO$_5$P, 321.0742; found, 322.0862 [M+H]$^+$.

General Procedure D for Synthesis of 34a-b, d

To a solution of 29a-b, d (1 eq) in dry CH$_2$Cl$_2$ (0.1 M) under N$_2$ was added TMSBr (10 eq) dropwise at 0° C. The reaction mixture was warmed to room temperature and stirred overnight, concentrated. The mixture was dissolved in CH$_2$Cl$_2$, evaporated and dried under vacuum. The crude was then stirred in 0.5 M NaOH (2 eq) in H$_2$O at room temperature for 1 h, washed with Et$_2$O (3×) and lyophilized to give disodium salts as white solids. The crude solids was then dissolved in dry DMF (0.1 M), added TEA (6 eq), chloromethylpivalate (6 eq) and NaI (0.1 eq). The reaction mixture was stirred at 60° C. for 24 h, quenched with H$_2$O, extracted with Et$_2$O (3×). The combined organic layers were dried with anhydrous Na$_2$SO$_4$, filtered and concentrated. The crude was then purified by column chromatography on silica gel using Hexanes and EtOAc or CH$_2$Cl$_2$ and EtOAc to give the pure title compound.

({[(1E)-3-[N-(benzyloxy)-1-phenylformamido]prop-1-en-1-yl]({[(2,2-dimethylpropanoyl)oxy]methoxy})phosphoryl}oxy)methyl 2,2-dimethylpropanoate (34a)

Light yellow oil (182 mg, 32%). $^1$H NMR (400 MHz, cdcl$_3$) δ 7.74-7.01 (m, 10H), 6.95-6.77 (m, 1H), 6.08-5.93 (m, 1H), 5.75-5.58 (m, 4H), 4.65 (s, 2H), 4.51-4.46 (m, 2H), 1.20 (s, 18H). $^{13}$C NMR (101 MHz, cdcl$_3$) δ 176.7, 170.1, 147.2 (d, J=6.0 Hz), 133.6, 133.5, 130.9, 129.4, 128.9, 128.4, 128.3, 128.0, 118.6 (d, J=192.6 Hz), 81.5 (d, J=5.4 Hz), 77.0, 49.5 (d, J=25.4 Hz), 38.6, 26.7. LC-MS (ESI$^+$): 576.2 m/z [M+H]$^+$.

({[(1E)-3-[N-(benzyloxy)-2-phenylacetamido]prop-1-en-1-yl]({[(2,2-dimethylpropanoyl)oxy]methoxy})phosphoryl}oxy)methyl 2,2-dimethylpropanoate (34b)

Light yellow oil (145 mg, 35%). $^1$H NMR (400 MHz, cdcl$_3$) δ 7.43-7.15 (m, 10H), 6.80-6.65 (m, 1H), 5.77 (ddt, J=17.2, 4.7, 1.7 Hz, 1H), 5.68-5.55 (m, 4H), 4.74 (s, 2H), 4.38-4.29 (m, 2H), 3.73 (s, 2H), 1.18 (s, 18H). $^{13}$C NMR (101 MHz, cdcl$_3$) δ 176.7, 147.2 (d, J=5.7 Hz), 137.2, 129.3, 129.2, 129.1, 128.8, 128.5, 128.4, 127.0, 118.7 (d, J=192.4

Hz), 81.4 (d, J=5.4 Hz), 48.7 (d, J=27.8 Hz), 39.5, 38.7, 26.8. LC-MS (ESI+): 590.2 m/z [M+H]+.

({[(1E)-3-[N-(benzyloxy)-4-phenylbutanamido]prop-1-en-1-yl]({[(2,2-dimethylpropanoyl)oxy]methoxy})phosphoryl}oxy)methyl 2,2-dimethylpropanoate (34d)

Light yellow oil (50 mg, 18%). $^1$H NMR (400 MHz, cdcl$_3$) δ 7.38-7.11 (m, 10H), 6.73 (ddt, J=22.7, 17.4, 5.2 Hz, 1H), 5.88-5.75 (m, 1H), 5.66-5.59 (m, 4H), 4.70 (s, 2H), 4.34-4.28 (m, 2H), 2.62 (t, J=7.5 Hz, 2H), 2.40 (t, J=7.5 Hz, 2H), 1.92 (dt, J=14.9, 7.6 Hz, 2H), 1.17 (s, 18H). $^{13}$C NMR (101 MHz, cdcl$_3$) δ 176.7, 147.5 (d, J=5.6 Hz), 141.5, 134.1, 129.2, 129.0, 128.7, 128.5, 128.3, 125.9, 118.6 (d, J=192.6 Hz), 81.5 (d, J=5.4 Hz), 77.1, 48.7 (d, J=26.9 Hz), 38.7, 35.2, 31.5, 29.6, 26.8. LC-MS (ESI+): 618.2 m/z [M+H]+.

Bacterial Strains and Growth Conditions

Recombinant protein was expressed in *Escherichia coli* Rosetta2(DE3) cells obtained from Novagen (San Diego, Calif.). *E. coli* was cultured at 37° C. in Luria-Bertani (LB) media supplemented with 100 µg/mL ampicillin and 34 µg/ml chloramphenicol with constant shaking at 250 rpm. Agar (1.5% wt/vol) was added to prepare solid media.

Cloning, Expression, and Purification of P. falciparum DXR

The P. falciparum dxr gene was truncated to begin at Lys 75 to remove the apicoplast signaling sequence. A Pf 3D7 trophozoite cDNA library (MRA-297) was acquired from BEI resources and used as the template for amplification of the PfDXR gene. The gene was PCR amplified using primers 5' CACC AAG AAA CCA ATT AAT GTA GCA 3' forward and 5' CTA TAG AGA ATT ATG TTT GTT GTA TAT ATC GGT AG 3' reverse and cloned into a pET100/D-TOPO vector to yield pPfDXR, facilitating the expression of an N-terminal His$_6$-tagged protein.

The expression plasmid (pPfDXR) was separately transformed into chemically competent *E. coli* Rosetta2(DE3) cells for protein expression. To express the His-tagged protein, a 10 mL overnight seed culture was added to 1 L of LB media and then incubated with shaking at 37° C. and 250 rpm. At an OD$_{600}$ of 1.8, protein expression was induced with addition of isopropyl b-D-thiogalactopyranoside (IPTG) to 0.5 mM and the culture was further incubated with shaking at 37° C. and 250 rpm for an additional 18 hours. Cells were harvested via centrifugation (4648×g, 20 min, 4° C.) and stored at −80° C. Protein was subsequently isolated and purified from the cells via chemical lysis and affinity chromatography.

Cells were lysed with lysis buffer A (100 mM Tris pH 8.0, 0.032% lysozyme, 3 mL per gram cell pellet), followed by lysis buffer B (0.1 M CaCl$_2$, 0.1 M MgCl$_2$, 0.1 M NaCl, 0.020% DNase, 0.3 mL per gram cell pellet). Clarified cell lysate was collected after centrifugation (48,000×g, 20 min, 4° C.) and passed through a TALON immobilized metal affinity column (Clontech Laboratories, Mountain View, Calif.).

The column was washed with 20 column volumes of 1× equilibrium buffer (50 mM HEPES pH 7.5, 300 mM NaCl), 10 column volumes of 1× wash buffer (50 mM HEPES pH 7.5, 300 mM NaCl, 10 mM imidazole), and 15 column volumes of 2× wash buffer (100 mM HEPES pH 7.5, 600 mM NaCl, 20 mM imidazole). The protein was eluted with 5 column volumes of 1× elution buffer (150 mM imidazole pH 7.0, 300 mM NaCl). Buffer was exchanged with 0.1 M Tris pH 7.5, 1 mM NaCl, 5 mM DTT during concentration by ultrafiltration. Protein concentration was determined using Advanced Protein Assay Reagent (Cytoskeleton, Denver Colo.) with γ-globulins (Sigma-Aldrich) as the standard. Purified protein was visualized via Coomassie stained SDS-PAGE. The yield of PfDXR averages 1 mg per 1 L shake flask.

P. falciparum Culture.

P. falciparum strain 3D7 (wild-type, WT) was obtained through MR4 as part of the BEI Resources Repository, NIAID, NIH (www.mr4.org). A P. falciparum strain containing increased levels of MEP pathway metabolites, had1 (MRA-1257), and its isogenic compliment, had1+PfHad1-GFP (MRA-1258), were generated in strain 3D7, as reported (Guggisberg et al.). Parasites were cultured in a 2% suspension of human erythrocytes and RPMI 1640 (Sigma) medium supplemented with 27 mM sodium bicarbonate, 11 mM glucose, 5 mM HEPES, 1 mM sodium pyruvate, 0.37 mM hypoxanthine, 0.01 mM thymidine, 10 µg/mL gentamicin, and 0.5% Albumax (Gibco) at 37° C., 5% O$_2$/5% CO$_2$/90% N$_2$ atmosphere as previously described (Trager et al.; Zhang et al.).

HepG2 Cell Inhibition Assays:

For cytotoxicity assays, HepG2 cells (ATCC HB-8065) were grown in DMEM supplemented with 4 mM L-glutamine (Gibco #11966-025) with either 4.5 g/L D-glucose or 1.8 g/L galactose as carbon source. Cells were trypsinized, resuspended in the respective medium (DMEM/glutamine/glucose or DMEM/glutamine/galactose) to 4×10$^5$ cells/mL and 50 µL/well transferred to flat-bottom white opaque tissue culture plates (Falcon #353296) containing 50 µL/well of the respective medium with test compound. Compound concentrations were two-fold dilutions ranging from 50 µM to 0.049 µM as well as the drug-free DMSO-only control. All concentrations were tested in duplicate for each carbon source. After 24 h incubation at 5% CO$_2$, 37° C., 10 µL/well of Celltiter-Glo reagent (Promega #G9241) was added and luminescence recorded after 20 min incubation in the dark.

MEP Pathway Metabolite Assay: Sample Preparation.

P. falciparum strain 3D7 was cultured at 37° C. in 30 mL volumes in 100 mm tissue culture dishes (Techno Plastic Products) at 4% hematocrit until >8% parasitemia. Cultures were synchronized until >75% of parasites were in ring stage growth, and then treated for 10 h with or without 18a at 65 nM (5× the 3D7 IC50) in triplicate. Cultures were lysed with 5% saponin, the parasite pellets washed with 1× phosphate-buffered saline (PBS), and the pellets stored at −80° C. MEP pathway intermediates were extracted via the addition of glass beads (212-300 u) and 600 µL chilled H2O:chloroform:methanol (3:5:12 v/v) spiked with PIPES (piperazine-N,N'-bis(2-ethanesulfonic acid) as internal standard. The cells were disrupted with the TissueLyser II instrument (Qiagen) using a microcentrifuge tubes adaptor set pre-chilled for 2 min at 20 Hz. The samples were then centrifuged at 16,000 g at 4° C., the supernatants collected, and pellet extraction repeated once more. The supernatants were pooled and 300 µL chloroform and 450 µL of chilled water were added to the supernatants. The tubes were vortexed and centrifuged. The upper layer was transferred to a new tube and dried using a speed-vac. The pellets were re-dissolved in 100 µL of 50% acetonitrile.

LC-MS/MS Analysis.

For LC separation, a Luna-NH2 column (3 um, 150×2 mm, Phenomenex) was used flowing at 0.4 mL/min. The gradient of the mobile phases A (20 mM ammonium acetate, pH 9.8, 5% ACN) and B (100% acetonitrile) was as follows: 60% B for 1 min, to 6% B in 3 min, hold at 6% B for 5 min, then back to 60% B in 0.5 min. The LC system was interfaced with a Sciex QTRAP 6500+ mass spectrometer equipped with a TurboIonSpray (TIS) electrospray ion source. Analyst software (version 1.6.3) was used to control sample acquisition and data analysis. The QTRAP 6500+ mass spectrometer was tuned and calibrated according to the manufacturer's recommendations. Metabolites were detected using MRM transitions that were previously optimized using standards. The instrument was set-up to acquire in negative mode. For quantification, an external standard curve was prepared using a series of standard samples containing different concentrations of metabolites and fixed concentration of the internal standard. The limit of detection for deoxyxylulose 5-phosphate (DOXP), methylerythritol phosphate (MEP), cytidine diphosphate methylerythritol (CDP-ME), and methylerythritol cyclodiphosphate (MEcPP) was 0.0064 µM for a 10 µL injection volume.

Mouse Liver Microsomes and Plasma Stability.

In this protocol, the metabolic stability of compounds at 1 µM was determined in mouse liver microsomes (MLM) and mouse plasma. For microsomal stability each test compound was incubated in an aqueous reaction mixture consisting of 0.25 µM microsomal protein CYP450 activity, 1.2 mM NADPH, 3.3 mM MgCl2, and 100 mM potassium phosphate buffer (pH 7.4). For plasma stability each test compound was incubated in mouse plasma (VWR). After incubation at 37° C. a 50 µL aliquot of the reaction was transferred to 200 µL ice cold acetonitrile containing internal standard (Enalapril, 100 ng/mL). The quenched reaction mixtures were centrifuged at 3200 rpm for 5 min, and 100 µL of the supernatant were transferred to 96-well plate and analyzed by LC-MS/MS using an Applied Biosystems-Sciex API 4000. Analyte/internal standard peak area ratios were used to evaluate stability. The MRM transitions for enalapril, 12a, and 18a were m/z: 376.9>91.2, 511.197>102.1 and 283.259>102.1, respectively. An Amour C18 column (2.1×30 mm, 5 µm; Analytical Sales and Services, Pompton Plains, N.J.) was used for chromatographic separation. Mobile phases were 0.1% formic acid, 1 mM triethylamine in water and acetonitrile with a flow rate of 0.35 mL/min. The starting phase was 0% acetonitrile increased to 100% acetonitrile over 3 minutes. Peak areas were integrated using Analyst Software (AB Sciex, Foster City, Calif.).

In Vivo Exposure Study.

Animal care and all procedures were conducted at Charles River Laboratories (Wilmington, Mass.) and performed in accordance with the National Institutes of Health Guide for the Care and Use of Laboratory Animals and approved by the institutional animal care and use committee. Compound 18a was added to 2% methylcellulose 0.5% Tween80 and sonicated to make a 10 mg/mL suspension. The suspension was administered to unfasted female Swiss Weber mice (n=3) at 20 mg/kg i.p. Plasma samples (10 µL) were removed at 0.25, 0.5, 1, 2, 4, 6 and 8 h and stored at −80° C. Plasma samples were added to ice cold acetonitrile containing the internal standard, glafenine, as appropriate to bring samples into the standard curve range (50-10,000 ng/ml), then centrifuged for 5 minutes at 3200 rpm and the supernatant transferred to a 96-well sample plate for analysis by liquid chromatography-tandem mass spectrometry. The MRM transitions for glafenine and 12a were m/z: 370.9>296.9 and 180.075>119.9, respectively. A Synergi 4 µm Hydro-RP column (250×4.6 mm, 80 Å) was used for chromatographic separation. Mobile phases were 0.1% formic acid in water and acetonitrile with a flow rate of 1.2 mL/min. The starting phase was 0% acetonitrile for 3 minutes, increased to 60% acetonitrile over 6 minutes. Peak areas were integrated using Analyst Software (AB Sciex, Foster City, Calif.).

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A compound of Formula (I):

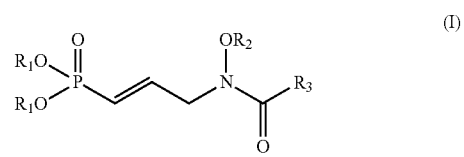

or a pharmaceutically acceptable salt or prodrug thereof, wherein each $R_1$ is independently $C_{1-6}$ haloalkyl, $C_{3-6}$ cycloalkyl, $(CR^aR^b)_m$-aryl, $(CR^aR^b)_m$-O(C=O)—$C_{1-6}$ alkyl, $(CR^aR^b)_m$-O(C=O)—$C_{3-6}$ cycloalkyl, $(CR^aR^b)_m$-O(C=O)-aryl, $(CR^aR^b)_m$-O(C=O)O—$C_{1-6}$ alkyl, or $(CR^aR^b)_m$—O(C=O)O—$C_{3-6}$ cycloalkyl, wherein the atom at the left is attached to the oxygen atom; or two $R_1$ taken together with the oxygen atoms and the phosphorus atom to form a 5-to 6-membered optionally substituted ring;

$R_2$ is $(CR^cR^d)_n$-aryl, wherein the atom at the left is attached to the oxygen atom;

$R_3$ is H, $C_{1-6}$ alkyl, $C_{1-6}$ haloalkyl, $C_{3-6}$ cycloalkyl, $C_{1-6}$ alkoxy, $C_{1-6}$ haloalkoxy, $C_{3-6}$ cycloalkoxy, or $(CR^eR^f)_p$-aryl;

each $R^a$, $R^b$, $R^c$, $R^d$, $R^e$, and $R^f$ is independently H, halogen, methyl, or ethyl; m and n is independently 1, 2, 3, or 4;

p is 0, 1, 2, 3, or 4;

each aryl is optionally substituted with up to five $R_4$ selected from the group consisting of halogen, hydroxyl, cyano, amino, ($C_{1-6}$ alkyl)amino, di($C_{1-6}$ alkyl)amino, $C_{1-6}$ alkyl, $C_{1-6}$ haloalkyl, $C_{3-6}$ cycloalkyl, $C_{1-6}$ alkoxy, $C_{1-6}$ haloalkoxy, and $C_{3-6}$ cycloalkoxy.

2. The compound of claim 1, wherein the compound is a pharmaceutically acceptable salt.

3. The compound of claim 2, wherein the salt is a Na$^+$, K$^+$, or quaternary ammonium salt.

4. The compound of claim 3, wherein the salt is a Na$^+$ or NH$_4^+$ salt.

5. The compound of any one of claims 1 to 4, wherein the compound is a mono- or di-salt.

6. The compound of claim 1, wherein $R_1$ is $(CR^aR^b)_m$-O (C=O)—$C_{1-6}$ alkyl.

7. The compound of claim 6, wherein $R_1$ is CH$_2$—O (C=O)—C(CH$_3$)$_3$.

8. The compound of claims 1, 4, 6, or 7, wherein $R_2$ is $(CR^aR^b)$-aryl.

9. The compound of claim 8, wherein $R_2$ is CH$_2$-aryl.

10. The compound of claim 9, wherein the aryl is optionally substituted phenyl, biphenyl, or naphthyl.

11. The compound of claims 1, 4, 6, 7, 9, or 10, wherein $R_3$ is H, $C_{1-3}$ alkyl, $C_{1-3}$ haloalkyl, $C_{1-3}$ alkoxy, $C_{1-3}$ haloalkoxy, or $(CH_2)_p$-aryl.
12. The compound of claim 11, wherein $R_3$ is H, $CH_3$, $CF_3$, $OCH_3$, phenyl, or benzyl.
13. The compound of claim 12, wherein $R_3$ is H, $CH_3$, or phenyl.
14. The compound of claim 13, wherein $R_3$ is H.
15. The compound of claim 13, wherein $R_3$ is $CH_3$.
16. A compound selected from the group consisting of:
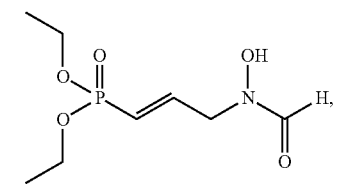
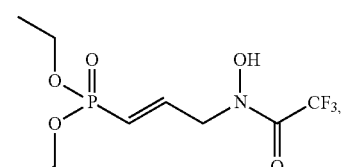
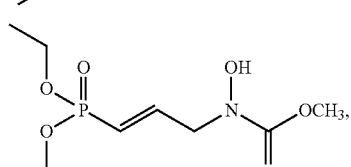
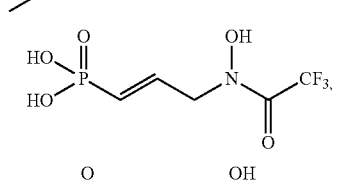
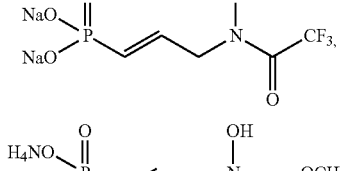
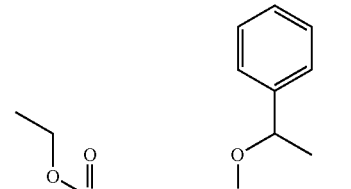
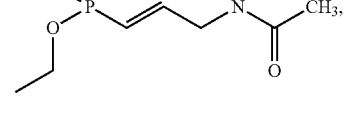
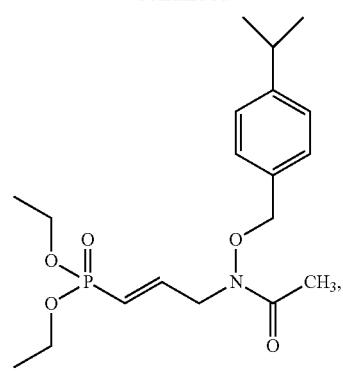
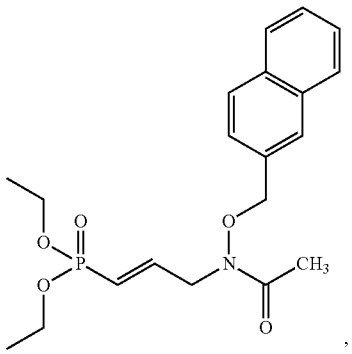
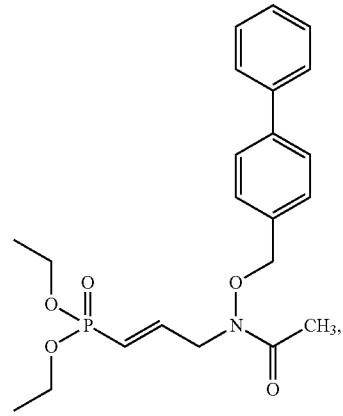
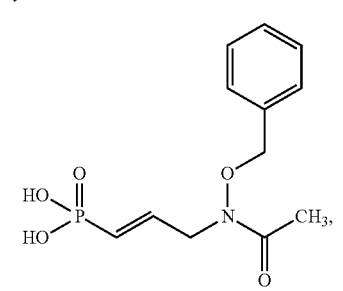
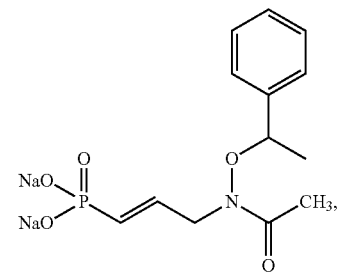

51
-continued
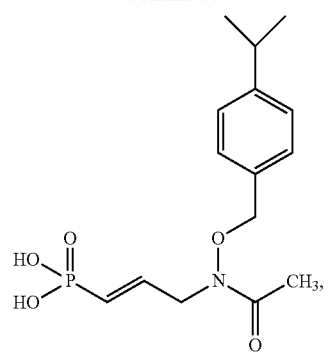
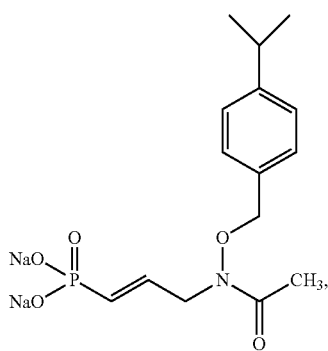
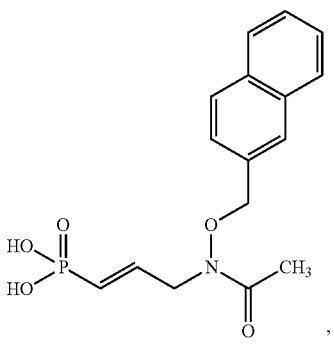
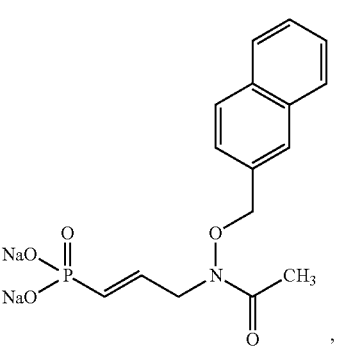
52
-continued
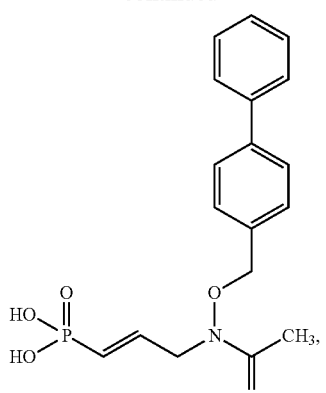

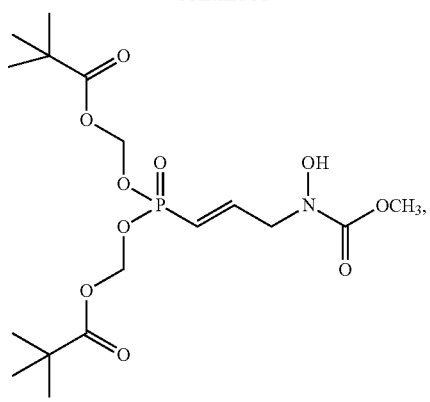
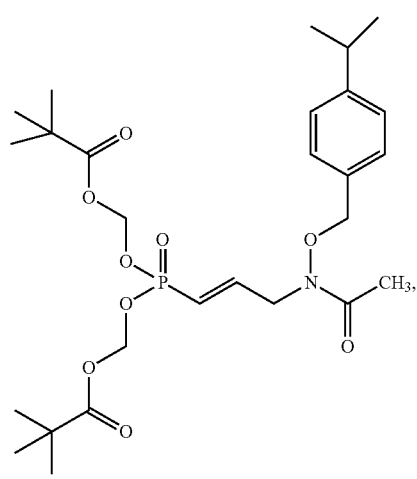
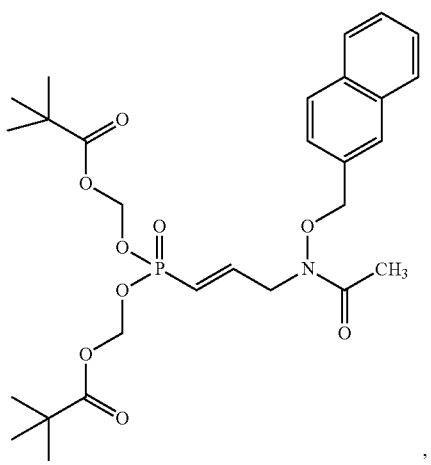
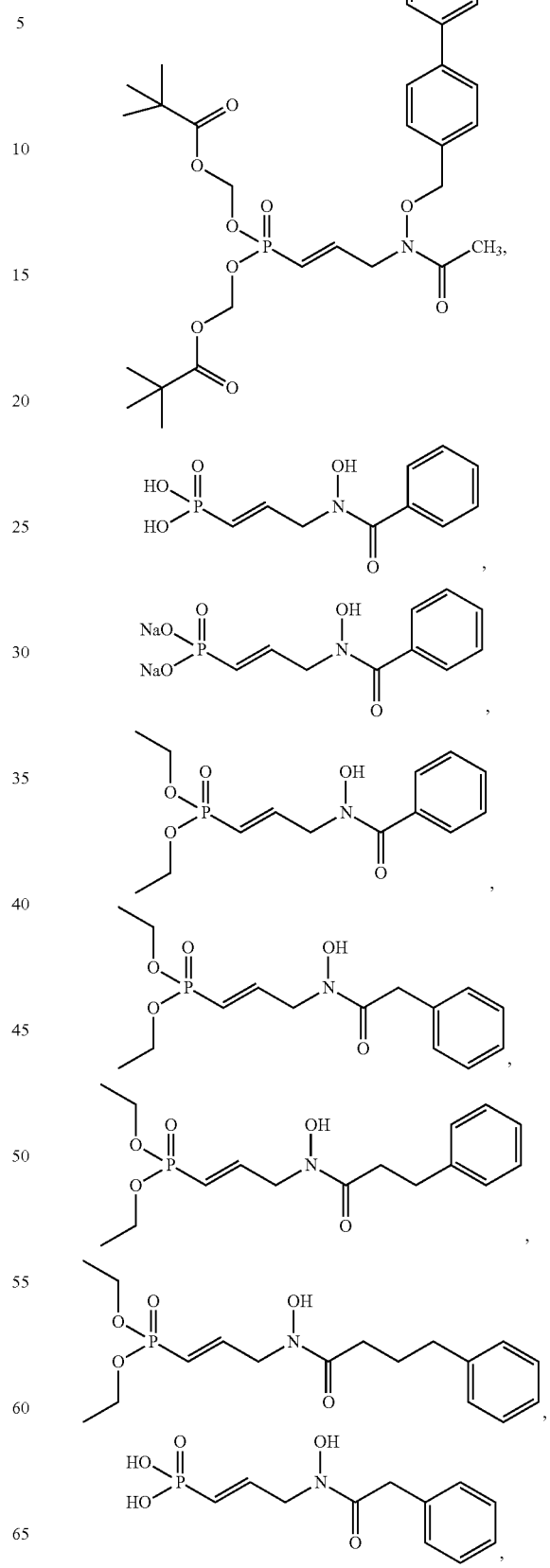

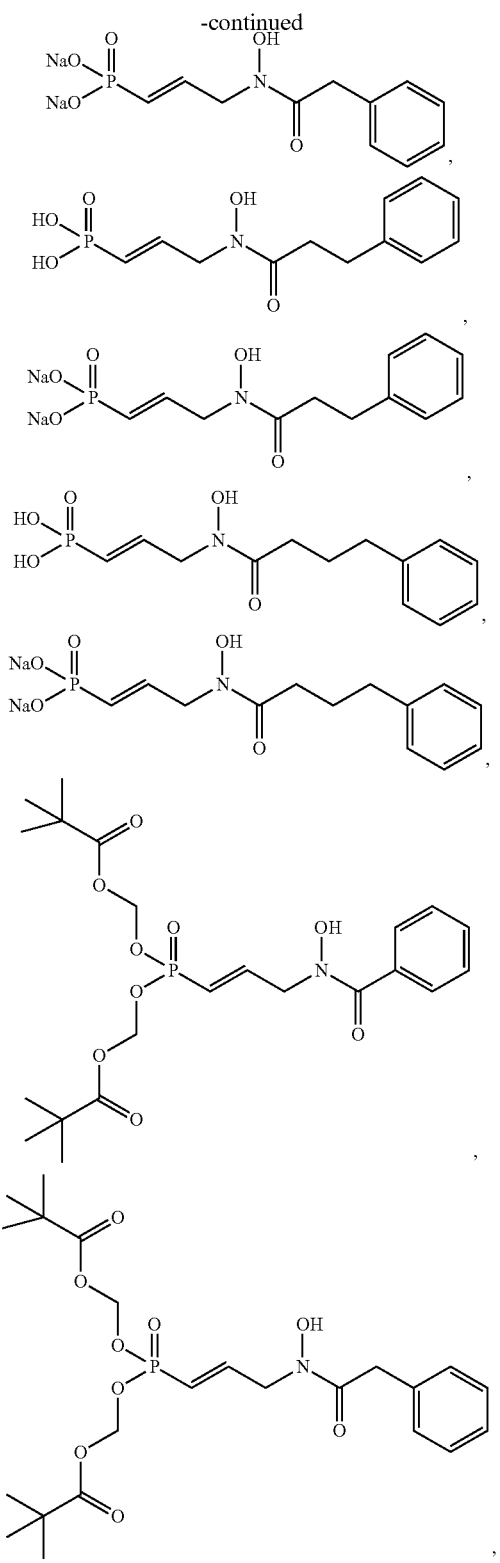

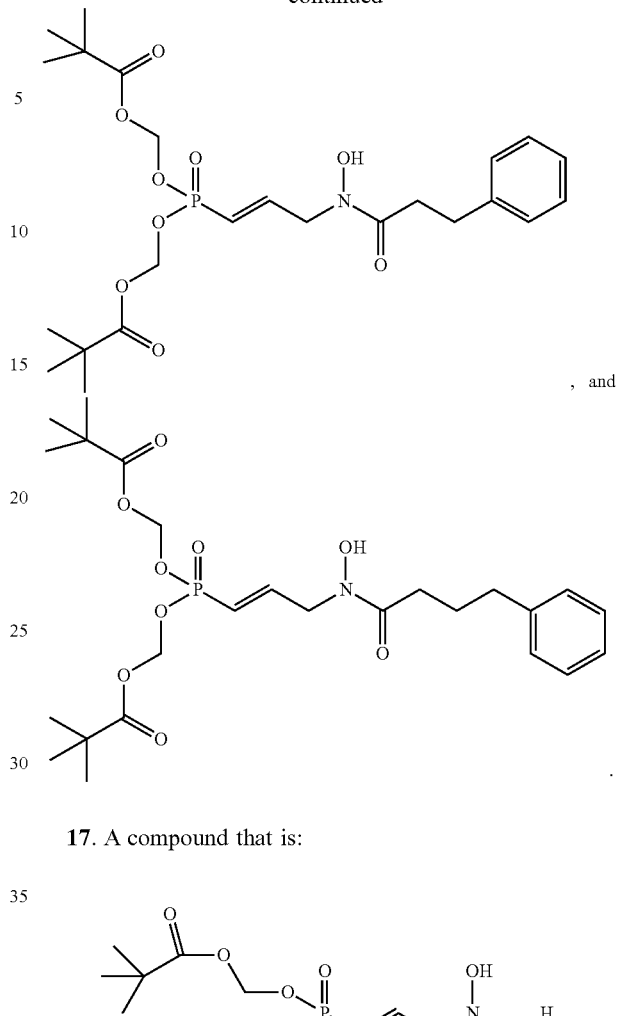

17. A compound that is:

, and .

18. A pharmaceutical composition comprising the compound of claims 1, 4, 6, 7, 9, 10, 12-16, or 17 and a pharmaceutically acceptable excipient.

19. A method for treating or preventing a microbial infection in a subject in need thereof comprising administering to the subject an effective amount of the compound of claims 1, 4, 6, 7, 9, 10, 12-16, or 17.

20. The method of claim 19, wherein the microbial infection is malaria.

21. The method of claim 19, wherein the microbial infection is tuberculosis.

22. The method of claim 19, wherein the subject is a human.

* * * * *

UNITED STATES PATENT AND TRADEMARK OFFICE
CERTIFICATE OF CORRECTION

PATENT NO.        : 11,098,072 B2
APPLICATION NO.   : 16/627004
DATED             : August 24, 2021
INVENTOR(S)       : Dowd et al.

Page 1 of 1

It is certified that error appears in the above-identified patent and that said Letters Patent is hereby corrected as shown below:

In the Claims

In Claim 16, Column 50, Lines 46-55, delete " 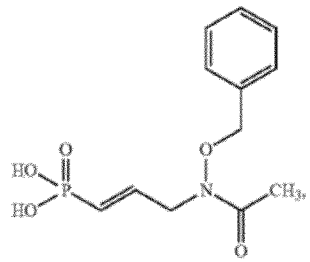 " and insert -- 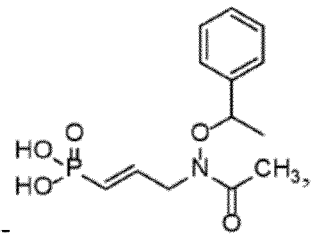 --, therefor.

Signed and Sealed this
Thirtieth Day of November, 2021

Drew Hirshfeld
*Performing the Functions and Duties of the
Under Secretary of Commerce for Intellectual Property and
Director of the United States Patent and Trademark Office*